(12) United States Patent
Van Almsick et al.

(10) Patent No.: US 7,569,519 B2
(45) Date of Patent: Aug. 4, 2009

(54) SUBSTITUTED BENZOYL DERIVATIVES AS HERBICIDES

(75) Inventors: Andreas Van Almsick, Karben (DE); Lothar Willms, Hofheim (DE); Hermann Bieringer, Eppstein (DE); Hubert Menne, Hofheim (DE); Thomas Auler, Bad Soden (DE)

(73) Assignee: Bayer CropScience AG, Frankfurt am Main (DE)

( * ) Notice: Subject to any disclaimer, the term of this patent is extended or adjusted under 35 U.S.C. 154(b) by 0 days.

(21) Appl. No.: 11/807,820

(22) Filed: May 30, 2007

(65) Prior Publication Data

US 2007/0244008 A1   Oct. 18, 2007

Related U.S. Application Data

(63) Continuation of application No. 10/754,081, filed on Jan. 8, 2004, now abandoned.

(30) Foreign Application Priority Data

Jan. 9, 2003   (DE) ................. 103 01 110

(51) Int. Cl.
*C07D 231/12* (2006.01)
*C07D 231/14* (2006.01)
*A01N 43/56* (2006.01)

(52) U.S. Cl. ............... 504/280; 504/282; 504/287; 548/366.1; 548/564

(58) Field of Classification Search ............... 504/280, 504/282, 287; 548/363, 366.1
See application file for complete search history.

(56) References Cited

U.S. PATENT DOCUMENTS

| 6,207,618 | B1 | 3/2001 | Engel et al. |
| 6,274,600 | B1 | 8/2001 | Lynch et al. |
| 6,432,881 | B1 * | 8/2002 | Engel et al. ............ 504/280 |

FOREIGN PATENT DOCUMENTS

| WO | WO-99/10327 | 3/1999 |
| WO | WO-99/10328 | 3/1999 |

OTHER PUBLICATIONS

Search Notes dated Aug. 7, 2006.

* cited by examiner

*Primary Examiner*—Golam M. M. Shameem
*Assistant Examiner*—Susannah Chung
(74) *Attorney, Agent, or Firm*—Connolly, Bove Lodge & Hutz LLP

(57) ABSTRACT

What is described are derivatives of benzoyl derivatives of the formula (I) and their use as herbicides.

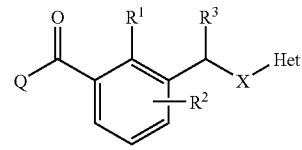

In this formula (I), $R^1$, $R^2$ and $R^3$ are different radicals, X is a bridge atom selected from the group consisting of oxygen and sulfur and Het is a saturated heterocyclic group which comprises oxygen and carbon atoms.

9 Claims, No Drawings

SUBSTITUTED BENZOYL DERIVATIVES AS HERBICIDES

The invention relates to the technical field of herbicides, in particular that of the herbicides from the group of the benzoylcyclohexanediones and benzoylpyrazoles for selectively controlling broad-leaved weeds and weed grasses in crops of useful plants, in particular in crops of rice.

From various publications, it is already known that certain benzoyl derivatives have herbicidal properties. Thus, WO 99/10327 and WO 99/10328 disclose benzoylcyclohexanediones and benzoylpyrazolones carrying a heterocyclyl or heteroaryl radical, attached via a multiatom bridge, in the 3-position of the phenyl ring.

However, the compounds known from these publications frequently have insufficient herbicidal activity.

It is an object of the present invention to provide further herbicidally active compounds which have improved herbicidal properties compared with the compounds known from the prior art.

It has now been found that benzoyl derivatives which carry certain heterocyclyl radicals, attached via a two-atom bridge, in the three-position of the phenyl ring are particularly suitable as herbicides. Accordingly, the present invention provides compounds of the formula (I) and salts thereof

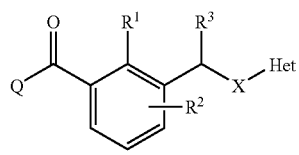

in which the radicals and indices are as defined below:

$R^1$, $R^2$ independently of one another are hydrogen, mercapto, nitro, halogen, cyano, thiocyanato, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, —$OR^4$, $OCOR^4$, $OSO_2R^4$, $S(O)_nR^4$, $SO_2OR^4$, $SO_2N(R^4)_2$, $NR^4SO_2R^4$, $NR^4COR^4$, $C_1$-$C_6$-alkyl-$S(O)_nR^4$, $C_1$-$C_6$-alkyl-$OR^4$, $C_1$-$C_6$-alkyl-$OCOR^4$, $C_1$-$C_6$-alkyl-$OSO_2R^4$, $C_1$-$C_6$-alkyl-$SO_2OR^4$, $C_1$-$C_6$-alkyl-$SO_2N(R^4)_2$ or $C_1$-$C_6$-alkyl-$NR^4COR^4$;

$R^3$ is hydrogen, $C_1$-$C_6$-alkyl, $C_2$-$C_6$-alkenyl or $C_2$-$C_6$-alkynyl;

$R^4$ is hydrogen, $C_1$-$C_6$-alkyl, $C_2$-$C_6$-alkenyl, $C_2$-$C_6$-alkynyl, $C_3$-$C_6$-cycloalkyl, phenyl or phenyl-$C_1$-$C_6$-alkyl, where the six last-mentioned radicals are substituted by s radicals selected from the group consisting of hydroxy, mercapto, amino, cyano, nitro, thiocyanato, $OR^3$, $SR^3$, $N(R^3)_2$, =$NOR^3$, $OCOR^3$, $SCOR^3$, $NR^3COR^3$, $CO_2R^3$, $COSR^3$, $CON(R^3)_2$, $C_1$-$C_4$-alkyliminooxy, $C_1$-$C_4$-alkoxyamino, $C_1$-$C_4$-alkylcarbonyl, $C_1$-$C_4$-alkoxy-$C_2$-$C_6$-alkoxycarbonyl and $C_1$-$C_4$-alkylsulfonyl;

Het is a fully saturated heterocyclic group whose ring atoms consist of carbon and oxygen atoms, where
    the total number of ring atoms is p,
    the number of oxygen atoms is r,
    the number of carbon atoms is (p−r) and
    Het may be substituted by n radicals $R^5$;

n is 0, 1 or 2;
p is 5, 6 or 7;
r is 1 or 2;
s is, 1, 2 or 3;
X is O or $S(O)_n$;
$R^5$ is hydroxy, mercapto, amino, cyano, nitro, halogen, formyl, $C_1$-$C_6$-alkylamino, $C_1$-$C_6$-dialkylamino, $C_1$-$C_6$-alkoxycarbonyl, $C_1$-$C_6$-alkylcarbonyl, $C_1$-$C_4$-alkylcarbonyloxy, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy, $C_1$-$C_6$-haloalkoxy or $R^5$ together with the carbon atom to which it is attached forms a carbonyl group;
Q is a radical of group Q1 or Q2;

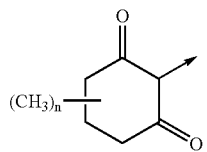

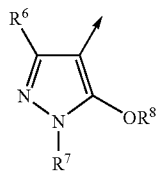

$R^6$, $R^7$ independently of one another are hydrogen, $C_1$-$C_6$-alkyl, $C_1$-$C_6$-haloalkyl or $C_3$-$C_6$-cyclopropyl;

$R^8$ is hydrogen, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, phenylcarbonyl, phenylcarbonylmethyl, phenyloxycarbonyl or phenylsulfonyl, where the phenyl ring of the four last-mentioned radicals is substituted by s radicals selected from the group consisting of halogen, nitro, cyano, $C_1$-$C_6$-alkyl, $C_1$-$C_6$-haloalkyl, $C_1$-$C_6$-alkoxy and $C_1$-$C_6$-haloalkoxy.

Depending on external conditions such as solvent and pH, the compounds of the formula (I) according to the invention can exist in different tautomeric structures. Depending on the nature of the substituents, the compounds of the formula (I) contain an acidic proton, which can be removed by reaction with a base. Examples of suitable bases are hydrides, hydroxides and carbonates of alkali metals and alkaline earth metals such as lithium, sodium, potassium, magnesium and calcium, and also ammonia and organic amines such as triethylamine and pyridine. Such salts are likewise provided by the invention.

In the formula (I) and in all subsequent formulae, alkyl radicals having more than two carbon atoms can be straight-chain or branched. Alkyl radicals are, for example, methyl, ethyl, n- or isopropyl, n-, iso-, t- or 2-butyl, pentyls, hexyls, such as n-hexyl, isohexyl and 1,3-dimethylbutyl, preferably methyl or ethyl.

If a group is substituted by a plurality of radicals, this is to be understood as meaning that this group is substituted by one or more identical or different of the radicals mentioned.

Cycloalkyl denotes a carbocyclic saturated ring system having three to nine carbon atoms, for example cyclopropyl, cyclopentyl or cyclohexyl. Analogously, cycloalkenyl denotes a monocyclic alkenyl group having three to nine carbon ring members, for example cyclopropenyl, cyclobutenyl, cyclopentenyl and cyclohexenyl, where the double bond may be located in any position. In the case of composed radicals such as cycloalkylalkenyl, the radical mentioned first may be in any position of the radical mentioned second.

"Heterocyclic group" is to be understood as meaning radicals such as 2-tetrahydrofuranyl, 3-tetrahydrofuranyl, 2-tetrahydropyranyl, 3-tetrahydropyranyl, 4-tetrahydropyranyl, 2-hexahydrooxepanyl, 3-hexahydrooxepanyl, 4-hexahydrooxepanyl, 1,3-dioxolan-4-yl, 1,3-dioxan-4-yl, 1,3-dioxan-5-yl and 1,4-dioxan-2-yl. Het is preferably unsubstituted or substituted by 1, 2, 3 or 4 methyl groups and/or 1 or 2 carbonyl groups.

In the case of a disubstituted amino group such as dialkylamino these two substituents may be identical or different.

Halogen denotes fluorine, chlorine, bromine or iodine. Haloalkyl, -alkenyl and -alkynyl denote alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$, $CH=CHCl$, $CH=CCl_2$, $C\equiv CCH_2Cl$; haloalkoxy is, for example, $OCF_3$, $OCHF_2$, $OCH_2F$, $CF_3CF_2O$, $OCH_2CF_3$ or $OCH_2CH_2Cl$; this applies correspondingly to haloalkenyl and other halogen-substituted radicals.

If a group is polysubstituted, this is to be understood as meaning that the general principles of the construction of chemical compounds must be taken into consideration when combining the various substituents, i.e. that the formation of compounds which are known to the skilled worker as being chemically unstable or impossible must be avoided.

Depending on the nature and linkage of the substituents, the compounds of the formula (I) can exist as stereoisomers. If, for example, one or more asymmetric carbon atoms are present, enantiomers and diestereomers may occur. Stereoisomers can be obtained by customary separation methods, for example by chromatographic separation methods, from the mixtures which are obtained in the preparation. It is also possible to prepare stereoisomers selectively by employing stereoselective reactions using optically active starting materials and/or auxiliaries. The invention relates to all stereoisormers and their mixtures which are embraced by formula (I), but not specifically defined.

Compounds of the formula (I) in which
$R^1$, $R^2$ independently of one another are hydrogen, nitro, halogen, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, —$OR^4$, $S(O)_nR^4$, $SO_2OR^4$, $SO_2N(R^4)_2$, $NR^4SO_2R^4$ or $C_1$-$C_6$-alkyl-$S(O)_nR^4$;
$R^4$ is hydrogen, $C_1$-$C_4$-alkyl, $C_2$-$C_4$-alkenyl, $C_2$-$C_4$-alkynyl, $C_3$-$C_6$-cycloalkyl, phenyl or phenyl-$C_1$-$C_4$-alkyl, where the six last-mentioned radicals are substituted by s radicals selected from the group consisting of cyano, nitro, $R^3$, $OR^3$, $SR^3$ and $N(R^3)_2$ and the other substituents and indices are in each case as defined above, have been found to be advantageous.

Preference is given to compounds of the formula (I), in which
$R^3$ is hydrogen;
$R^5$ is cyano, nitro, halogen, $C_1$-$C_4$-alkoxycarbonyl, $C_1$-$C_4$-alkylcarbonyl, $C_1$-$C_4$-alkylcarbonyloxy, $C_1$-$C_4$-alkyl, $C_1$-$C_4$-haloalkyl, $C_1$-$C_4$-alkylthio, $C_1$-$C_4$-haloalkylthio, $C_1$-$C_6$-alkoxy, $C_1$-$C_6$-haloalkoxy, or $R^5$ together with the carbon atom to which it is attached forms a carbonyl group;
$R^5$ is, in particular, methyl or methoxy, or $R^5$ together with the carbon atom to which it is attached forms a carbonyl group and the other substituents and indices are in each case as defined above.

Particular preference is given to compounds of the formula (I), in which
$R^6$, $R^7$ independently of one another are hydrogen or $C_1$-$C_4$-alkyl, in particular methyl or ethyl, or cyclopropyl;

$R^8$ is hydrogen, $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxycarbonyl, $C_1$-$C_4$-alkylsulfonyl, $C_1$-$C_4$-haloalkylsulfonyl, phenylcarbonyl, phenylcarbonylmethyl, phenyloxycarbonyl or phenylsulfonyl, where the phenyl ring of the four last-mentioned radicals is substituted by s radicals selected from the group consisting of halogen, nitro, cyano, $C_1$-$C_4$-alkyl, $C_1$-$C_4$-haloalkyl, $C_1$-$C_4$-alkoxy and $C_1$-$C_4$-haloalkoxy, and the other substituents and indices are in each case as defined above.

Very particular preference is given to compounds of the formula (I) in which
$R^1$ is chlorine, bromine, iodine, nitro, methyl, thiomethyl, thioethyl, methylsulfonyl, ethylsulfonyl or methoxy;
$R^2$ is bromine, chlorine, methylsulfonyl or ethylsulfonyl;
$R^2$ is located in the 4-position of the phenyl rings;
$R^8$ is hydrogen;
Het is 3-tetrahydrofuranyl, 3-tetrahydropyranyl, 4-tetrahydropyranyl, 1,3-dioxan-5-yl or γ-butyrolacton-2-yl, and the other substituents and indices are in each case as defined above.

In the formulae mentioned below, substituents and symbols have, unless defined otherwise, the same meaning as described under formula (I).

Compounds according to the invention in which Q is Q1 can be prepared, for example, according to the method shown in Scheme 1 by base-catalyzed reaction of a compound of the formula (IIIa), in which T is halogen, hydroxy or alkoxy with a cyclohexanedione (II) in the presence of a cyanide source. Such methods are described, for example, in EP-A 0 369 803 and EP-B 0 283 261.

Scheme 1:

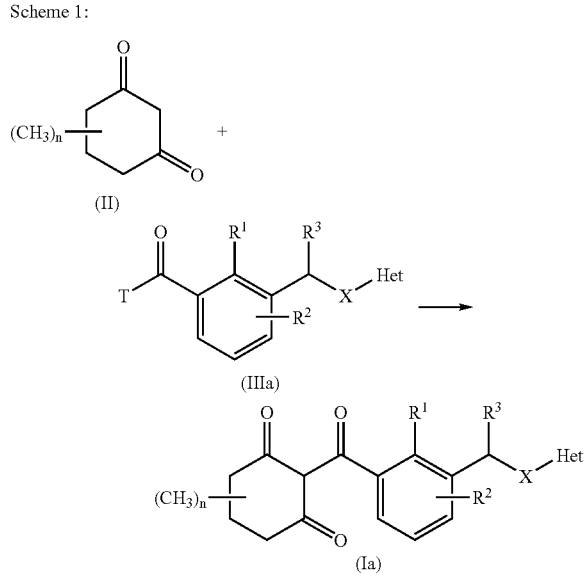

Compounds according to the invention in which Q is Q2 and R8 is hydrogen can be prepared, for example, by the method shown in Scheme 2. To this end, a compound of the formula (IIIa) is, either in the presence of a dehydrating agent such as DCC or after conversion into its acid chloride, reacted under base catalysis with a pyrazole of the formula (IV) and finally treated with a cyanide source. These methods are described, for example, in EP-A 0 369 803.

Scheme 2:

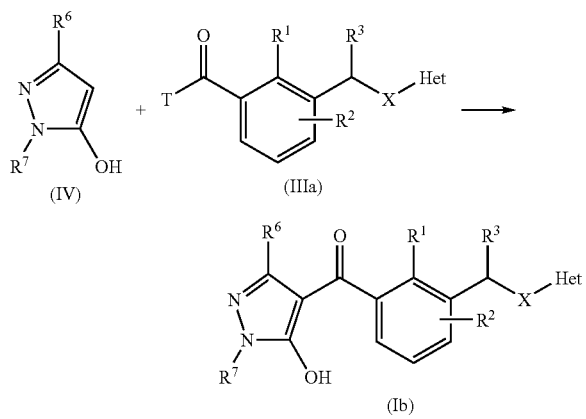

Compounds according to the invention of the formula (I) in which $R^8$ is a radical different from hydrogen can be prepared, for example, according to Scheme 3 by substitution reactions known per se to the person skilled in the art. To this end, compounds of the formula (Ib) are reacted with compounds of the formula (V) in which E is a nucleophilically exchangeable leaving group. Such methods are known, for example, from WO 99/10328.

Scheme 3:

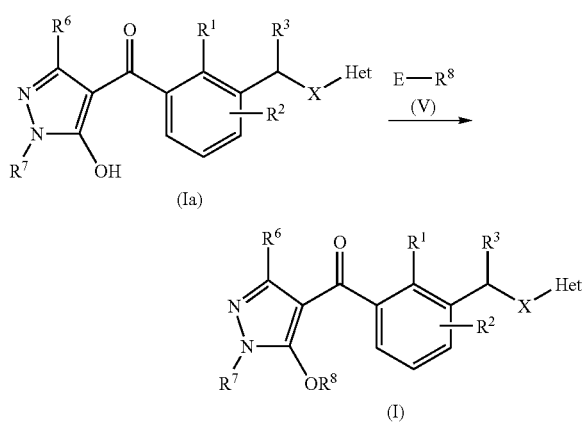

Compounds of the formula (IIIa), in which T is OH can be prepared, for example, according to Scheme 4 from compounds of the formula (Ib), in which Hal is halogen and $R^{10}$ is alkoxy or OH.

Scheme 4:

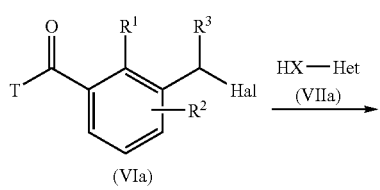

-continued

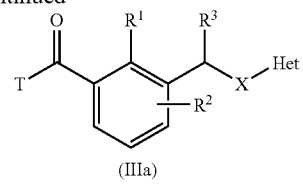

Compounds of the formula (IIIa) are also obtainable by reactions according to Scheme 5.

Scheme 5:

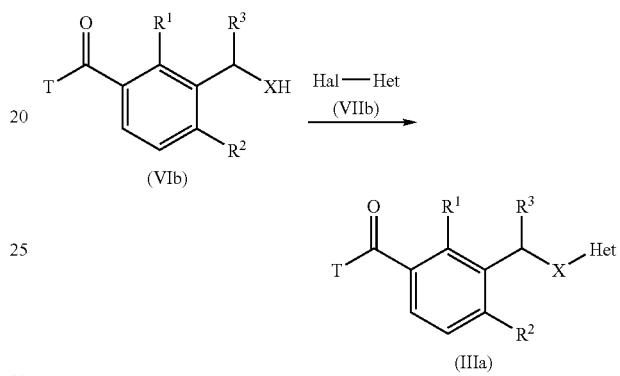

Compounds of the formulae (VIa) and (VIb) are known from the literature or can be prepared by known methods as described, for example, in WO 96/26200 and in the German patent application No. 10144412.5, which was unpublished at the priority date of the present invention.

The compounds of the formula (I) according to the invention have an outstanding herbicidal activity against a broad spectrum of economically important monocotyledonous and dicotyledonous harmful plants. The active substances also effect good control of perennial weeds which produce shoots from rhizomes, root stocks or other perennial organs and which are difficult to control. In this context, it is generally immaterial whether the substances are applied before sowing, pre-emergence or post-emergence. Specifically, some representatives of the monocotyledonous and dicotyledonous weed flora which can be controlled by the compounds according to the invention may be mentioned by way of example, without a restriction to certain species being intended to take place as a result of the mention. Amongst the monocotyledonous weed species, those on which the active substances act efficiently are, for example, *Avena, Lolium, Alopecurus, Phalaris, Echinochloa, Digitaria, Setaria* and *Cyperus* species from the annual group and, among the perennial species, *Agropyron, Cynodon, Imperata* and *Sorghum* and also perennial *Cyperus* species. In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* among the annuals and *Convolvulus, Cirsium, Rumex* and *Artemisia* in the case of the perennial weeds. Harmful plants occurring under the specific cultivation conditions of rice such as, for example, *Echinochloa, Sagittaria, Alisma, Eleocharis, Scirpus* and *Cyperus*, are also outstandingly well controlled by the active substances according to the invention. If the compounds according to the invention are applied to the soil surface before germination, then the weed seedlings are either prevented completely from emerging or the weeds grow until they have reached the cotyledon stage, but then their growth stops and they finally die completely after three to four weeks have elapsed. When the active substances are applied post-emergence to the green parts of the plants, growth also stops drastically a very short time after the treatment and the weed plants remain at the stage of growth at the time of application, or they die completely after a certain time, so that in this manner competition by the weeds, which is harmful to the crop plants, is eliminated at a very early stage and in a sustained manner. In particular, the compounds according to the invention are highly active against *Amaranthus retroflexus, Avena* sp., *Echinochloa* sp., *Cyperus serotinus, Lolium multiforum, Setaria viridis, Sagittaria pygmaea, Scirpus juncoides, Sinapis* sp. and *Stellaria media*.

Although the compounds according to the invention have excellent herbicidal activity against monocotyledonous and dicotyledonous weeds, crop plants of economically important crops such as wheat, barley, rye, rice, corn, sugar beet, cotton and soybeans, are damaged only to an insignificant extent or not at all. In particular, they are outstandingly well-tolerated in wheat, corn and rice. For these reasons, the present compounds are very highly suitable for selectively controlling undesired vegetation in stands of agriculturally useful plants or in stands of ornamental plants.

On account of their herbicidal properties, the active substances can also be employed for controlling harmful plants in crops of known genetically modified plants or genetically modified plants yet to be developed. As a rule, the transgenic plants are distinguished by particularly advantageous properties, for example by resistances to certain pesticides, especially certain herbicides, resistances to plant diseases or plant pathogens, such as certain insects or microorganisms such as fungi, bacteria or viruses. Other particular properties relate, for example, to the harvested material with respect to quantity, quality, storability, composition and specific constituents. Thus, transgenic plants with an increased starch content or in which the quality of the starch is altered, or those having a different fatty acid composition of the harvested material, are known.

The compounds of the formula (I) according to the invention or their salts are preferably used in economically important transgenic crops of useful plants and ornamentals, e.g. of cereals such as wheat, barley, rye, oats, sorghum and millet, rice, cassava and maize, or else crops of sugar beet, cotton, soybeans, oil seed rape, potatoes, tomatoes, peas and other types of vegetable. The compounds of the formula (I) can preferably be employed as herbicides in crops of useful plants which are resistant, or have been made resistant by recombinant methods, to the phytotoxic effect of herbicides.

Traditional ways of generating novel plants which have modified characteristics in comparison with existing plants consist, for example, in traditional breeding methods and the generation of mutants. Alternatively, novel plants with modified characteristics can be generated using recombinant procedures (see, for example, EP-A-0221044, EP-A-0131624). For example, a number of cases have been described of
  recombinant modifications of crop plants for the purpose of modifying the starch synthesized in the plants (for example WO 92/11376, WO 92/14827, WO 91/19806),
  transgenic crop plants which are resistant to certain herbicides of the glutosinate type (cf., for example, EP-A-0242236, EP-A-242246) or of the glyphosate type (WO 92/00377) or of the sulfonylurea type (EP-A-0257993, U.S. Pat. No. 5,013,659),
  transgenic crop plants, for example cotton, with the capability of producing *Bacillus thuringiensis* toxins (Bt toxins) which make the plants resistant to certain pests (EP-A-0142924, EP-A-0193259),
  transgenic crop plants having a modified fatty acid composition (WO 91/13972).

A large number of molecular-biological techniques with which novel transgenic plants with modified properties can be generated are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423-431).

To carry out such recombinant manipulations, nucleic acid molecules which permit a mutagenesis or a sequence modification by recombination of DNA sequences can be introduced into plasmids. For example, it is possible with the aid of the abovementioned standard methods to carry out base exchanges, to remove subsequences or to add natural or synthetic sequences. Adapters or linkers may be added in order to link the DNA fragments to each other.

For example, plant cells with a reduced activity of a gene product can successfully be generated by expressing at least one suitable antisense RNA, a sense RNA to achieve a cosuppression effect or by expressing at least one suitably constructed ribozyme which specifically cleaves transcripts of the abovementioned gene product.

To this end, it is possible to use firstly DNA molecules which encompass all of the coding sequence of a gene product including any flanking sequences which may be present and secondly DNA molecules which only encompass parts of the coding sequence, it being necessary for these parts to be of sufficient length to cause an antisense effect in the cells. Also possible is the use of DNA sequences which have a high degree of homology with the coding sequences of a gene product which are not entirely identical thereto.

When expressing nucleic acid molecules in plants, the protein synthesized may be localized in any compartment of the plant cell. However, to achieve localization in a particular compartment, it is possible for example to link the coding region with DNA sequences which guarantee localization in a certain compartment. Sequences of this type are known to the person skilled in the art, (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give intact plants. In principle, the transgenic plants can be plants of any desired plant species, i.e. both monocotyledonous and dicotyledonous plants.

Transgenic plants are thus obtainable which have modified properties as a result of overexpression, suppression or inhibition of homologous (=natural) genes or gene sequences, or expression of heterologous (=foreign) genes or gene sequences.

When the active substances according to the invention are used in transgenic crops, effects which are specific for application in the particular transgenic crop, for example a modified or specifically widened spectrum of weeds which can be controlled, altered application rates which can be employed for application, preferably good combining ability with the herbicides, to which the transgenic crop is resistant, and an effect on growth and yield of the transgenic crop plants, often occur in addition to the effects against harmful plants which can be observed in other crops. Subject matter of the invention is therefore also the use of the compounds according to the invention as herbicides for controlling harmful plants in transgenic crop plants.

The substances according to the invention additionally also have outstanding growth-regulatory properties in crop plants. They engage in the plants' metabolism in a regulatory fashion and can thus be employed for the targeted control of plant constituents and for facilitating harvesting, such as, for example, triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since lodging can be reduced, or prevented completely, hereby.

The compounds according to the invention can be employed in the form of wettable powders, emulsifiable concentrates, sprayable solutions, dusts or granules in the customary preparations. Accordingly, the invention also provides herbicidal agents comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Engineering], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflätchenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, e.g. butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates can be water-based or oil-based. They can be prepared for example by wet-grinding by means of customary bead mills, if appropriate with addition of surfactants, as have already been listed for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see, for example methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8-57.

For further details on the formulation of crop protection products see, for example G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the auxiliaries which are conventional in each case, such as stickers, wetters, dispersants, emulsifiers, penetrants, preservatives, antifreeze agents, solvents, fillers, carriers, colorants, antifoams, evaporation inhibitors, and pH and viscosity regulators.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Active substances which can be employed in combination with the active substances according to the invention in mixed formulations or in the tank mix are, for example, known active substances as are described, for example, in Weed Research 26, 441-445 (1986) or "The Pesticide Manual", 11th edition, The British Crop Protection Council and the Royal Soc. of Chemistry, 1997 and literature cited therein. Herbicides which must be mentioned, and can be combined with the compounds of the formula (I), are, for example, the following active substances (note: the compounds are either designated by the common name according to the International Organization for Standardization (ISO) or using the chemical name, if appropriate together with a customary code number):

acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuronmethyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDM, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethylester, HN-252); etobenzanid (HW 52); fenoprop; fenoxan, fenoxaprop and fenoxaprop-P and their esters, for example fenoxaprop-P-ethyl and fenoxapropethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentylester, S-23031); flumioxazin (S482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methylester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; mesotrione; metamitron; metazachlor; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; suclotrione; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)

phenyl]-1H-tetrazole; UBH-509; DA89; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are present in commercially available form, are diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use. The application rate required of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The invention is illustrated by the examples below.

A. CHEMICAL EXAMPLES

Preparation of 2-(2-chloro-3-(3-tetrahydrofuranyl) oxymethyl-4-methylsulfonyl-benzoyl)cyclohexane-1,3-dione (Tabulated Example No. 1.1)

Step 1: 2-chloro-3-(3-tetrahydrofuranyl)oxymethyl-4-methylsulfonylbenzoic acid

At 0° C., 25 ml of DMF and 3.25 g (28 mmol) of potassium tert-butoxide were initially charged and mixed with 2.5 g (27.5 mmol) of 3-hydroxytetrahydrofuran. The solution was cooled to −15° C., and 4.7 g (140 mmol) of 3-bromomethyl-2-chloro-4-methylsulfonylbenzoic acid were added. The mixture was then stirred at 15-20° C. for one hour. The reaction was poured into 45 g of ice/water, acidified with 2N HCl and extracted with EA. The organic phases were dried with $MgSO_4$, filtered and concentrated. This gave 5.41 g of a viscous oil of a purity of about 66% according to HPLC. Yield about 60%

Step 2: 3-Oxo-1-cyclohexenyl-2-chloro-3-(3-tetrahydrofuranyl)oxymethyl-4-methylsulfonylbenzoate 5.41 g of crude 2-chloro-3-(3-tetrahydrofuranyl)oxymethyl-4-methylsulfonylbenzoic acid were dissolved in 30 ml of $CH_2Cl_2$, and 2.5 ml (28 mmol) of oxalyl chloride were added slowly. The mixture was stirred for about 30 min until the evolution of gas had ceased. With cooling to a temperature of below 15° C., the solution was added dropwise to a mixture of 2 g (17.3 mmol) of 1,3-cyclohexanedione and 5 g of $NEt_3$ in 20 ml of $CH_2Cl_2$. The mixture was then stirred at RT for 1 hour. The mixture was filtered, the solvents were removed using a rotary evaporator and 30 ml of EA were then added to the residue. The mixture was washed initially with 5% strength HCl, then with 2% strength $NaHCO_3$ solution and twice with water. The organic phase was dried using $MgSO_4$, filtered and concentrated using a rotary evaporator. This gave 5 g of a highly viscous oil which was purified chromatographically ($SiO_2/_n$-heptane:EA, 1:3). This gave 2.95 g of a colorless solid of a purity of about 99% according to HPLC.

Step 3: 2-(2-Chloro-3-(3-tetrahydrofuranyl)oxymethyl-4-methylsulfonylbenzoyl)-cyclohexane-1,3-dione 8 g (18.5 mmol) of 3-oxo-1-cyclohexenyl-2-chloro-3-(3-tetrahydrofuranyl)oxymethyl-4-methylsulfonylbenzoate were suspended in 50 ml of $CH_3CN$, and 2.25 g (21.8 mmol) of $NEt_3$ and 0.13 g (1.5 mmol) of acetone cyanohydrin were added with stirring. The mixture was stirred at RT for 3 hours and then concentrated using a rotary evaporator. Water was added to the oily residue and the pH was adjusted to >8 using saturated $NaHCO_3$ solution. The basic solution was washed with 20 ml of EA. The aqueous solution was then acidified with 2N HCl and extracted with 2×50 ml of EA. The solution was washed with $NaHCO_3$ solution. The organic solution was dried with $MgSO_4$, filtered and concentrated using a rotary evaporator. The product slowly crystallized out from the concentrated solution. The solid was filtered off with suction and washed with cold EA. This gave 6.81 g (15.9 mmol) of product of a purity of 99.8% according to HPLC and a melting point of 126° C. The yield was 85%.

The abbreviations used here denote:
cPr=Cyclopropyl nPr=n-propyl nBu=n-butyl
Et=Ethyl Me=methyl Ph=Phenyl
EA=ethyl acetate m.p.=melting point RT=room temperature
Rf=retention value

TABLE 1

Compounds of the formula (I) according to the invention in which the substituents and symbols are as defined below:
$R^3$ = H Q = Q1 P = 0

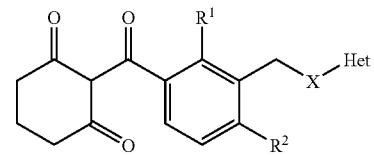

| No. | $R^1$ | $R^2$ | X | Het | Physical Data |
|-----|-------|-------|---|-----|---------------|
| 1.1 | Cl | $SO_2Me$ | O | 3-tetrahydrofuranyl | m.p.: 126° C. |
| 1.2 | Cl | $SO_2Et$ | O | 3-tetrahydrofuranyl | oil, Rf = 0.2 (EA) |
| 1.3 | Cl | Cl | O | 3-tetrahydrofuranyl | oil, Rf = 0.4 (EA) |
| 1.4 | Br | $SO_2Me$ | O | 3-tetrahydrofuranyl | |
| 1.5 | Br | $SO_2Et$ | O | 3-tetrahydrofuranyl | |
| 1.6 | Br | Cl | O | 3-tetrahydrofuranyl | |
| 1.7 | I | $SO_2Me$ | O | 3-tetrahydrofuranyl | |
| 1.8 | I | $SO_2Et$ | O | 3-tetrahydrofuranyl | |
| 1.9 | I | Cl | O | 3-tetrahydrofuranyl | |
| 1.10 | Me | $SO_2Me$ | O | 3-tetrahydrofuranyl | |
| 1.11 | Me | $SO_2Et$ | O | 3-tetrahydrofuranyl | |
| 1.12 | Me | Cl | O | 3-tetrahydrofuranyl | |
| 1.13 | SMe | $SO_2Me$ | O | 3-tetrahydrofuranyl | |
| 1.14 | SMe | $SO_2Et$ | O | 3-tetrahydrofuranyl | |
| 1.15 | SMe | Cl | O | 3-tetrahydrofuranyl | |
| 1.16 | $SO_2Me$ | $SO_2Me$ | O | 3-tetrahydrofuranyl | |
| 1.17 | $SO_2Me$ | $SO_2Et$ | O | 3-tetrahydrofuranyl | |
| 1.18 | $SO_2Me$ | Cl | O | 3-tetrahydrofuranyl | |
| 1.19 | $NO_2$ | $SO_2Me$ | O | 3-tetrahydrofuranyl | |
| 1.20 | $NO_2$ | $SO_2Et$ | O | 3-tetrahydrofuranyl | |
| 1.21 | $NO_2$ | Cl | O | 3-tetrahydrofuranyl | |
| 1.22 | OMe | Cl | O | 3-tetrahydrofuranyl | oil, Rf = 0.4 (EA) |
| 1.23 | $SO_2Et$ | Cl | O | 3-tetrahydrofuranyl | |
| 1.24 | SEt | Cl | O | 3-tetrahydrofuranyl | |
| 1.25 | Cl | $SO_2Me$ | O | 4-tetrahydropyranyl | |
| 1.26 | Cl | $SO_2Et$ | O | 4-tetrahydropyranyl | |
| 1.27 | Cl | Cl | O | 4-tetrahydropyranyl | |
| 1.28 | Br | $SO_2Me$ | O | 4-tetrahydropyranyl | |
| 1.29 | Br | $SO_2Et$ | O | 4-tetrahydropyranyl | |
| 1.30 | Br | Cl | O | 4-tetrahydropyranyl | |
| 1.31 | I | $SO_2Me$ | O | 4-tetrahydropyranyl | |
| 1.32 | I | $SO_2Et$ | O | 4-tetrahydropyranyl | |
| 1.33 | I | Cl | O | 4-tetrahydropyranyl | |
| 1.34 | Me | $SO_2Me$ | O | 4-tetrahydropyranyl | |
| 1.35 | Me | $SO_2Et$ | O | 4-tetrahydropyranyl | |
| 1.36 | Me | Cl | O | 4-tetrahydropyranyl | |
| 1.37 | SMe | $SO_2Me$ | O | 4-tetrahydropyranyl | |
| 1.38 | SMe | $SO_2Et$ | O | 4-tetrahydropyranyl | |
| 1.39 | SMe | Cl | O | 4-tetrahydropyranyl | |

TABLE 1-continued

Compounds of the formula (I) according to the invention in which the substituents and symbols are as defined below:
R³ = H Q = Q1 P = 0

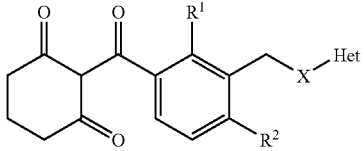

| No. | R¹ | R² | X | Het | Physical Data |
|---|---|---|---|---|---|
| 1.40 | SO₂Me | SO₂Me | O | 4-tetrahydropyranyl | |
| 1.41 | SO₂Me | SO₂Et | O | 4-tetrahydropyranyl | |
| 1.42 | SO₂Me | Cl | O | 4-tetrahydropyranyl | |
| 1.43 | NO₂ | SO₂Me | O | 4-tetrahydropyranyl | |
| 1.44 | NO₂ | SO₂Et | O | 4-tetrahydropyranyl | |
| 1.45 | NO₂ | Cl | O | 4-tetrahydropyranyl | |
| 1.46 | OMe | Cl | O | 4-tetrahydropyranyl | |
| 1.47 | SO₂Et | Cl | O | 4-tetrahydropyranyl | |
| 1.48 | SEt | Cl | O | 4-tetrahydropyranyl | |
| 1.49 | Cl | SO₂Me | O | 3-tetrahydropyranyl | |
| 1.50 | Cl | SO₂Et | O | 3-tetrahydropyranyl | |
| 1.51 | Cl | Cl | O | 3-tetrahydropyranyl | |
| 1.52 | Br | SO₂Me | O | 3-tetrahydropyranyl | |
| 1.53 | Br | SO₂Et | O | 3-tetrahydropyranyl | |
| 1.54 | Br | Cl | O | 3-tetrahydropyranyl | |
| 1.55 | I | SO₂Me | O | 3-tetrahydropyranyl | |
| 1.56 | I | SO₂Et | O | 3-tetrahydropyranyl | |
| 1.57 | I | Cl | O | 3-tetrahydropyranyl | |
| 1.58 | Me | SO₂Me | O | 3-tetrahydropyranyl | |
| 1.59 | Me | SO₂Et | O | 3-tetrahydropyranyl | |
| 1.60 | Me | Cl | O | 3-tetrahydropyranyl | |
| 1.61 | SMe | SO₂Me | O | 3-tetrahydropyranyl | |
| 1.62 | SMe | SO₂Et | O | 3-tetrahydropyranyl | |
| 1.63 | SMe | Cl | O | 3-tetrahydropyranyl | |
| 1.64 | SO₂Me | SO₂Me | O | 3-tetrahydropyranyl | |
| 1.65 | SO₂Me | SO₂Et | O | 3-tetrahydropyranyl | |
| 1.66 | SO₂Me | Cl | O | 3-tetrahydropyranyl | |
| 1.67 | NO₂ | SO₂Me | O | 3-tetrahydropyranyl | |
| 1.68 | NO₂ | SO₂Et | O | 3-tetrahydropyranyl | |
| 1.69 | NO₂ | Cl | O | 3-tetrahydropyranyl | |
| 1.70 | OMe | Cl | O | 3-tetrahydropyranyl | |
| 1.71 | SO₂Et | Cl | O | 3-tetrahydropyranyl | |
| 1.72 | SEt | Cl | O | 3-tetrahydropyranyl | |
| 1.73 | Cl | SO₂Me | O | 1,3-dioxan-5-yl | |
| 1.74 | Cl | SO₂Et | O | 1,3-dioxan-5-yl | |
| 1.75 | Cl | Cl | O | 1,3-dioxan-5-yl | |
| 1.76 | Br | SO₂Me | O | 1,3-dioxan-5-yl | |
| 1.77 | Br | SO₂Et | O | 1,3-dioxan-5-yl | |
| 1.78 | Br | Cl | O | 1,3-dioxan-5-yl | |
| 1.79 | I | SO₂Me | O | 1,3-dioxan-5-yl | |
| 1.80 | I | SO₂Et | O | 1,3-dioxan-5-yl | |
| 1.81 | I | Cl | O | 1,3-dioxan-5-yl | |
| 1.82 | Me | SO₂Me | O | 1,3-dioxan-5-yl | |
| 1.83 | Me | SO₂Et | O | 1,3-dioxan-5-yl | |
| 1.84 | Me | Cl | O | 1,3-dioxan-5-yl | |
| 1.85 | SMe | SO₂Me | O | 1,3-dioxan-5-yl | |
| 1.86 | SMe | SO₂Et | O | 1,3-dioxan-5-yl | |
| 1.87 | SMe | Cl | O | 1,3-dioxan-5-yl | |
| 1.88 | SO₂Me | SO₂Me | O | 1,3-dioxan-5-yl | |
| 1.89 | SO₂Me | SO₂Et | O | 1,3-dioxan-5-yl | |
| 1.90 | SO₂Me | Cl | O | 1,3-dioxan-5-yl | |
| 1.91 | NO₂ | SO₂Me | O | 1,3-dioxan-5-yl | |
| 1.92 | NO₂ | SO₂Et | O | 1,3-dioxan-5-yl | |
| 1.93 | NO₂ | Cl | O | 1,3-dioxan-5-yl | |
| 1.94 | OMe | Cl | O | 1,3-dioxan-5-yl | |
| 1.95 | SO₂Et | Cl | O | 1,3-dioxan-5-yl | |
| 1.96 | SEt | Cl | O | 1,3-dioxan-5-yl | |
| 1.97 | Cl | SO₂Me | O | γ-butyrolacton-2-yl | oil, Rf = 0.3 (EA) |
| 1.98 | Cl | SO₂Et | O | γ-butyrolacton-2-yl | |
| 1.99 | Cl | Cl | O | γ-butyrolacton-2-yl | |
| 1.100 | Br | SO₂Me | O | γ-butyrolacton-2-yl | |
| 1.101 | Br | SO₂Et | O | γ-butyrolacton-2-yl | |
| 1.102 | Br | Cl | O | γ-butyrolacton-2-yl | |
| 1.103 | I | SO₂Me | O | γ-butyrolacton-2-yl | |

TABLE 1-continued

Compounds of the formula (I) according to the invention in which the substituents and symbols are as defined below:
R³ = H Q = Q1 P = 0

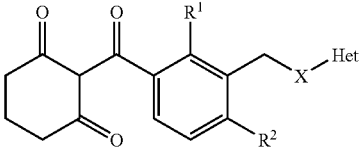

| No. | R¹ | R² | X | Het | Physical Data |
|---|---|---|---|---|---|
| 1.104 | I | SO₂Et | O | γ-butyrolacton-2-yl | |
| 1.105 | I | Cl | O | γ-butyrolacton-2-yl | |
| 1.106 | Me | SO₂Me | O | γ-butyrolacton-2-yl | |
| 1.107 | Me | SO₂Et | O | γ-butyrolacton-2-yl | |
| 1.108 | Me | Cl | O | γ-butyrolacton-2-yl | |
| 1.109 | SMe | SO₂Me | O | γ-butyrolacton-2-yl | |
| 1.110 | SMe | SO₂Et | O | γ-butyrolacton-2-yl | |
| 1.111 | SMe | Cl | O | γ-butyrolacton-2-yl | |
| 1.112 | SO₂Me | SO₂Me | O | γ-butyrolacton-2-yl | |
| 1.113 | SO₂Me | SO₂Et | O | γ-butyrolacton-2-yl | |
| 1.114 | SO₂Me | Cl | O | γ-butyrolacton-2-yl | |
| 1.115 | NO₂ | SO₂Me | O | γ-butyrolacton-2-yl | |
| 1.116 | NO₂ | SO₂Et | O | γ-butyrolacton-2-yl | |
| 1.117 | NO₂ | Cl | O | γ-butyrolacton-2-yl | |
| 1.118 | OMe | Cl | O | γ-butyrolacton-2-yl | |
| 1.119 | SO₂Et | Cl | O | γ-butyrolacton-2-yl | |
| 1.120 | SEt | Cl | O | γ-butyrolacton-2-yl | |
| 1.121 | Cl | SO₂Me | S | 3-tetrahydrofuranyl | |
| 1.122 | Cl | SO₂Et | S | 3-tetrahydrofuranyl | |
| 1.123 | Cl | Cl | S | 3-tetrahydrofuranyl | |
| 1.124 | Br | SO₂Me | S | 3-tetrahydrofuranyl | |
| 1.125 | Br | SO₂Et | S | 3-tetrahydrofuranyl | |
| 1.126 | Br | Cl | S | 3-tetrahydrofuranyl | |
| 1.127 | I | SO₂Me | S | 3-tetrahydrofuranyl | |
| 1.128 | I | SO₂Et | S | 3-tetrahydrofuranyl | |
| 1.129 | I | Cl | S | 3-tetrahydrofuranyl | |
| 1.130 | Me | SO₂Me | S | 3-tetrahydrofuranyl | |
| 1.131 | Me | SO₂Et | S | 3-tetrahydrofuranyl | |
| 1.132 | Me | Cl | S | 3-tetrahydrofuranyl | |
| 1.133 | SMe | SO₂Me | S | 3-tetrahydrofuranyl | |
| 1.134 | SMe | SO₂Et | S | 3-tetrahydrofuranyl | |
| 1.135 | SMe | Cl | S | 3-tetrahydrofuranyl | |
| 1.136 | SO₂Me | SO₂Me | S | 3-tetrahydrofuranyl | |
| 1.137 | SO₂Me | SO₂Et | S | 3-tetrahydrofuranyl | |
| 1.138 | SO₂Me | Cl | S | 3-tetrahydrofuranyl | |
| 1.139 | NO₂ | SO₂Me | S | 3-tetrahydrofuranyl | |
| 1.140 | NO₂ | SO₂Et | S | 3-tetrahydrofuranyl | |
| 1.141 | NO₂ | Cl | S | 3-tetrahydrofuranyl | |
| 1.142 | OMe | Cl | S | 3-tetrahydrofuranyl | |
| 1.143 | SO₂Et | Cl | S | 3-tetrahydrofuranyl | |
| 1.144 | SEt | Cl | S | 3-tetrahydrofuranyl | |
| 1.145 | Cl | SO₂Me | S | 4-tetrahydropyranyl | |
| 1.146 | Cl | SO₂Et | S | 4-tetrahydropyranyl | |
| 1.147 | Cl | Cl | S | 4-tetrahydropyranyl | |
| 1.148 | Br | SO₂Me | S | 4-tetrahydropyranyl | |
| 1.149 | Br | SO₂Et | S | 4-tetrahydropyranyl | |
| 1.150 | Br | Cl | S | 4-tetrahydropyranyl | |
| 1.151 | I | SO₂Me | S | 4-tetrahydropyranyl | |
| 1.152 | I | SO₂Et | S | 4-tetrahydropyranyl | |
| 1.153 | I | Cl | S | 4-tetrahydropyranyl | |
| 1.154 | Me | SO₂Me | S | 4-tetrahydropyranyl | |
| 1.155 | Me | SO₂Et | S | 4-tetrahydropyranyl | |
| 1.156 | Me | Cl | S | 4-tetrahydropyranyl | |
| 1.157 | SMe | SO₂Me | S | 4-tetrahydropyranyl | |
| 1.158 | SMe | SO₂Et | S | 4-tetrahydropyranyl | |
| 1.159 | SMe | Cl | S | 4-tetrahydropyranyl | |
| 1.160 | SO₂Me | SO₂Me | S | 4-tetrahydropyranyl | |
| 1.161 | SO₂Me | SO₂Et | S | 4-tetrahydropyranyl | |
| 1.162 | SO₂Me | Cl | S | 4-tetrahydropyranyl | |
| 1.163 | NO₂ | SO₂Me | S | 4-tetrahydropyranyl | |
| 1.164 | NO₂ | SO₂Et | S | 4-tetrahydropyranyl | |
| 1.165 | NO₂ | Cl | S | 4-tetrahydropyranyl | |
| 1.166 | Ome | Cl | S | 4-tetrahydropyranyl | |
| 1.167 | SO₂Et | Cl | S | 4-tetrahydropyranyl | |

TABLE 1-continued

Compounds of the formula (I) according to the invention in which the substituents and symbols are as defined below:
$R^3 = H \; Q = Q1 \; P = 0$

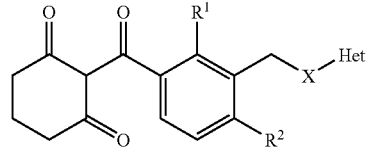

| No. | $R^1$ | $R^2$ | X | Het | Physical Data |
|---|---|---|---|---|---|
| 1.168 | SEt | Cl | S | 4-tetrahydropyranyl | |
| 1.169 | Cl | SO$_2$Me | S | 3-tetrahydropyranyl | |
| 1.170 | Cl | SO$_2$Et | S | 3-tetrahydropyranyl | |
| 1.171 | Cl | Cl | S | 3-tetrahydropyranyl | |
| 1.172 | Br | SO$_2$Me | S | 3-tetrahydropyranyl | |
| 1.173 | Br | SO$_2$Et | S | 3-tetrahydropyranyl | |
| 1.174 | Br | Cl | S | 3-tetrahydropyranyl | |
| 1.175 | I | SO$_2$Me | S | 3-tetrahydropyranyl | |
| 1.176 | I | SO$_2$Et | S | 3-tetrahydropyranyl | |
| 1.177 | I | Cl | S | 3-tetrahydropyranyl | |
| 1.178 | Me | SO$_2$Me | S | 3-tetrahydropyranyl | |
| 1.179 | Me | SO$_2$Et | S | 3-tetrahydropyranyl | |
| 1.180 | Me | Cl | S | 3-tetrahydropyranyl | |
| 1.181 | SMe | SO$_2$Me | S | 3-tetrahydropyranyl | |
| 1.182 | SMe | SO$_2$Et | S | 3-tetrahydropyranyl | |
| 1.183 | SMe | Cl | S | 3-tetrahydropyranyl | |
| 1.184 | SO$_2$Me | SO$_2$Me | S | 3-tetrahydropyranyl | |
| 1.185 | SO$_2$Me | SO$_2$Et | S | 3-tetrahydropyranyl | |
| 1.186 | SO$_2$Me | Cl | S | 3-tetrahydropyranyl | |
| 1.187 | NO$_2$ | SO$_2$Me | S | 3-tetrahydropyranyl | |
| 1.188 | NO$_2$ | SO$_2$Et | S | 3-tetrahydropyranyl | |
| 1.189 | NO$_2$ | Cl | S | 3-tetrahydropyranyl | |
| 1.190 | OMe | Cl | S | 3-tetrahydropyranyl | |
| 1.191 | SO$_2$Et | Cl | S | 3-tetrahydropyranyl | |
| 1.192 | SEt | Cl | S | 3-tetrahydropyranyl | |
| 1.193 | Cl | SO$_2$Me | S | 1,3-dioxan-5-yl | |
| 1.194 | Cl | SO$_2$Et | S | 1,3-dioxan-5-yl | |
| 1.195 | Cl | Cl | S | 1,3-dioxan-5-yl | |
| 1.196 | Br | SO$_2$Me | S | 1,3-dioxan-5-yl | |
| 1.197 | Br | SO$_2$Et | S | 1,3-dioxan-5-yl | |
| 1.198 | Br | Cl | S | 1,3-dioxan-5-yl | |
| 1.199 | I | SO$_2$Me | S | 1,3-dioxan-5-yl | |
| 1.200 | I | SO$_2$Et | S | 1,3-dioxan-5-yl | |
| 1.201 | I | Cl | S | 1,3-dioxan-5-yl | |
| 1.202 | Me | SO$_2$Me | S | 1,3-dioxan-5-yl | |
| 1.203 | Me | SO$_2$Et | S | 1,3-dioxan-5-yl | |
| 1.204 | Me | Cl | S | 1,3-dioxan-5-yl | |
| 1.205 | SMe | SO$_2$Me | S | 1,3-dioxan-5-yl | |
| 1.206 | SMe | SO$_2$Et | S | 1,3-dioxan-5-yl | |
| 1.207 | SMe | Cl | S | 1,3-dioxan-5-yl | |
| 1.208 | SO$_2$Me | SO$_2$Me | S | 1,3-dioxan-5-yl | |
| 1.209 | SO$_2$Me | SO$_2$Et | S | 1,3-dioxan-5-yl | |
| 1.210 | SO$_2$Me | Cl | S | 1,3-dioxan-5-yl | |
| 1.211 | NO$_2$ | SO$_2$Me | S | 1,3-dioxan-5-yl | |
| 1.212 | NO$_2$ | SO$_2$Et | S | 1,3-dioxan-5-yl | |
| 1.213 | NO$_2$ | Cl | S | 1,3-dioxan-5-yl | |
| 1.214 | OMe | Cl | S | 1,3-dioxan-5-yl | |
| 1.215 | SO$_2$Et | Cl | S | 1,3-dioxan-5-yl | |
| 1.216 | SEt | Cl | S | 1,3-dioxan-5-yl | |
| 1.217 | Cl | SO$_2$Me | S | γ-butyrolacton-2-yl | |
| 1.218 | Cl | SO$_2$Et | S | γ-butyrolacton-2-yl | |
| 1.219 | Cl | Cl | S | γ-butyrolacton-2-yl | |
| 1.220 | Br | SO$_2$Me | S | γ-butyrolacton-2-yl | |
| 1.221 | Br | SO$_2$Et | S | γ-butyrolacton-2-yl | |
| 1.222 | Br | Cl | S | γ-butyrolacton-2-yl | |
| 1.223 | I | SO$_2$Me | S | γ-butyrolacton-2-yl | |
| 1.224 | I | SO$_2$Et | S | γ-butyrolacton-2-yl | |
| 1.225 | I | Cl | S | γ-butyrolacton-2-yl | |
| 1.226 | Me | SO$_2$Me | S | γ-butyrolacton-2-yl | |
| 1.227 | Me | SO$_2$Et | S | γ-butyrolacton-2-yl | |
| 1.228 | Me | Cl | S | γ-butyrolacton-2-yl | |
| 1.229 | SMe | SO$_2$Me | S | γ-butyrolacton-2-yl | |
| 1.220 | SMe | SO$_2$Et | S | γ-butyrolacton-2-yl | |
| 1.231 | SMe | Cl | S | γ-butyrolacton-2-yl | |
| 1.232 | SO$_2$Me | SO$_2$Me | S | γ-butyrolacton-2-yl | |
| 1.233 | SO$_2$Me | SO$_2$Et | S | γ-butyrolacton-2-yl | |
| 1.234 | SO$_2$Me | Cl | S | γ-butyrolacton-2-yl | |
| 1.235 | NO$_2$ | SO$_2$Me | S | γ-butyrolacton-2-yl | |
| 1.236 | NO$_2$ | SO$_2$Et | S | γ-butyrolacton-2-yl | |
| 1.237 | NO$_2$ | Cl | S | γ-butyrolacton-2-yl | |
| 1.238 | OMe | Cl | S | γ-butyrolacton-2-yl | |
| 1.239 | SO$_2$Et | Cl | S | γ-butyrolacton-2-yl | |
| 1.240 | SEt | Cl | S | γ-butyrolacton-2-yl | |
| 1.241 | OEt | Cl | O | 3-tetrahydrofuranyl | oil, Rf = 0.4 (EA) |

TABLE 2

Compounds of the formula (I) according to the invention in which the substituents and symbols are as defined below:
$R^3 = H \; Q = Q1 \; p = 2$

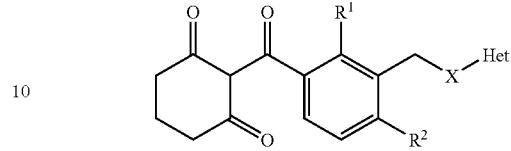

| No. | $R^1$ | $R^2$ | X | Het | Physical Data |
|---|---|---|---|---|---|
| 2.1 | Cl | SO$_2$Me | O | 3-tetrahydrofuranyl | oil, Rf = 0.2 (EA) |
| 2.2 | Cl | SO$_2$Et | O | 3-tetrahydrofuranyl | oil, Rf = 0.4 (EA) |
| 2.3 | Cl | Cl | O | 3-tetrahydrofuranyl | |
| 2.4 | Br | SO$_2$Me | O | 3-tetrahydrofuranyl | |
| 2.5 | Br | SO$_2$Et | O | 3-tetrahydrofuranyl | |
| 2.6 | Br | Cl | O | 3-tetrahydrofuranyl | |
| 2.7 | I | SO$_2$Me | O | 3-tetrahydrofuranyl | |
| 2.8 | I | SO$_2$Et | O | 3-tetrahydrofuranyl | |
| 2.9 | I | Cl | O | 3-tetrahydrofuranyl | |
| 2.10 | Me | SO$_2$Me | O | 3-tetrahydrofuranyl | |
| 2.11 | Me | SO$_2$Et | O | 3-tetrahydrofuranyl | |
| 2.12 | Me | Cl | O | 3-tetrahydrofuranyl | |
| 2.13 | SMe | SO$_2$Me | O | 3-tetrahydrofuranyl | |
| 2.14 | SMe | SO$_2$Et | O | 3-tetrahydrofuranyl | |
| 2.15 | SMe | Cl | O | 3-tetrahydrofuranyl | |
| 2.16 | SO$_2$Me | SO$_2$Me | O | 3-tetrahydrofuranyl | |
| 2.17 | SO$_2$Me | SO$_2$Et | O | 3-tetrahydrofuranyl | |
| 2.18 | SO$_2$Me | Cl | O | 3-tetrahydrofuranyl | |
| 2.19 | NO$_2$ | SO$_2$Me | O | 3-tetrahydrofuranyl | |
| 2.20 | NO$_2$ | SO$_2$Et | O | 3-tetrahydrofuranyl | |
| 2.21 | NO$_2$ | Cl | O | 3-tetrahydrofuranyl | |
| 2.22 | Cl | SO$_2$Me | O | 4-tetrahydropyranyl | |
| 2.23 | Cl | SO$_2$Et | O | 4-tetrahydropyranyl | |
| 2.24 | Cl | Cl | O | 4-tetrahydropyranyl | |
| 2.25 | Br | SO$_2$Me | O | 4-tetrahydropyranyl | |
| 2.26 | Br | SO$_2$Et | O | 4-tetrahydropyranyl | |
| 2.27 | Br | Cl | O | 4-tetrahydropyranyl | |
| 2.28 | I | SO$_2$Me | O | 4-tetrahydropyranyl | |
| 2.29 | I | SO$_2$Et | O | 4-tetrahydropyranyl | |
| 2.30 | I | Cl | O | 4-tetrahydropyranyl | |
| 2.31 | Me | SO$_2$Me | O | 4-tetrahydropyranyl | |
| 2.32 | Me | SO$_2$Et | O | 4-tetrahydropyranyl | |
| 2.33 | Me | Cl | O | 4-tetrahydropyranyl | |
| 2.34 | SMe | SO$_2$Me | O | 4-tetrahydropyranyl | |

TABLE 2-continued

Compounds of the formula (I) according to the invention in which the substituents and symbols are as defined below:
$R^3 = H$  $Q = Q1$  $p = 2$

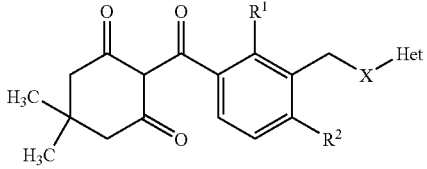

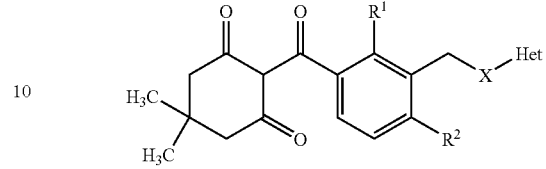

| No. | $R^1$ | $R^2$ | X | Het | Physical Data |
|---|---|---|---|---|---|
| 2.35 | SMe | SO$_2$Et | O | 4-tetrahydropyranyl | |
| 2.36 | SMe | Cl | O | 4-tetrahydropyranyl | |
| 2.37 | SO$_2$Me | SO$_2$Me | O | 4-tetrahydropyranyl | |
| 2.38 | SO$_2$Me | SO$_2$Et | O | 4-tetrahydropyranyl | |
| 2.39 | SO$_2$Me | Cl | O | 4-tetrahydropyranyl | |
| 2.40 | NO$_2$ | SO$_2$Me | O | 4-tetrahydropyranyl | |
| 2.41 | NO$_2$ | SO$_2$Et | O | 4-tetrahydropyranyl | |
| 2.42 | NO$_2$ | Cl | O | 4-tetrahydropyranyl | |
| 2.43 | Cl | SO$_2$Me | O | 3-tetrahydropyranyl | |
| 2.44 | Cl | SO$_2$Et | O | 3-tetrahydropyranyl | |
| 2.45 | Cl | Cl | O | 3-tetrahydropyranyl | |
| 2.46 | Br | SO$_2$Me | O | 3-tetrahydropyranyl | |
| 2.47 | Br | SO$_2$Et | O | 3-tetrahydropyranyl | |
| 2.48 | Br | Cl | O | 3-tetrahydropyranyl | |
| 2.49 | I | SO$_2$Me | O | 3-tetrahydropyranyl | |
| 2.50 | I | SO$_2$Et | O | 3-tetrahydropyranyl | |
| 2.51 | I | Cl | O | 3-tetrahydropyranyl | |
| 2.52 | Me | SO$_2$Me | O | 3-tetrahydropyranyl | |
| 2.53 | Me | SO$_2$Et | O | 3-tetrahydropyranyl | |
| 2.54 | Me | Cl | O | 3-tetrahydropyranyl | |
| 2.55 | SMe | SO$_2$Me | O | 3-tetrahydropyranyl | |
| 2.56 | SMe | SO$_2$Et | O | 3-tetrahydropyranyl | |
| 2.57 | SMe | Cl | O | 3-tetrahydropyranyl | |
| 2.58 | SO$_2$Me | SO$_2$Me | O | 3-tetrahydropyranyl | |
| 2.59 | SO$_2$Me | SO$_2$Et | O | 3-tetrahydropyranyl | |
| 2.60 | SO$_2$Me | Cl | O | 3-tetrahydropyranyl | |
| 2.61 | NO$_2$ | SO$_2$Me | O | 3-tetrahydropyranyl | |
| 2.62 | NO$_2$ | SO$_2$Et | O | 3-tetrahydropyranyl | |
| 2.63 | NO$_2$ | Cl | O | 3-tetrahydropyranyl | |
| 2.64 | Cl | SO$_2$Me | O | 1,3-dioxan-5-yl | |
| 2.65 | Cl | SO$_2$Et | O | 1,3-dioxan-5-yl | |
| 2.66 | Cl | Cl | O | 1,3-dioxan-5-yl | |
| 2.67 | Br | SO$_2$Me | O | 1,3-dioxan-5-yl | |
| 2.68 | Br | SO$_2$Et | O | 1,3-dioxan-5-yl | |
| 2.69 | Br | Cl | O | 1,3-dioxan-5-yl | |
| 2.70 | I | SO$_2$Me | O | 1,3-dioxan-5-yl | |
| 2.71 | I | SO$_2$Et | O | 1,3-dioxan-5-yl | |
| 2.72 | I | Cl | O | 1,3-dioxan-5-yl | |
| 2.73 | Me | SO$_2$Me | O | 1,3-dioxan-5-yl | |
| 2.74 | Me | SO$_2$Et | O | 1,3-dioxan-5-yl | |
| 2.75 | Me | Cl | O | 1,3-dioxan-5-yl | |
| 2.76 | SMe | SO$_2$Me | O | 1,3-dioxan-5-yl | |
| 2.77 | SMe | SO$_2$Et | O | 1,3-dioxan-5-yl | |
| 2.78 | SMe | Cl | O | 1,3-dioxan-5-yl | |
| 2.79 | SO$_2$Me | SO$_2$Me | O | 1,3-dioxan-5-yl | |
| 2.80 | SO$_2$Me | SO$_2$Et | O | 1,3-dioxan-5-yl | |
| 2.81 | SO$_2$Me | Cl | O | 1,3-dioxan-5-yl | |
| 2.82 | NO$_2$ | SO$_2$Me | O | 1,3-dioxan-5-yl | |
| 2.83 | NO$_2$ | SO$_2$Et | O | 1,3-dioxan-5-yl | |
| 2.84 | NO$_2$ | Cl | O | 1,3-dioxan-5-yl | |
| 2.85 | Cl | SO$_2$Me | O | γ-butyrolacton-2-yl | |
| 2.86 | Cl | SO$_2$Et | O | γ-butyrolacton-2-yl | |
| 2.87 | Cl | Cl | O | γ-butyrolacton-2-yl | |
| 2.88 | Br | SO$_2$Me | O | γ-butyrolacton-2-yl | |
| 2.89 | Br | SO$_2$Et | O | γ-butyrolacton-2-yl | |
| 2.90 | Br | Cl | O | γ-butyrolacton-2-yl | |
| 2.91 | I | SO$_2$Me | O | γ-butyrolacton-2-yl | |
| 2.92 | I | SO$_2$Et | O | γ-butyrolacton-2-yl | |
| 2.93 | I | Cl | O | γ-butyrolacton-2-yl | |
| 2.94 | Me | SO$_2$Me | O | γ-butyrolacton-2-yl | |
| 2.95 | Me | SO$_2$Et | O | γ-butyrolacton-2-yl | |
| 2.96 | Me | Cl | O | γ-butyrolacton-2-yl | |
| 2.97 | SMe | SO$_2$Me | O | γ-butyrolacton-2-yl | |
| 2.98 | SMe | SO$_2$Et | O | γ-butyrolacton-2-yl | |
| 2.99 | SMe | Cl | O | γ-butyrolacton-2-yl | |
| 2.100 | SO$_2$Me | SO$_2$Me | O | γ-butyrolacton-2-yl | |
| 2.101 | SO$_2$Me | SO$_2$Et | O | γ-butyrolacton-2-yl | |
| 2.102 | SO$_2$Me | Cl | O | γ-butyrolacton-2-yl | |
| 2.103 | NO$_2$ | SO$_2$Me | O | γ-butyrolacton-2-yl | |
| 2.104 | NO$_2$ | SO$_2$Et | O | γ-butyrolacton-2-yl | |
| 2.105 | NO$_2$ | Cl | O | γ-butyrolacton-2-yl | |
| 2.106 | Cl | SO$_2$Me | S | 3-tetrahydrofuranyl | |
| 2.107 | Cl | SO$_2$Et | S | 3-tetrahydrofuranyl | |
| 2.108 | Cl | Cl | S | 3-tetrahydrofuranyl | |
| 2.109 | Br | SO$_2$Me | S | 3-tetrahydrofuranyl | |
| 2.110 | Br | SO$_2$Et | S | 3-tetrahydrofuranyl | |
| 2.111 | Br | Cl | S | 3-tetrahydrofuranyl | |
| 2.112 | I | SO$_2$Me | S | 3-tetrahydrofuranyl | |
| 2.113 | I | SO$_2$Et | S | 3-tetrahydrofuranyl | |
| 2.114 | I | Cl | S | 3-tetrahydrofuranyl | |
| 2.115 | Me | SO$_2$Me | S | 3-tetrahydrofuranyl | |
| 2.116 | Me | SO$_2$Et | S | 3-tetrahydrofuranyl | |
| 2.117 | Me | Cl | S | 3-tetrahydrofuranyl | |
| 2.118 | SMe | SO$_2$Me | S | 3-tetrahydrofuranyl | |
| 2.119 | SMe | SO$_2$Et | S | 3-tetrahydrofuranyl | |
| 2.120 | SMe | Cl | S | 3-tetrahydrofuranyl | |
| 2.121 | SO$_2$Me | SO$_2$Me | S | 3-tetrahydrofuranyl | |
| 2.122 | SO$_2$Me | SO$_2$Et | S | 3-tetrahydrofuranyl | |
| 2.123 | SO$_2$Me | Cl | S | 3-tetrahydrofuranyl | |
| 2.124 | NO$_2$ | SO$_2$Me | S | 3-tetrahydrofuranyl | |
| 2.125 | NO$_2$ | SO$_2$Et | S | 3-tetrahydrofuranyl | |
| 2.126 | NO$_2$ | Cl | S | 3-tetrahydrofuranyl | |
| 2.127 | Cl | SO$_2$Me | S | 4-tetrahydropyranyl | |
| 2.128 | Cl | SO$_2$Et | S | 4-tetrahydropyranyl | |
| 2.129 | Cl | Cl | S | 4-tetrahydropyranyl | |
| 2.130 | Br | SO$_2$Me | S | 4-tetrahydropyranyl | |
| 2.131 | Br | SO$_2$Et | S | 4-tetrahydropyranyl | |
| 2.132 | Br | Cl | S | 4-tetrahydropyranyl | |
| 2.133 | I | SO$_2$Me | S | 4-tetrahydropyranyl | |
| 2.134 | I | SO$_2$Et | S | 4-tetrahydropyranyl | |
| 2.135 | I | Cl | S | 4-tetrahydropyranyl | |
| 2.136 | Me | SO$_2$Me | S | 4-tetrahydropyranyl | |
| 2.137 | Me | SO$_2$Et | S | 4-tetrahydropyranyl | |
| 2.138 | Me | Cl | S | 4-tetrahydropyranyl | |
| 2.139 | SMe | SO$_2$Me | S | 4-tetrahydropyranyl | |
| 2.140 | SMe | SO$_2$Et | S | 4-tetrahydropyranyl | |
| 2.141 | SMe | Cl | S | 4-tetrahydropyranyl | |
| 2.142 | SO$_2$Me | SO$_2$Me | S | 4-tetrahydropyranyl | |
| 2.143 | SO$_2$Me | SO$_2$Et | S | 4-tetrahydropyranyl | |
| 2.144 | SO$_2$Me | Cl | S | 4-tetrahydropyranyl | |
| 2.145 | NO$_2$ | SO$_2$Me | S | 4-tetrahydropyranyl | |
| 2.146 | NO$_2$ | SO$_2$Et | S | 4-tetrahydropyranyl | |
| 2.147 | NO$_2$ | Cl | S | 4-tetrahydropyranyl | |
| 2.148 | Cl | SO$_2$Me | S | 3-tetrahydropyranyl | |
| 2.149 | Cl | SO$_2$Et | S | 3-tetrahydropyranyl | |
| 2.150 | Cl | Cl | S | 3-tetrahydropyranyl | |
| 2.151 | Br | SO$_2$Me | S | 3-tetrahydropyranyl | |
| 2.152 | Br | SO$_2$Et | S | 3-tetrahydropyranyl | |
| 2.153 | Br | Cl | S | 3-tetrahydropyranyl | |
| 2.154 | I | SO$_2$Me | S | 3-tetrahydropyranyl | |
| 2.155 | I | SO$_2$Et | S | 3-tetrahydropyranyl | |
| 2.156 | I | Cl | S | 3-tetrahydropyranyl | |
| 2.157 | Me | SO$_2$Me | S | 3-tetrahydropyranyl | |
| 2.158 | Me | SO$_2$Et | S | 3-tetrahydropyranyl | |
| 2.159 | Me | Cl | S | 3-tetrahydropyranyl | |
| 2.160 | SMe | SO$_2$Me | S | 3-tetrahydropyranyl | |

TABLE 2-continued

Compounds of the formula (I) according to the invention in which the substituents and symbols are as defined below:
R³ = H  Q = Q1  p = 2

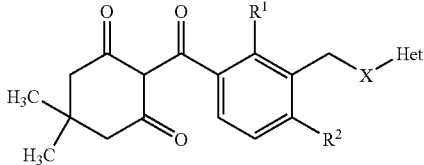

| No. | R¹ | R² | X | Het | Physical Data |
|---|---|---|---|---|---|
| 2.161 | SMe | SO₂Et | S | 3-tetrahydropyranyl | |
| 2.162 | SMe | Cl | S | 3-tetrahydropyranyl | |
| 2.163 | SO₂Me | SO₂Me | S | 3-tetrahydropyranyl | |
| 2.164 | SO₂Me | SO₂Et | S | 3-tetrahydropyranyl | |
| 2.165 | SO₂Me | Cl | S | 3-tetrahydropyranyl | |
| 2.166 | NO₂ | SO₂Me | S | 3-tetrahydropyranyl | |
| 2.167 | NO₂ | SO₂Et | S | 3-tetrahydropyranyl | |
| 2.168 | NO₂ | Cl | S | 3-tetrahydropyranyl | |
| 2.169 | Cl | SO₂Me | S | 1,3-dioxan-5-yl | |
| 2.170 | Cl | SO₂Et | S | 1,3-dioxan-5-yl | |
| 2.171 | Cl | Cl | S | 1,3-dioxan-5-yl | |
| 2.172 | Br | SO₂Me | S | 1,3-dioxan-5-yl | |
| 2.173 | Br | SO₂Et | S | 1,3-dioxan-5-yl | |
| 2.174 | Br | Cl | S | 1,3-dioxan-5-yl | |
| 2.175 | I | SO₂Me | S | 1,3-dioxan-5-yl | |
| 2.176 | I | SO₂Et | S | 1,3-dioxan-5-yl | |
| 2.177 | I | Cl | S | 1,3-dioxan-5-yl | |
| 2.178 | Me | SO₂Me | S | 1,3-dioxan-5-yl | |
| 2.179 | Me | SO₂Et | S | 1,3-dioxan-5-yl | |
| 2.180 | Me | Cl | S | 1,3-dioxan-5-yl | |
| 2.181 | SMe | SO₂Me | S | 1,3-dioxan-5-yl | |
| 2.182 | SMe | SO₂Et | S | 1,3-dioxan-5-yl | |
| 2.183 | SMe | Cl | S | 1,3-dioxan-5-yl | |
| 2.184 | SO₂Me | SO₂Me | S | 1,3-dioxan-5-yl | |
| 2.185 | SO₂Me | SO₂Et | S | 1,3-dioxan-5-yl | |
| 2.186 | SO₂Me | Cl | S | 1,3-dioxan-5-yl | |
| 2.187 | NO₂ | SO₂Me | S | 1,3-dioxan-5-yl | |
| 2.188 | NO₂ | SO₂Et | S | 1,3-dioxan-5-yl | |
| 2.189 | NO₂ | Cl | S | 1,3-dioxan-5-yl | |
| 2.190 | Cl | SO₂Me | S | γ-butyrolacton-2-yl | |
| 2.191 | Cl | SO₂Et | S | γ-butyrolacton-2-yl | |
| 2.192 | Cl | Cl | S | γ-butyrolacton-2-yl | |
| 2.193 | Br | SO₂Me | S | γ-butyrolacton-2-yl | |
| 2.194 | Br | SO₂Et | S | γ-butyrolacton-2-yl | |
| 2.195 | Br | Cl | S | γ-butyrolacton-2-yl | |
| 2.196 | I | SO₂Me | S | γ-butyrolacton-2-yl | |
| 2.197 | I | SO₂Et | S | γ-butyrolacton-2-yl | |
| 2.198 | I | Cl | S | γ-butyrolacton-2-yl | |
| 2.199 | Me | SO₂Me | S | γ-butyrolacton-2-yl | |
| 2.200 | Me | SO₂Et | S | γ-butyrolacton-2-yl | |
| 2.201 | Me | Cl | S | γ-butyrolacton-2-yl | |
| 2.202 | SMe | SO₂Me | S | γ-butyrolacton-2-yl | |
| 2.203 | SMe | SO₂Et | S | γ-butyrolacton-2-yl | |
| 2.204 | SMe | Cl | S | γ-butyrolacton-2-yl | |
| 2.205 | SO₂Me | SO₂Me | S | γ-butyrolacton-2-yl | |
| 2.206 | SO₂Me | SO₂Et | S | γ-butyrolacton-2-yl | |
| 2.207 | SO₂Me | Cl | S | γ-butyrolacton-2-yl | |
| 2.208 | NO₂ | SO₂Me | S | γ-butyrolacton-2-yl | |
| 2.209 | NO₂ | SO₂Et | S | γ-butyrolacton-2-yl | |
| 2.210 | NO₂ | Cl | S | γ-butyrolacton-2-yl | |
| 2.211 | SEt | Cl | S | 3-tetrahydrofuranyl | |
| 2.212 | SEt | Cl | S | 3-tetrahydropyranyl | |
| 2.213 | SEt | Cl | S | 4-tetrahydropyranyl | |
| 2.214 | SEt | Cl | S | 1,3-dioxan-5-yl | |
| 2.215 | SEt | Cl | S | γ-butyrolacton-2-yl | |
| 2.216 | SO₂Et | Cl | S | 3-tetrahydrofuranyl | |
| 2.217 | SO₂Et | Cl | S | 3-tetrahydropyranyl | |
| 2.218 | SO₂Et | Cl | S | 4-tetrahydropyranyl | |
| 2.219 | SO₂Et | Cl | S | 1,3-dioxan-5-yl | |
| 2.220 | SO₂Et | Cl | S | γ-butyrolacton-2-yl | |
| 2.221 | OMe | Cl | S | 3-tetrahydrofuranyl | |
| 2.222 | OMe | Cl | S | 3-tetrahydropyranyl | |
| 2.223 | OMe | Cl | S | 4-tetrahydropyranyl | |

TABLE 2-continued

Compounds of the formula (I) according to the invention in which the substituents and symbols are as defined below:
R³ = H  Q = Q1  p = 2

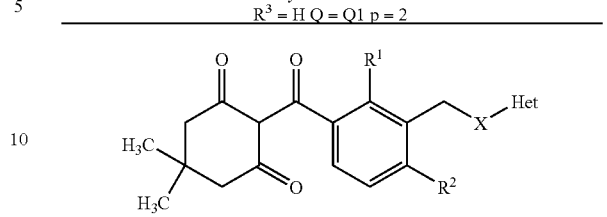

| No. | R¹ | R² | X | Het | Physical Data |
|---|---|---|---|---|---|
| 2.224 | OMe | Cl | S | 1,3-dioxan-5-yl | |
| 2.225 | OMe | Cl | S | γ-butyrolacton-2-yl | |

TABLE 3

Compounds of the formula (I) according to the invention in which the substituents and symbols are as defined below:
R³ = H  Q = Q1  p = 2

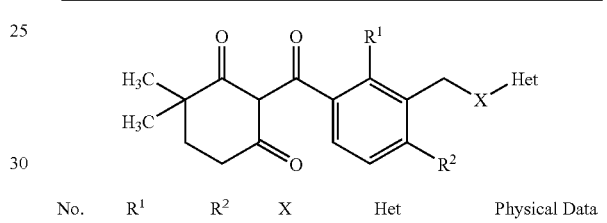

| No. | R¹ | R² | X | Het | Physical Data |
|---|---|---|---|---|---|
| 3.1 | Cl | SO₂Me | O | 3-tetrahydrofuranyl | oil, Rf = 0.2 (EA) |
| 3.2 | Cl | SO₂Et | O | 3-tetrahydrofuranyl | oil, Rf = 0.2 (EA) |
| 3.3 | Cl | Cl | O | 3-tetrahydrofuranyl | |
| 3.4 | Br | SO₂Me | O | 3-tetrahydrofuranyl | |
| 3.5 | Br | SO₂Et | O | 3-tetrahydrofuranyl | |
| 3.6 | Br | Cl | O | 3-tetrahydrofuranyl | |
| 3.7 | I | SO₂Me | O | 3-tetrahydrofuranyl | |
| 3.8 | I | SO₂Et | O | 3-tetrahydrofuranyl | |
| 3.9 | I | Cl | O | 3-tetrahydrofuranyl | |
| 3.10 | Me | SO₂Me | O | 3-tetrahydrofuranyl | |
| 3.11 | Me | SO₂Et | O | 3-tetrahydrofuranyl | |
| 3.12 | Me | Cl | O | 3-tetrahydrofuranyl | |
| 3.13 | SMe | SO₂Me | O | 3-tetrahydrofuranyl | |
| 3.14 | SMe | SO₂Et | O | 3-tetrahydrofuranyl | |
| 3.15 | SMe | Cl | O | 3-tetrahydrofuranyl | |
| 3.16 | SO₂Me | SO₂Me | O | 3-tetrahydrofuranyl | |
| 3.17 | SO₂Me | SO₂Et | O | 3-tetrahydrofuranyl | |
| 3.18 | SO₂Me | Cl | O | 3-tetrahydrofuranyl | |
| 3.19 | NO₂ | SO₂Me | O | 3-tetrahydrofuranyl | |
| 3.20 | NO₂ | SO₂Et | O | 3-tetrahydrofuranyl | |
| 3.21 | NO₂ | Cl | O | 3-tetrahydrofuranyl | |
| 3.22 | Cl | SO₂Me | O | 4-tetrahydropyranyl | |
| 3.23 | Cl | SO₂Et | O | 4-tetrahydropyranyl | |
| 3.24 | Cl | Cl | O | 4-tetrahydropyranyl | |
| 3.25 | Br | SO₂Me | O | 4-tetrahydropyranyl | |
| 3.26 | Br | SO₂Et | O | 4-tetrahydropyranyl | |
| 3.27 | Br | Cl | O | 4-tetrahydropyranyl | |
| 3.28 | I | SO₂Me | O | 4-tetrahydropyranyl | |
| 3.29 | I | SO₂Et | O | 4-tetrahydropyranyl | |
| 3.30 | I | Cl | O | 4-tetrahydropyranyl | |
| 3.31 | Me | SO₂Me | O | 4-tetrahydropyranyl | |
| 3.32 | Me | SO₂Et | O | 4-tetrahydropyranyl | |
| 3.33 | Me | Cl | O | 4-tetrahydropyranyl | |
| 3.34 | SMe | SO₂Me | O | 4-tetrahydropyranyl | |
| 3.35 | SMe | SO₂Et | O | 4-tetrahydropyranyl | |
| 3.36 | SMe | Cl | O | 4-tetrahydropyranyl | |
| 3.37 | SO₂Me | SO₂Me | O | 4-tetrahydropyranyl | |
| 3.38 | SO₂Me | SO₂Et | O | 4-tetrahydropyranyl | |
| 3.39 | SO₂Me | Cl | O | 4-tetrahydropyranyl | |
| 3.40 | NO₂ | SO₂Me | O | 4-tetrahydropyranyl | |
| 3.41 | NO₂ | SO₂Et | O | 4-tetrahydropyranyl | |
| 3.42 | NO₂ | Cl | O | 4-tetrahydropyranyl | |

TABLE 3-continued

Compounds of the formula (I) according to the invention in which the substituents and symbols are as defined below:
R³ = H  Q = Q1  p = 2

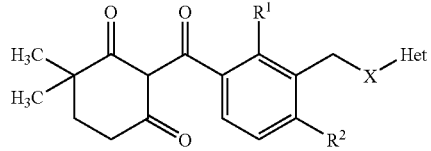

| No. | R¹ | R² | X | Het | Physical Data |
|---|---|---|---|---|---|
| 3.43 | Cl | SO$_2$Me | O | 3-tetrahydropyranyl | |
| 3.44 | Cl | SO$_2$Et | O | 3-tetrahydropyranyl | |
| 3.45 | Cl | Cl | O | 3-tetrahydropyranyl | |
| 3.46 | Br | SO$_2$Me | O | 3-tetrahydropyranyl | |
| 3.47 | Br | SO$_2$Et | O | 3-tetrahydropyranyl | |
| 3.48 | Br | Cl | O | 3-tetrahydropyranyl | |
| 3.49 | I | SO$_2$Me | O | 3-tetrahydropyranyl | |
| 3.50 | I | SO$_2$Et | O | 3-tetrahydropyranyl | |
| 3.51 | I | Cl | O | 3-tetrahydropyranyl | |
| 3.52 | Me | SO$_2$Me | O | 3-tetrahydropyranyl | |
| 3.53 | Me | SO$_2$Et | O | 3-tetrahydropyranyl | |
| 3.54 | Me | Cl | O | 3-tetrahydropyranyl | |
| 3.55 | SMe | SO$_2$Me | O | 3-tetrahydropyranyl | |
| 3.56 | SMe | SO$_2$Et | O | 3-tetrahydropyranyl | |
| 3.57 | SMe | Cl | O | 3-tetrahydropyranyl | |
| 3.58 | SO$_2$Me | SO$_2$Me | O | 3-tetrahydropyranyl | |
| 3.59 | SO$_2$Me | SO$_2$Et | O | 3-tetrahydropyranyl | |
| 3.60 | SO$_2$Me | Cl | O | 3-tetrahydropyranyl | |
| 3.61 | NO$_2$ | SO$_2$Me | O | 3-tetrahydropyranyl | |
| 3.62 | NO$_2$ | SO$_2$Et | O | 3-tetrahydropyranyl | |
| 3.63 | NO$_2$ | Cl | O | 3-tetrahydropyranyl | |
| 3.64 | Cl | SO$_2$Me | O | 1,3-dioxan-5-yl | |
| 3.65 | Cl | SO$_2$Et | O | 1,3-dioxan-5-yl | |
| 3.66 | Cl | Cl | O | 1,3-dioxan-5-yl | |
| 3.67 | Br | SO$_2$Me | O | 1,3-dioxan-5-yl | |
| 3.68 | Br | SO$_2$Et | O | 1,3-dioxan-5-yl | |
| 3.69 | Br | Cl | O | 1,3-dioxan-5-yl | |
| 3.70 | I | SO$_2$Me | O | 1,3-dioxan-5-yl | |
| 3.71 | I | SO$_2$Et | O | 1,3-dioxan-5-yl | |
| 3.72 | I | Cl | O | 1,3-dioxan-5-yl | |
| 3.73 | Me | SO$_2$Me | O | 1,3-dioxan-5-yl | |
| 3.74 | Me | SO$_2$Et | O | 1,3-dioxan-5-yl | |
| 3.75 | Me | Cl | O | 1,3-dioxan-5-yl | |
| 3.76 | SMe | SO$_2$Me | O | 1,3-dioxan-5-yl | |
| 3.77 | SMe | SO$_2$Et | O | 1,3-dioxan-5-yl | |
| 3.78 | SMe | Cl | O | 1,3-dioxan-5-yl | |
| 3.79 | SO$_2$Me | SO$_2$Me | O | 1,3-dioxan-5-yl | |
| 3.80 | SO$_2$Me | SO$_2$Et | O | 1,3-dioxan-5-yl | |
| 3.81 | SO$_2$Me | Cl | O | 1,3-dioxan-5-yl | |
| 3.82 | NO$_2$ | SO$_2$Me | O | 1,3-dioxan-5-yl | |
| 3.83 | NO$_2$ | SO$_2$Et | O | 1,3-dioxan-5-yl | |
| 3.84 | NO$_2$ | Cl | O | 1,3-dioxan-5-yl | |
| 3.85 | Cl | SO$_2$Me | O | γ-butyrolacton-2-yl | |
| 3.86 | Cl | SO$_2$Et | O | γ-butyrolacton-2-yl | |
| 3.87 | Cl | Cl | O | γ-butyrolacton-2-yl | |
| 3.88 | Br | SO$_2$Me | O | γ-butyrolacton-2-yl | |
| 3.89 | Br | SO$_2$Et | O | γ-butyrolacton-2-yl | |
| 3.90 | Br | Cl | O | γ-butyrolacton-2-yl | |
| 3.91 | I | SO$_2$Me | O | γ-butyrolacton-2-yl | |
| 3.92 | I | SO$_2$Et | O | γ-butyrolacton-2-yl | |
| 3.93 | I | Cl | O | γ-butyrolacton-2-yl | |
| 3.94 | Me | SO$_2$Me | O | γ-butyrolacton-2-yl | |
| 3.95 | Me | SO$_2$Et | O | γ-butyrolacton-2-yl | |
| 3.96 | Me | Cl | O | γ-butyrolacton-2-yl | |
| 3.97 | SMe | SO$_2$Me | O | γ-butyrolacton-2-yl | |
| 3.98 | SMe | SO$_2$Et | O | γ-butyrolacton-2-yl | |
| 3.99 | SMe | Cl | O | γ-butyrolacton-2-yl | |
| 3.100 | SO$_2$Me | SO$_2$Me | O | γ-butyrolacton-2-yl | |
| 3.101 | SO$_2$Me | SO$_2$Et | O | γ-butyrolacton-2-yl | |
| 3.102 | SO$_2$Me | Cl | O | γ-butyrolacton-2-yl | |
| 3.103 | NO$_2$ | SO$_2$Me | O | γ-butyrolacton-2-yl | |
| 3.104 | NO$_2$ | SO$_2$Et | O | γ-butyrolacton-2-yl | |
| 3.105 | NO$_2$ | Cl | O | γ-butyrolacton-2-yl | |
| 3.106 | Cl | SO$_2$Me | S | 3-tetrahydrofuranyl | |
| 3.107 | Cl | SO$_2$Et | S | 3-tetrahydrofuranyl | |
| 3.108 | Cl | Cl | S | 3-tetrahydrofuranyl | |
| 3.109 | Br | SO$_2$Me | S | 3-tetrahydrofuranyl | |
| 3.110 | Br | SO$_2$Et | S | 3-tetrahydrofuranyl | |
| 3.111 | Br | Cl | S | 3-tetrahydrofuranyl | |
| 3.112 | I | SO$_2$Me | S | 3-tetrahydrofuranyl | |
| 3.113 | I | SO$_2$Et | S | 3-tetrahydrofuranyl | |
| 3.114 | I | Cl | S | 3-tetrahydrofuranyl | |
| 3.115 | Me | SO$_2$Me | S | 3-tetrahydrofuranyl | |
| 3.116 | Me | SO$_2$Et | S | 3-tetrahydrofuranyl | |
| 3.117 | Me | Cl | S | 3-tetrahydrofuranyl | |
| 3.118 | SMe | SO$_2$Me | S | 3-tetrahydrofuranyl | |
| 3.119 | SMe | SO$_2$Et | S | 3-tetrahydrofuranyl | |
| 3.120 | SMe | Cl | S | 3-tetrahydrofuranyl | |
| 3.121 | SO$_2$Me | SO$_2$Me | S | 3-tetrahydrofuranyl | |
| 3.122 | SO$_2$Me | SO$_2$Et | S | 3-tetrahydrofuranyl | |
| 3.123 | SO$_2$Me | Cl | S | 3-tetrahydrofuranyl | |
| 3.124 | NO$_2$ | SO$_2$Me | S | 3-tetrahydrofuranyl | |
| 3.125 | NO$_2$ | SO$_2$Et | S | 3-tetrahydrofuranyl | |
| 3.126 | NO$_2$ | Cl | S | 3-tetrahydrofuranyl | |
| 3.127 | Cl | SO$_2$Me | S | 4-tetrahydropyranyl | |
| 3.128 | Cl | SO$_2$Et | S | 4-tetrahydropyranyl | |
| 3.129 | Cl | Cl | S | 4-tetrahydropyranyl | |
| 3.130 | Br | SO$_2$Me | S | 4-tetrahydropyranyl | |
| 3.131 | Br | SO$_2$Et | S | 4-tetrahydropyranyl | |
| 3.132 | Br | Cl | S | 4-tetrahydropyranyl | |
| 3.133 | I | SO$_2$Me | S | 4-tetrahydropyranyl | |
| 3.134 | I | SO$_2$Et | S | 4-tetrahydropyranyl | |
| 3.135 | I | Cl | S | 4-tetrahydropyranyl | |
| 3.136 | Me | SO$_2$Me | S | 4-tetrahydropyranyl | |
| 3.137 | Me | SO$_2$Et | S | 4-tetrahydropyranyl | |
| 3.138 | Me | Cl | S | 4-tetrahydropyranyl | |
| 3.139 | SMe | SO$_2$Me | S | 4-tetrahydropyranyl | |
| 3.140 | SMe | SO$_2$Et | S | 4-tetrahydropyranyl | |
| 3.141 | SMe | Cl | S | 4-tetrahydropyranyl | |
| 3.142 | SO$_2$Me | SO$_2$Me | S | 4-tetrahydropyranyl | |
| 3.143 | SO$_2$Me | SO$_2$Et | S | 4-tetrahydropyranyl | |
| 3.144 | SO$_2$Me | Cl | S | 4-tetrahydropyranyl | |
| 3.145 | NO$_2$ | SO$_2$Me | S | 4-tetrahydropyranyl | |
| 3.146 | NO$_2$ | SO$_2$Et | S | 4-tetrahydropyranyl | |
| 3.147 | NO$_2$ | Cl | S | 4-tetrahydropyranyl | |
| 3.148 | Cl | SO$_2$Me | S | 3-tetrahydropyranyl | |
| 3.149 | Cl | SO$_2$Et | S | 3-tetrahydropyranyl | |
| 3.150 | Cl | Cl | S | 3-tetrahydropyranyl | |
| 3.151 | Br | SO$_2$Me | S | 3-tetrahydropyranyl | |
| 3.152 | Br | SO$_2$Et | S | 3-tetrahydropyranyl | |
| 3.153 | Br | Cl | S | 3-tetrahydropyranyl | |
| 3.154 | I | SO$_2$Me | S | 3-tetrahydropyranyl | |
| 3.155 | I | SO$_2$Et | S | 3-tetrahydropyranyl | |
| 3.156 | I | Cl | S | 3-tetrahydropyranyl | |
| 3.157 | Me | SO$_2$Me | S | 3-tetrahydropyranyl | |
| 3.158 | Me | SO$_2$Et | S | 3-tetrahydropyranyl | |
| 3.159 | Me | Cl | S | 3-tetrahydropyranyl | |
| 3.160 | SMe | SO$_2$Me | S | 3-tetrahydropyranyl | |
| 3.161 | SMe | SO$_2$Et | S | 3-tetrahydropyranyl | |
| 3.162 | SMe | Cl | S | 3-tetrahydropyranyl | |
| 3.163 | SO$_2$Me | SO$_2$Me | S | 3-tetrahydropyranyl | |
| 3.164 | SO$_2$Me | SO$_2$Et | S | 3-tetrahydropyranyl | |
| 3.165 | SO$_2$Me | Cl | S | 3-tetrahydropyranyl | |
| 3.166 | NO$_2$ | SO$_2$Me | S | 3-tetrahydropyranyl | |
| 3.167 | NO$_2$ | SO$_2$Et | S | 3-tetrahydropyranyl | |
| 3.168 | NO$_2$ | Cl | S | 3-tetrahydropyranyl | |
| 3.169 | Cl | SO$_2$Me | S | 1,3-dioxan-5-yl | |
| 3.170 | Cl | SO$_2$Et | S | 1,3-dioxan-5-yl | |

TABLE 3-continued

Compounds of the formula (I) according to the invention in which the substituents and symbols are as defined below:
$R^3 = H$ $Q = Q1$ $p = 2$

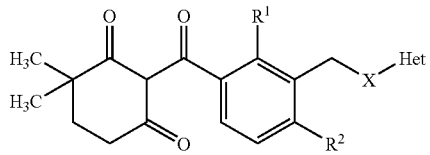

| No. | $R^1$ | $R^2$ | X | Het | Physical Data |
|---|---|---|---|---|---|
| 3.171 | Cl | Cl | S | 1,3-dioxan-5-yl | |
| 3.172 | Br | SO$_2$Me | S | 1,3-dioxan-5-yl | |
| 3.173 | Br | SO$_2$Et | S | 1,3-dioxan-5-yl | |
| 3.174 | Br | Cl | S | 1,3-dioxan-5-yl | |
| 3.175 | I | SO$_2$Me | S | 1,3-dioxan-5-yl | |
| 3.176 | I | SO$_2$Et | S | 1,3-dioxan-5-yl | |
| 3.177 | I | Cl | S | 1,3-dioxan-5-yl | |
| 3.178 | Me | SO$_2$Me | S | 1,3-dioxan-5-yl | |
| 3.179 | Me | SO$_2$Et | S | 1,3-dioxan-5-yl | |
| 3.180 | Me | Cl | S | 1,3-dioxan-5-yl | |
| 3.181 | SMe | SO$_2$Me | S | 1,3-dioxan-5-yl | |
| 3.182 | SMe | SO$_2$Et | S | 1,3-dioxan-5-yl | |
| 3.183 | SMe | Cl | S | 1,3-dioxan-5-yl | |
| 3.184 | SO$_2$Me | SO$_2$Me | S | 1,3-dioxan-5-yl | |
| 3.185 | SO$_2$Me | SO$_2$Et | S | 1,3-dioxan-5-yl | |
| 3.186 | SO$_2$Me | Cl | S | 1,3-dioxan-5-yl | |
| 3.187 | NO$_2$ | SO$_2$Me | S | 1,3-dioxan-5-yl | |
| 3.188 | NO$_2$ | SO$_2$Et | S | 1,3-dioxan-5-yl | |
| 3.189 | NO$_2$ | Cl | S | 1,3-dioxan-5-yl | |
| 3.190 | Cl | SO$_2$Me | S | γ-butyrolacton-2-yl | |
| 3.191 | Cl | SO$_2$Et | S | γ-butyrolacton-2-yl | |
| 3.192 | Cl | Cl | S | γ-butyrolacton-2-yl | |
| 3.193 | Br | SO$_2$Me | S | γ-butyrolacton-2-yl | |
| 3.194 | Br | SO$_2$Et | S | γ-butyrolacton-2-yl | |
| 3.195 | Br | Cl | S | γ-butyrolacton-2-yl | |
| 3.196 | I | SO$_2$Me | S | γ-butyrolacton-2-yl | |
| 3.197 | I | SO$_2$Et | S | γ-butyrolacton-2-yl | |
| 3.198 | I | Cl | S | γ-butyrolacton-2-yl | |
| 3.199 | Me | SO$_2$Me | S | γ-butyrolacton-2-yl | |
| 3.200 | Me | SO$_2$Et | S | γ-butyrolacton-2-yl | |
| 3.201 | Me | Cl | S | γ-butyrolacton-2-yl | |
| 3.202 | SMe | SO$_2$Me | S | γ-butyrolacton-2-yl | |
| 3.203 | SMe | SO$_2$Et | S | γ-butyrolacton-2-yl | |
| 3.204 | SMe | Cl | S | γ-butyrolacton-2-yl | |
| 3.205 | SO$_2$Me | SO$_2$Me | S | γ-butyrolacton-2-yl | |
| 3.206 | SO$_2$Me | SO$_2$Et | S | γ-butyrolacton-2-yl | |
| 3.207 | SO$_2$Me | Cl | S | γ-butyrolacton-2-yl | |
| 3.208 | NO$_2$ | SO$_2$Me | S | γ-butyrolacton-2-yl | |
| 3.209 | NO$_2$ | SO$_2$Et | S | γ-butyrolacton-2-yl | |
| 3.210 | NO$_2$ | Cl | S | γ-butyrolacton-2-yl | |

TABLE 4

Compounds of the formula (I) according to the invention in which the substituents and symbols are as defined below:
$R^3 = H$ $Q = Q2$ $R^6 = Me$
$R^7 = Me$ $R^8 = H$

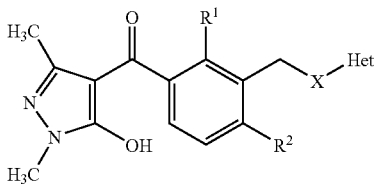

| No. | $R^1$ | $R^2$ | X | Het | Physical Data |
|---|---|---|---|---|---|
| 4.1 | Cl | SO$_2$Me | O | 3-tetrahydrofuranyl | oil, Rf = 0.1 (EA) |
| 4.2 | Cl | SO$_2$Et | O | 3-tetrahydrofuranyl | oil, Rf = 0.1 (EA) |

TABLE 4-continued

Compounds of the formula (I) according to the invention in which the substituents and symbols are as defined below:
$R^3 = H$ $Q = Q2$ $R^6 = Me$
$R^7 = Me$ $R^8 = H$

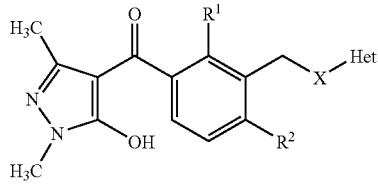

| No. | $R^1$ | $R^2$ | X | Het | Physical Data |
|---|---|---|---|---|---|
| 4.3 | Cl | Cl | O | 3-tetrahydrofuranyl | |
| 4.4 | Br | SO$_2$Me | O | 3-tetrahydrofuranyl | |
| 4.5 | Br | SO$_2$Et | O | 3-tetrahydrofuranyl | |
| 4.6 | Br | Cl | O | 3-tetrahydrofuranyl | |
| 4.7 | I | SO$_2$Me | O | 3-tetrahydrofuranyl | |
| 4.8 | I | SO$_2$Et | O | 3-tetrahydrofuranyl | |
| 4.9 | I | Cl | O | 3-tetrahydrofuranyl | |
| 4.10 | Me | SO$_2$Me | O | 3-tetrahydrofuranyl | oil, Rf = 0.1 (EA) |
| 4.11 | Me | SO$_2$Et | O | 3-tetrahydrofuranyl | |
| 4.12 | Me | Cl | O | 3-tetrahydrofuranyl | |
| 4.13 | SMe | SO$_2$Me | O | 3-tetrahydrofuranyl | |
| 4.14 | SMe | SO$_2$Et | O | 3-tetrahydrofuranyl | |
| 4.15 | SMe | Cl | O | 3-tetrahydrofuranyl | |
| 4.16 | SO$_2$Me | SO$_2$Me | O | 3-tetrahydrofuranyl | |
| 4.17 | SO$_2$Me | SO$_2$Et | O | 3-tetrahydrofuranyl | |
| 4.18 | SO$_2$Me | Cl | O | 3-tetrahydrofuranyl | |
| 4.19 | NO$_2$ | SO$_2$Me | O | 3-tetrahydrofuranyl | |
| 4.20 | NO$_2$ | SO$_2$Et | O | 3-tetrahydrofuranyl | |
| 4.21 | NO$_2$ | Cl | O | 3-tetrahydrofuranyl | |
| 4.22 | Cl | SO$_2$Me | O | 4-tetrahydropyranyl | |
| 4.23 | Cl | SO$_2$Et | O | 4-tetrahydropyranyl | |
| 4.24 | Cl | Cl | O | 4-tetrahydropyranyl | |
| 4.25 | Br | SO$_2$Me | O | 4-tetrahydropyranyl | |
| 4.26 | Br | SO$_2$Et | O | 4-tetrahydropyranyl | |
| 4.27 | Br | Cl | O | 4-tetrahydropyranyl | |
| 4.28 | I | SO$_2$Me | O | 4-tetrahydropyranyl | |
| 4.29 | I | SO$_2$Et | O | 4-tetrahydropyranyl | |
| 4.30 | I | Cl | O | 4-tetrahydropyranyl | |
| 4.31 | Me | SO$_2$Me | O | 4-tetrahydropyranyl | |
| 4.32 | Me | SO$_2$Et | O | 4-tetrahydropyranyl | |
| 4.33 | Me | Cl | O | 4-tetrahydropyranyl | |
| 4.34 | SMe | SO$_2$Me | O | 4-tetrahydropyranyl | |
| 4.35 | SMe | SO$_2$Et | O | 4-tetrahydropyranyl | |
| 4.36 | SMe | Cl | O | 4-tetrahydropyranyl | |
| 4.37 | SO$_2$Me | SO$_2$Me | O | 4-tetrahydropyranyl | |
| 4.38 | SO$_2$Me | SO$_2$Et | O | 4-tetrahydropyranyl | |
| 4.39 | SO$_2$Me | Cl | O | 4-tetrahydropyranyl | |
| 4.40 | NO$_2$ | SO$_2$Me | O | 4-tetrahydropyranyl | |
| 4.41 | NO$_2$ | SO$_2$Et | O | 4-tetrahydropyranyl | |
| 4.42 | NO$_2$ | Cl | O | 4-tetrahydropyranyl | |
| 4.43 | Cl | SO$_2$Me | O | 3-tetrahydropyranyl | |
| 4.44 | Cl | SO$_2$Et | O | 3-tetrahydropyranyl | |
| 4.45 | Cl | Cl | O | 3-tetrahydropyranyl | |
| 4.46 | Br | SO$_2$Me | O | 3-tetrahydropyranyl | |
| 4.47 | Br | SO$_2$Et | O | 3-tetrahydropyranyl | |
| 4.48 | Br | Cl | O | 3-tetrahydropyranyl | |
| 4.49 | I | SO$_2$Me | O | 3-tetrahydropyranyl | |
| 4.50 | I | SO$_2$Et | O | 3-tetrahydropyranyl | |
| 4.51 | I | Cl | O | 3-tetrahydropyranyl | |
| 4.52 | Me | SO$_2$Me | O | 3-tetrahydropyranyl | |
| 4.53 | Me | SO$_2$Et | O | 3-tetrahydropyranyl | |
| 4.54 | Me | Cl | O | 3-tetrahydropyranyl | |
| 4.55 | SMe | SO$_2$Me | O | 3-tetrahydropyranyl | |
| 4.56 | SMe | SO$_2$Et | O | 3-tetrahydropyranyl | |
| 4.57 | SMe | Cl | O | 3-tetrahydropyranyl | |
| 4.58 | SO$_2$Me | SO$_2$Me | O | 3-tetrahydropyranyl | |
| 4.59 | SO$_2$Me | SO$_2$Et | O | 3-tetrahydropyranyl | |
| 4.60 | SO$_2$Me | Cl | O | 3-tetrahydropyranyl | |
| 4.61 | NO$_2$ | SO$_2$Me | O | 3-tetrahydropyranyl | |
| 4.62 | NO$_2$ | SO$_2$Et | O | 3-tetrahydropyranyl | |
| 4.63 | NO$_2$ | Cl | O | 3-tetrahydropyranyl | |
| 4.64 | Cl | SO$_2$Me | O | 1,3-dioxan-5-yl | |

TABLE 4-continued

Compounds of the formula (I) according to the invention in which the substituents and symbols are as defined below:
$R^3$ = H  Q = Q2  $R^6$ = Me
$R^7$ = Me  $R^8$ = H

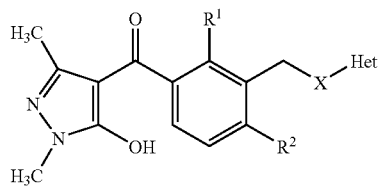

| No. | $R^1$ | $R^2$ | X | Het | Physical Data |
|---|---|---|---|---|---|
| 4.65 | Cl | SO$_2$Et | O | 1,3-dioxan-5-yl | |
| 4.66 | Cl | Cl | O | 1,3-dioxan-5-yl | |
| 4.67 | Br | SO$_2$Me | O | 1,3-dioxan-5-yl | |
| 4.68 | Br | SO$_2$Et | O | 1,3-dioxan-5-yl | |
| 4.69 | Br | Cl | O | 1,3-dioxan-5-yl | |
| 4.70 | I | SO$_2$Me | O | 1,3-dioxan-5-yl | |
| 4.71 | I | SO$_2$Et | O | 1,3-dioxan-5-yl | |
| 4.72 | I | Cl | O | 1,3-dioxan-5-yl | |
| 4.73 | Me | SO$_2$Me | O | 1,3-dioxan-5-yl | |
| 4.74 | Me | SO$_2$Et | O | 1,3-dioxan-5-yl | |
| 4.75 | Me | Cl | O | 1,3-dioxan-5-yl | |
| 4.76 | SMe | SO$_2$Me | O | 1,3-dioxan-5-yl | |
| 4.77 | SMe | SO$_2$Et | O | 1,3-dioxan-5-yl | |
| 4.78 | SMe | Cl | O | 1,3-dioxan-5-yl | |
| 4.79 | SO$_2$Me | SO$_2$Me | O | 1,3-dioxan-5-yl | |
| 4.80 | SO$_2$Me | SO$_2$Et | O | 1,3-dioxan-5-yl | |
| 4.81 | SO$_2$Me | Cl | O | 1,3-dioxan-5-yl | |
| 4.82 | NO$_2$ | SO$_2$Me | O | 1,3-dioxan-5-yl | |
| 4.83 | NO$_2$ | SO$_2$Et | O | 1,3-dioxan-5-yl | |
| 4.84 | NO$_2$ | Cl | O | 1,3-dioxan-5-yl | |
| 4.85 | Cl | SO$_2$Me | O | γ-butyrolacton-2-yl | |
| 4.86 | Cl | SO$_2$Et | O | γ-butyrolacton-2-yl | |
| 4.87 | Cl | Cl | O | γ-butyrolacton-2-yl | |
| 4.88 | Br | SO$_2$Me | O | γ-butyrolacton-2-yl | |
| 4.89 | Br | SO$_2$Et | O | γ-butyrolacton-2-yl | |
| 4.90 | Br | Cl | O | γ-butyrolacton-2-yl | |
| 4.91 | I | SO$_2$Me | O | γ-butyrolacton-2-yl | |
| 4.92 | I | SO$_2$Et | O | γ-butyrolacton-2-yl | |
| 4.93 | I | Cl | O | γ-butyrolacton-2-yl | |
| 4.94 | Me | SO$_2$Me | O | γ-butyrolacton-2-yl | |
| 4.95 | Me | SO$_2$Et | O | γ-butyrolacton-2-yl | |
| 4.96 | Me | Cl | O | γ-butyrolacton-2-yl | |
| 4.97 | SMe | SO$_2$Me | O | γ-butyrolacton-2-yl | |
| 4.98 | SMe | SO$_2$Et | O | γ-butyrolacton-2-yl | |
| 4.99 | SMe | Cl | O | γ-butyrolacton-2-yl | |
| 4.100 | SO$_2$Me | SO$_2$Me | O | γ-butyrolacton-2-yl | |
| 4.101 | SO$_2$Me | SO$_2$Et | O | γ-butyrolacton-2-yl | |
| 4.102 | SO$_2$Me | Cl | O | γ-butyrolacton-2-yl | |
| 4.103 | NO$_2$ | SO$_2$Me | O | γ-butyrolacton-2-yl | |
| 4.104 | NO$_2$ | SO$_2$Et | O | γ-butyrolacton-2-yl | |
| 4.105 | NO$_2$ | Cl | O | γ-butyrolacton-2-yl | |
| 4.106 | Cl | SO$_2$Me | S | 3-tetrahydrofuranyl | |
| 4.107 | Cl | SO$_2$Et | S | 3-tetrahydrofuranyl | |
| 4.108 | Cl | Cl | S | 3-tetrahydrofuranyl | |
| 4.109 | Br | SO$_2$Me | S | 3-tetrahydrofuranyl | |
| 4.110 | Br | SO$_2$Et | S | 3-tetrahydrofuranyl | |
| 4.111 | Br | Cl | S | 3-tetrahydrofuranyl | |
| 4.112 | I | SO$_2$Me | S | 3-tetrahydrofuranyl | |
| 4.113 | I | SO$_2$Et | S | 3-tetrahydrofuranyl | |
| 4.114 | I | Cl | S | 3-tetrahydrofuranyl | |
| 4.115 | Me | SO$_2$Me | S | 3-tetrahydrofuranyl | |
| 4.116 | Me | SO$_2$Et | S | 3-tetrahydrofuranyl | |
| 4.117 | Me | Cl | S | 3-tetrahydrofuranyl | |
| 4.118 | SMe | SO$_2$Me | S | 3-tetrahydrofuranyl | |
| 4.119 | SMe | SO$_2$Et | S | 3-tetrahydrofuranyl | |
| 4.120 | SMe | Cl | S | 3-tetrahydrofuranyl | |
| 4.121 | SO$_2$Me | SO$_2$Me | S | 3-tetrahydrofuranyl | |
| 4.122 | SO$_2$Me | SO$_2$Et | S | 3-tetrahydrofuranyl | |
| 4.123 | SO$_2$Me | Cl | S | 3-tetrahydrofuranyl | |
| 4.124 | NO$_2$ | SO$_2$Me | S | 3-tetrahydrofuranyl | |
| 4.125 | NO$_2$ | SO$_2$Et | S | 3-tetrahydrofuranyl | |
| 4.126 | NO$_2$ | Cl | S | 3-tetrahydrofuranyl | |

TABLE 4-continued

Compounds of the formula (I) according to the invention in which the substituents and symbols are as defined below:
$R^3$ = H  Q = Q2  $R^6$ = Me
$R^7$ = Me  $R^8$ = H

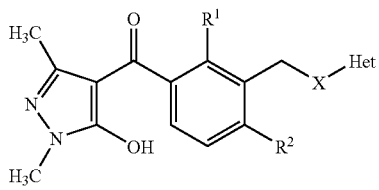

| No. | $R^1$ | $R^2$ | X | Het | Physical Data |
|---|---|---|---|---|---|
| 4.127 | Cl | SO$_2$Me | S | 4-tetrahydropyranyl | |
| 4.128 | Cl | SO$_2$Et | S | 4-tetrahydropyranyl | |
| 4.129 | Cl | Cl | S | 4-tetrahydropyranyl | |
| 4.130 | Br | SO$_2$Me | S | 4-tetrahydropyranyl | |
| 4.131 | Br | SO$_2$Et | S | 4-tetrahydropyranyl | |
| 4.132 | Br | Cl | S | 4-tetrahydropyranyl | |
| 4.133 | I | SO$_2$Me | S | 4-tetrahydropyranyl | |
| 4.134 | I | SO$_2$Et | S | 4-tetrahydropyranyl | |
| 4.135 | I | Cl | S | 4-tetrahydropyranyl | |
| 4.136 | Me | SO$_2$Me | S | 4-tetrahydropyranyl | |
| 4.137 | Me | SO$_2$Et | S | 4-tetrahydropyranyl | |
| 4.138 | Me | Cl | S | 4-tetrahydropyranyl | |
| 4.139 | SMe | SO$_2$Me | S | 4-tetrahydropyranyl | |
| 4.140 | SMe | SO$_2$Et | S | 4-tetrahydropyranyl | |
| 4.141 | SMe | Cl | S | 4-tetrahydropyranyl | |
| 4.142 | SO$_2$Me | SO$_2$Me | S | 4-tetrahydropyranyl | |
| 4.143 | SO$_2$Me | SO$_2$Et | S | 4-tetrahydropyranyl | |
| 4.144 | SO$_2$Me | Cl | S | 4-tetrahydropyranyl | |
| 4.145 | NO$_2$ | SO$_2$Me | S | 4-tetrahydropyranyl | |
| 4.146 | NO$_2$ | SO$_2$Et | S | 4-tetrahydropyranyl | |
| 4.147 | NO$_2$ | Cl | S | 4-tetrahydropyranyl | |
| 4.148 | Cl | SO$_2$Me | S | 3-tetrahydropyranyl | |
| 4.149 | Cl | SO$_2$Et | S | 3-tetrahydropyranyl | |
| 4.150 | Cl | Cl | S | 3-tetrahydropyranyl | |
| 4.151 | Br | SO$_2$Me | S | 3-tetrahydropyranyl | |
| 4.152 | Br | SO$_2$Et | S | 3-tetrahydropyranyl | |
| 4.153 | Br | Cl | S | 3-tetrahydropyranyl | |
| 4.154 | I | SO$_2$Me | S | 3-tetrahydropyranyl | |
| 4.155 | I | SO$_2$Et | S | 3-tetrahydropyranyl | |
| 4.156 | I | Cl | S | 3-tetrahydropyranyl | |
| 4.157 | Me | SO$_2$Me | S | 3-tetrahydropyranyl | |
| 4.158 | Me | SO$_2$Et | S | 3-tetrahydropyranyl | |
| 4.159 | Me | Cl | S | 3-tetrahydropyranyl | |
| 4.160 | SMe | SO$_2$Me | S | 3-tetrahydropyranyl | |
| 4.161 | SMe | SO$_2$Et | S | 3-tetrahydropyranyl | |
| 4.162 | SMe | Cl | S | 3-tetrahydropyranyl | |
| 4.163 | SO$_2$Me | SO$_2$Me | S | 3-tetrahydropyranyl | |
| 4.164 | SO$_2$Me | SO$_2$Et | S | 3-tetrahydropyranyl | |
| 4.165 | SO$_2$Me | Cl | S | 3-tetrahydropyranyl | |
| 4.166 | NO$_2$ | SO$_2$Me | S | 3-tetrahydropyranyl | |
| 4.167 | NO$_2$ | SO$_2$Et | S | 3-tetrahydropyranyl | |
| 4.168 | NO$_2$ | Cl | S | 3-tetrahydropyranyl | |
| 4.169 | Cl | SO$_2$Me | S | 1,3-dioxan-5-yl | |
| 4.170 | Cl | SO$_2$Et | S | 1,3-dioxan-5-yl | |
| 4.171 | Cl | Cl | S | 1,3-dioxan-5-yl | |
| 4.172 | Br | SO$_2$Me | S | 1,3-dioxan-5-yl | |
| 4.173 | Br | SO$_2$Et | S | 1,3-dioxan-5-yl | |
| 4.174 | Br | Cl | S | 1,3-dioxan-5-yl | |
| 4.175 | I | SO$_2$Me | S | 1,3-dioxan-5-yl | |
| 4.176 | I | SO$_2$Et | S | 1,3-dioxan-5-yl | |
| 4.177 | I | Cl | S | 1,3-dioxan-5-yl | |
| 4.178 | Me | SO$_2$Me | S | 1,3-dioxan-5-yl | |
| 4.179 | Me | SO$_2$Et | S | 1,3-dioxan-5-yl | |
| 4.180 | Me | Cl | S | 1,3-dioxan-5-yl | |
| 4.181 | SMe | SO$_2$Me | S | 1,3-dioxan-5-yl | |
| 4.182 | SMe | SO$_2$Et | S | 1,3-dioxan-5-yl | |
| 4.183 | SMe | Cl | S | 1,3-dioxan-5-yl | |
| 4.184 | SO$_2$Me | SO$_2$Me | S | 1,3-dioxan-5-yl | |
| 4.185 | SO$_2$Me | SO$_2$Et | S | 1,3-dioxan-5-yl | |
| 4.186 | SO$_2$Me | Cl | S | 1,3-dioxan-5-yl | |
| 4.187 | NO$_2$ | SO$_2$Me | S | 1,3-dioxan-5-yl | |
| 4.188 | NO$_2$ | SO$_2$Et | S | 1,3-dioxan-5-yl | |

TABLE 4-continued

Compounds of the formula (I) according to the invention in which the substituents and symbols are as defined below:
$R^3 = H$  $Q = Q2$  $R^6 = Me$
$R^7 = Me$  $R^8 = H$

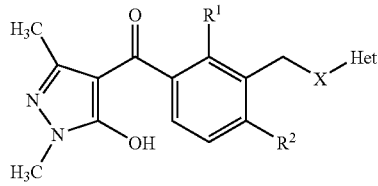

| No. | $R^1$ | $R^2$ | X | Het | Physical Data |
|---|---|---|---|---|---|
| 4.189 | NO$_2$ | Cl | S | 1,3-dioxan-5-yl | |
| 4.190 | Cl | SO$_2$Me | S | γ-butyrolacton-2-yl | |
| 4.191 | Cl | SO$_2$Et | S | γ-butyrolacton-2-yl | |
| 4.192 | Cl | Cl | S | γ-butyrolacton-2-yl | |
| 4.193 | Br | SO$_2$Me | S | γ-butyrolacton-2-yl | |
| 4.194 | Br | SO$_2$Et | S | γ-butyrolacton-2-yl | |
| 4.195 | Br | Cl | S | γ-butyrolacton-2-yl | |
| 4.196 | I | SO$_2$Me | S | γ-butyrolacton-2-yl | |
| 4.197 | I | SO$_2$Et | S | γ-butyrolacton-2-yl | |
| 4.198 | I | Cl | S | γ-butyrolacton-2-yl | |
| 4.199 | Me | SO$_2$Me | S | γ-butyrolacton-2-yl | |
| 4.200 | Me | SO$_2$Et | S | γ-butyrolacton-2-yl | |
| 4.201 | Me | Cl | S | γ-butyrolacton-2-yl | |
| 4.202 | SMe | SO$_2$Me | S | γ-butyrolacton-2-yl | |
| 4.203 | SMe | SO$_2$Et | S | γ-butyrolacton-2-yl | |
| 4.204 | SMe | Cl | S | γ-butyrolacton-2-yl | |
| 4.205 | SO$_2$Me | SO$_2$Me | S | γ-butyrolacton-2-yl | |
| 4.206 | SO$_2$Me | SO$_2$Et | S | γ-butyrolacton-2-yl | |
| 4.207 | SO$_2$Me | Cl | S | γ-butyrolacton-2-yl | |
| 4.208 | NO$_2$ | SO$_2$Me | S | γ-butyrolacton-2-yl | |
| 4.209 | NO$_2$ | SO$_2$Et | S | γ-butyrolacton-2-yl | |
| 4.210 | NO$_2$ | Cl | S | γ-butyrolacton-2-yl | |

TABLE 5

Compounds of the formula (I) according to the invention in which the substituents and symbols are as defined below:
$R^3 = H$  $Q = Q2$  $R^6 = H$
$R^7 = Me$  $R^8 = H$

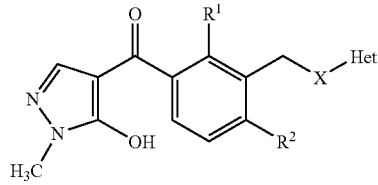

| No. | $R^1$ | $R^2$ | X | Het | Physical data |
|---|---|---|---|---|---|
| 5.1 | Cl | SO$_2$Me | O | 3-tetrahydrofuranyl | oil, Rf = 0.1 (EA) |
| 5.2 | Cl | SO$_2$Et | O | 3-tetrahydrofuranyl | oil, Rf = 0.1 (EA) |
| 5.3 | Cl | Cl | O | 3-tetrahydrofuranyl | |
| 5.4 | Br | SO$_2$Me | O | 3-tetrahydrofuranyl | |
| 5.5 | Br | SO$_2$Et | O | 3-tetrahydrofuranyl | |
| 5.6 | Br | Cl | O | 3-tetrahydrofuranyl | |
| 5.7 | I | SO$_2$Me | O | 3-tetrahydrofuranyl | |
| 5.8 | I | SO$_2$Et | O | 3-tetrahydrofuranyl | |
| 5.9 | I | Cl | O | 3-tetrahydrofuranyl | |
| 5.10 | Me | SO$_2$Me | O | 3-tetrahydrofuranyl | |
| 5.11 | Me | SO$_2$Et | O | 3-tetrahydrofuranyl | |
| 5.12 | Me | Cl | O | 3-tetrahydrofuranyl | |
| 5.13 | SMe | SO$_2$Me | O | 3-tetrahydrofuranyl | |
| 5.14 | SMe | SO$_2$Et | O | 3-tetrahydrofuranyl | |
| 5.15 | SMe | Cl | O | 3-tetrahydrofuranyl | |
| 5.16 | SO$_2$Me | SO$_2$Me | O | 3-tetrahydrofuranyl | |
| 5.17 | SO$_2$Me | SO$_2$Et | O | 3-tetrahydrofuranyl | |
| 5.18 | SO$_2$Me | Cl | O | 3-tetrahydrofuranyl | |

TABLE 5-continued

Compounds of the formula (I) according to the invention in which the substituents and symbols are as defined below:
$R^3 = H$  $Q = Q2$  $R^6 = H$
$R^7 = Me$  $R^8 = H$

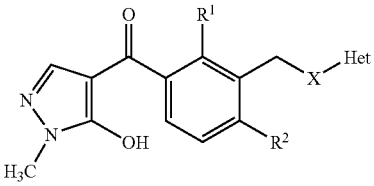

| No. | $R^1$ | $R^2$ | X | Het | Physical data |
|---|---|---|---|---|---|
| 5.19 | NO$_2$ | SO$_2$Me | O | 3-tetrahydrofuranyl | |
| 5.20 | NO$_2$ | SO$_2$Et | O | 3-tetrahydrofuranyl | |
| 5.21 | NO$_2$ | Cl | O | 3-tetrahydrofuranyl | |
| 5.22 | Cl | SO$_2$Me | O | 4-tetrahydropyranyl | |
| 5.23 | Cl | SO$_2$Et | O | 4-tetrahydropyranyl | |
| 5.24 | Cl | Cl | O | 4-tetrahydropyranyl | |
| 5.25 | Br | SO$_2$Me | O | 4-tetrahydropyranyl | |
| 5.26 | Br | SO$_2$Et | O | 4-tetrahydropyranyl | |
| 5.27 | Br | Cl | O | 4-tetrahydropyranyl | |
| 5.28 | I | SO$_2$Me | O | 4-tetrahydropyranyl | |
| 5.29 | I | SO$_2$Et | O | 4-tetrahydropyranyl | |
| 5.30 | I | Cl | O | 4-tetrahydropyranyl | |
| 5.31 | Me | SO$_2$Me | O | 4-tetrahydropyranyl | |
| 5.32 | Me | SO$_2$Et | O | 4-tetrahydropyranyl | |
| 5.33 | Me | Cl | O | 4-tetrahydropyranyl | |
| 5.34 | SMe | SO$_2$Me | O | 4-tetrahydropyranyl | |
| 5.35 | SMe | SO$_2$Et | O | 4-tetrahydropyranyl | |
| 5.36 | SMe | Cl | O | 4-tetrahydropyranyl | |
| 5.37 | SO$_2$Me | SO$_2$Me | O | 4-tetrahydropyranyl | |
| 5.38 | SO$_2$Me | SO$_2$Et | O | 4-tetrahydropyranyl | |
| 5.39 | SO$_2$Me | Cl | O | 4-tetrahydropyranyl | |
| 5.40 | NO$_2$ | SO$_2$Me | O | 4-tetrahydropyranyl | |
| 5.41 | NO$_2$ | SO$_2$Et | O | 4-tetrahydropyranyl | |
| 5.42 | NO$_2$ | Cl | O | 4-tetrahydropyranyl | |
| 5.43 | Cl | SO$_2$Me | O | 3-tetrahydropyranyl | |
| 5.44 | Cl | SO$_2$Et | O | 3-tetrahydropyranyl | |
| 5.45 | Cl | Cl | O | 3-tetrahydropyranyl | |
| 5.46 | Br | SO$_2$Me | O | 3-tetrahydropyranyl | |
| 5.47 | Br | SO$_2$Et | O | 3-tetrahydropyranyl | |
| 5.48 | Br | Cl | O | 3-tetrahydropyranyl | |
| 5.49 | I | SO$_2$Me | O | 3-tetrahydropyranyl | |
| 5.50 | I | SO$_2$Et | O | 3-tetrahydropyranyl | |
| 5.51 | I | Cl | O | 3-tetrahydropyranyl | |
| 5.52 | Me | SO$_2$Me | O | 3-tetrahydropyranyl | |
| 5.53 | Me | SO$_2$Et | O | 3-tetrahydropyranyl | |
| 5.54 | Me | Cl | O | 3-tetrahydropyranyl | |
| 5.55 | SMe | SO$_2$Me | O | 3-tetrahydropyranyl | |
| 5.56 | SMe | SO$_{2Et}$ | O | 3-tetrahydropyranyl | |
| 5.57 | SMe | Cl | O | 3-tetrahydropyranyl | |
| 5.58 | SO$_2$Me | SO$_2$Me | O | 3-tetrahydropyranyl | |
| 5.59 | SO$_2$Me | SO$_2$Et | O | 3-tetrahydropyranyl | |
| 5.60 | SO$_2$Me | Cl | O | 3-tetrahydropyranyl | |
| 5.61 | NO$_2$ | SO$_2$Me | O | 3-tetrahydropyranyl | |
| 5.62 | NO$_2$ | SO$_2$Et | O | 3-tetrahydropyranyl | |
| 5.63 | NO$_2$ | Cl | O | 3-tetrahydropyranyl | |
| 5.64 | Cl | SO$_2$Me | O | 1,3-dioxan-5-yl | |
| 5.65 | Cl | SO$_2$Et | O | 1,3-dioxan-5-yl | |
| 5.66 | Cl | Cl | O | 1,3-dioxan-5-yl | |
| 5.67 | Br | SO$_2$Me | O | 1,3-dioxan-5-yl | |
| 5.68 | Br | SO$_2$Et | O | 1,3-dioxan-5-yl | |
| 5.69 | Br | Cl | O | 1,3-dioxan-5-yl | |
| 5.70 | I | SO$_2$Me | O | 1,3-dioxan-5-yl | |
| 5.71 | I | SO$_2$Et | O | 1,3-dioxan-5-yl | |
| 5.72 | I | Cl | O | 1,3-dioxan-5-yl | |
| 5.73 | Me | SO$_2$Me | O | 1,3-dioxan-5-yl | |
| 5.74 | Me | SO$_2$Et | O | 1,3-dioxan-5-yl | |
| 5.75 | Me | Cl | O | 1,3-dioxan-5-yl | |
| 5.76 | SMe | SO$_2$Me | O | 1,3-dioxan-5-yl | |
| 5.77 | SMe | SO$_2$Et | O | 1,3-dioxan-5-yl | |
| 5.78 | SMe | Cl | O | 1,3-dioxan-5-yl | |
| 5.79 | SO$_2$Me | SO$_2$Me | O | 1,3-dioxan-5-yl | |
| 5.80 | SO$_2$Me | SO$_2$Et | O | 1,3-dioxan-5-yl | |

TABLE 5-continued

Compounds of the formula (I) according to the invention in which the substituents and symbols are as defined below:

$R^3 = H$  $\quad Q = Q2$  $\quad R^6 = H$
$R^7 = Me$  $\quad R^8 = H$

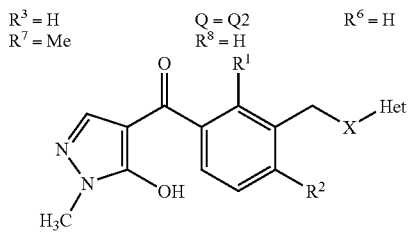

| No. | R¹ | R² | X | Het | Physical data |
|---|---|---|---|---|---|
| 5.81 | SO₂Me | Cl | O | 1,3-dioxan-5-yl | |
| 5.82 | NO₂ | SO₂Me | O | 1,3-dioxan-5-yl | |
| 5.83 | NO₂ | SO₂Et | O | 1,3-dioxan-5-yl | |
| 5.84 | NO₂ | Cl | O | 1,3-dioxan-5-yl | |
| 5.85 | Cl | SO₂Me | O | γ-butyrolacton-2-yl | |
| 5.86 | Cl | SO₂Et | O | γ-butyrolacton-2-yl | |
| 5.87 | Cl | Cl | O | γ-butyrolacton-2-yl | |
| 5.88 | Br | SO₂Me | O | γ-butyrolacton-2-yl | |
| 5.89 | Br | SO₂Et | O | γ-butyrolacton-2-yl | |
| 5.90 | Br | Cl | O | γ-butyrolacton-2-yl | |
| 5.91 | I | SO₂Me | O | γ-butyrolacton-2-yl | |
| 5.92 | I | SO₂Et | O | γ-butyrolacton-2-yl | |
| 5.93 | I | Cl | O | γ-butyrolacton-2-yl | |
| 5.94 | Me | SO₂Me | O | γ-butyrolacton-2-yl | |
| 5.95 | Me | SO₂Et | O | γ-butyrolacton-2-yl | |
| 5.96 | Me | Cl | O | γ-butyrolacton-2-yl | |
| 5.97 | SMe | SO₂Me | O | γ-butyrolacton-2-yl | |
| 5.98 | SMe | SO₂Et | O | γ-butyrolacton-2-yl | |
| 5.99 | SMe | Cl | O | γ-butyrolacton-2-yl | |
| 5.100 | SO₂Me | SO₂Me | O | γ-butyrolacton-2-yl | |
| 5.101 | SO₂Me | SO₂Et | O | γ-butyrolacton-2-yl | |
| 5.102 | SO₂Me | Cl | O | γ-butyrolacton-2-yl | |
| 5.103 | NO₂ | SO₂Me | O | γ-butyrolacton-2-yl | |
| 5.104 | NO₂ | SO₂Et | O | γ-butyrolacton-2-yl | |
| 5.105 | NO₂ | Cl | O | γ-butyrolacton-2-yl | |
| 5.106 | Cl | SO₂Me | S | 3-tetrahydrofuranyl | |
| 5.107 | Cl | SO₂Et | S | 3-tetrahydrofuranyl | |
| 5.108 | Cl | Cl | S | 3-tetrahydrofuranyl | |
| 5.109 | Br | SO₂Me | S | 3-tetrahydrofuranyl | |
| 5.110 | Br | SO₂Et | S | 3-tetrahydrofuranyl | |
| 5.111 | Br | Cl | S | 3-tetrahydrofuranyl | |
| 5.112 | I | SO₂Me | S | 3-tetrahydrofuranyl | |
| 5.113 | I | SO₂Et | S | 3-tetrahydrofuranyl | |
| 5.114 | I | Cl | S | 3-tetrahydrofuranyl | |
| 5.115 | Me | SO₂Me | S | 3-tetrahydrofuranyl | |
| 5.116 | Me | SO₂Et | S | 3-tetrahydrofuranyl | |
| 5.117 | Me | Cl | S | 3-tetrahydrofuranyl | |
| 5.118 | SMe | SO₂Me | S | 3-tetrahydrofuranyl | |
| 5.119 | SMe | SO₂Et | S | 3-tetrahydrofuranyl | |
| 5.120 | SMe | Cl | S | 3-tetrahydrofuranyl | |
| 5.121 | SO₂Me | SO₂Me | S | 3-tetrahydrofuranyl | |
| 5.122 | SO₂Me | SO₂Et | S | 3-tetrahydrofuranyl | |
| 5.123 | SO₂Me | Cl | S | 3-tetrahydrofuranyl | |
| 5.124 | NO₂ | SO₂Me | S | 3-tetrahydrofuranyl | |
| 5.125 | NO₂ | SO₂Et | S | 3-tetrahydrofuranyl | |
| 5.126 | NO₂ | Cl | S | 3-tetrahydrofuranyl | |
| 5.127 | Cl | SO₂Me | S | 4-tetrahydropyranyl | |
| 5.128 | Cl | SO₂Et | S | 4-tetrahydropyranyl | |
| 5.129 | Cl | Cl | S | 4-tetrahydropyranyl | |
| 5.130 | Br | SO₂Me | S | 4-tetrahydropyranyl | |
| 5.131 | Br | SO₂Et | S | 4-tetrahydropyranyl | |
| 5.132 | Br | Cl | S | 4-tetrahydropyranyl | |
| 5.133 | I | SO₂Me | S | 4-tetrahydropyranyl | |
| 5.134 | I | SO₂Et | S | 4-tetrahydropyranyl | |
| 5.135 | I | Cl | S | 4-tetrahydropyranyl | |
| 5.136 | Me | SO₂Me | S | 4-tetrahydropyranyl | |
| 5.137 | Me | SO₂Et | S | 4-tetrahydropyranyl | |
| 5.138 | Me | Cl | S | 4-tetrahydropyranyl | |
| 5.139 | SMe | SO₂Me | S | 4-tetrahydropyranyl | |
| 5.140 | SMe | SO₂Et | S | 4-tetrahydropyranyl | |
| 5.141 | SMe | Cl | S | 4-tetrahydropyranyl | |
| 5.142 | SO₂Me | SO₂Me | S | 4-tetrahydropyranyl | |

TABLE 5-continued

Compounds of the formula (I) according to the invention in which the substituents and symbols are as defined below:

$R^3 = H$  $\quad Q = Q2$  $\quad R^6 = H$
$R^7 = Me$  $\quad R^8 = H$

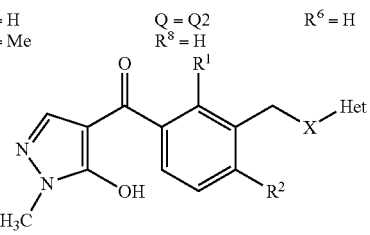

| No. | R¹ | R² | X | Het | Physical data |
|---|---|---|---|---|---|
| 5.143 | SO₂Me | SO₂Et | S | 4-tetrahydropyranyl | |
| 5.144 | SO₂Me | Cl | S | 4-tetrahydropyranyl | |
| 5.145 | NO₂ | SO₂Me | S | 4-tetrahydropyranyl | |
| 5.146 | NO₂ | SO₂Et | S | 4-tetrahydropyranyl | |
| 5.147 | NO₂ | Cl | S | 4-tetrahydropyranyl | |
| 5.148 | Cl | SO₂Me | S | 3-tetrahydropyranyl | |
| 5.149 | Cl | SO₂Et | S | 3-tetrahydropyranyl | |
| 5.150 | Cl | Cl | S | 3-tetrahydropyranyl | |
| 5.151 | Br | SO₂Me | S | 3-tetrahydropyranyl | |
| 5.152 | Br | SO₂Et | S | 3-tetrahydropyranyl | |
| 5.153 | Br | Cl | S | 3-tetrahydropyranyl | |
| 5.154 | I | SO₂Me | S | 3-tetrahydropyranyl | |
| 5.155 | I | SO₂Et | S | 3-tetrahydropyranyl | |
| 5.156 | I | Cl | S | 3-tetrahydropyranyl | |
| 5.157 | Me | SO₂Me | S | 3-tetrahydropyranyl | |
| 5.158 | Me | SO₂Et | S | 3-tetrahydropyranyl | |
| 5.159 | Me | Cl | S | 3-tetrahydropyranyl | |
| 5.160 | SMe | SO₂Me | S | 3-tetrahydropyranyl | |
| 5.161 | SMe | SO₂Et | S | 3-tetrahydropyranyl | |
| 5.162 | SMe | Cl | S | 3-tetrahydropyranyl | |
| 5.163 | SO₂Me | SO₂Me | S | 3-tetrahydropyranyl | |
| 5.164 | SO₂Me | SO₂Et | S | 3-tetrahydropyranyl | |
| 5.165 | SO₂Me | Cl | S | 3-tetrahydropyranyl | |
| 5.166 | NO₂ | SO₂Me | S | 3-tetrahydropyranyl | |
| 5.167 | NO₂ | SO₂Et | S | 3-tetrahydropyranyl | |
| 5.168 | NO₂ | Cl | S | 3-tetrahydropyranyl | |
| 5.169 | Cl | SO₂Me | S | 1,3-dioxan-5-yl | |
| 5.170 | Cl | SO₂Et | S | 1,3-dioxan-5-yl | |
| 5.171 | Cl | Cl | S | 1,3-dioxan-5-yl | |
| 5.172 | Br | SO₂Me | S | 1,3-dioxan-5-yl | |
| 5.173 | Br | SO₂Et | S | 1,3-dioxan-5-yl | |
| 5.174 | Br | Cl | S | 1,3-dioxan-5-yl | |
| 5.175 | I | SO₂Me | S | 1,3-dioxan-5-yl | |
| 5.176 | I | SO₂Et | S | 1,3-dioxan-5-yl | |
| 5.177 | I | Cl | S | 1,3-dioxan-5-yl | |
| 5.178 | Me | SO₂Me | S | 1,3-dioxan-5-yl | |
| 5.179 | Me | SO₂Et | S | 1,3-dioxan-5-yl | |
| 5.180 | Me | Cl | S | 1,3-dioxan-5-yl | |
| 5.181 | SMe | SO₂Me | S | 1,3-dioxan-5-yl | |
| 5.182 | SMe | SO₂Et | S | 1,3-dioxan-5-yl | |
| 5.183 | SMe | Cl | S | 1,3-dioxan-5-yl | |
| 5.184 | SO₂Me | SO₂Me | S | 1,3-dioxan-5-yl | |
| 5.185 | SO₂Me | SO₂Et | S | 1,3-dioxan-5-yl | |
| 5.186 | SO₂Me | Cl | S | 1,3-dioxan-5-yl | |
| 5.187 | NO₂ | SO₂Me | S | 1,3-dioxan-5-yl | |
| 5.188 | NO₂ | SO₂Et | S | 1,3-dioxan-5-yl | |
| 5.189 | NO₂ | Cl | S | 1,3-dioxan-5-yl | |
| 5.190 | Cl | SO₂Me | S | γ-butyrolacton-2-yl | |
| 5.191 | Cl | SO₂Et | S | γ-butyrolacton-2-yl | |
| 5.192 | Cl | Cl | S | γ-butyrolacton-2-yl | |
| 5.193 | Br | SO₂Me | S | γ-butyrolacton-2-yl | |
| 5.194 | Br | SO₂Et | S | γ-butyrolacton-2-yl | |
| 5.195 | Br | Cl | S | γ-butyrolacton-2-yl | |
| 5.196 | I | SO₂Me | S | γ-butyrolacton-2-yl | |
| 5.197 | I | SO₂Et | S | γ-butyrolacton-2-yl | |
| 5.198 | I | Cl | S | γ-butyrolacton-2-yl | |
| 5.199 | Me | SO₂Me | S | γ-butyrolacton-2-yl | |
| 5.200 | Me | SO₂Et | S | γ-butyrolacton-2-yl | |
| 5.201 | Me | Cl | S | γ-butyrolacton-2-yl | |
| 5.202 | SMe | SO₂Me | S | γ-butyrolacton-2-yl | |
| 5.203 | SMe | SO₂Et | S | γ-butyrolacton-2-yl | |
| 5.204 | SMe | Cl | S | γ-butyrolacton-2-yl | |

TABLE 5-continued

Compounds of the formula (I) according to the invention in which the substituents and symbols are as defined below:

R³ = H, R⁷ = Me, Q = Q2, R⁸ = H, R⁶ = H

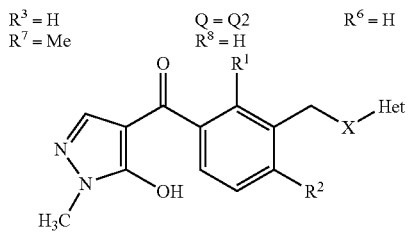

| No. | R¹ | R² | X | Het | Physical data |
|---|---|---|---|---|---|
| 5.205 | SO₂Me | SO₂Me | S | γ-butyrolacton-2-yl | |
| 5.206 | SO₂Me | SO₂Et | S | γ-butyrolacton-2-yl | |
| 5.207 | SO₂Me | Cl | S | γ-butyrolacton-2-yl | |
| 5.208 | NO₂ | SO₂Me | S | γ-butyrolacton-2-yl | |
| 5.209 | NO₂ | SO₂Et | S | γ-butyrolacton-2-yl | |
| 5.210 | NO₂ | Cl | S | γ-butyrolacton-2-yl | |
| 5.211 | OMe | Cl | O | 3-tetrahydrofuranyl | oil, Rf = 0.1 (EA) |

TABLE 6

Compounds of the formula (I) according to the invention in which the substituents and symbols are as defined below:

R³ = H, R⁷ = Et, Q = Q2, R⁸ = H, R⁶ = H

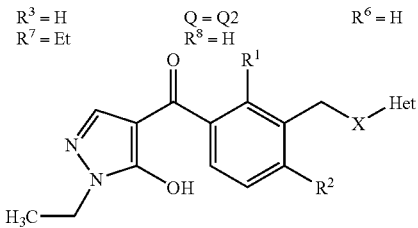

| No. | R¹ | R² | X | Het | Physical data |
|---|---|---|---|---|---|
| 6.1 | Cl | SO₂Me | O | 3 tetrahydrofuranyl | oil, Rf = 0.1 (EA) |
| 6.2 | Cl | SO₂Et | O | 3 tetrahydrofuranyl | |
| 6.3 | Cl | Cl | O | 3 tetrahydrofuranyl | |
| 6.4 | Br | SO₂Me | O | 3 tetrahydrofuranyl | |
| 6.5 | Br | SO₂Et | O | 3-tetrahydrofuranyl | |
| 6.6 | Br | Cl | O | 3-tetrahydrofuranyl | |
| 6.7 | I | SO₂Me | O | 3-tetrahydrofuranyl | |
| 6.8 | I | SO₂Et | O | 3-tetrahydrofuranyl | |
| 6.9 | | cl | O | 3-tetrahydrofuranyl | |
| 6.10 | Me | SO₂Me | O | 3-tetrahydrofuranyl | |
| 6.11 | Me | SO₂Et | O | 3-tetrahydrofuranyl | |
| 6.12 | Me | Cl | O | 3-tetrahydrofuranyl | |
| 6.13 | SMe | SO₂Me | O | 3-tetrahydrofuranyl | |
| 6.14 | SMe | SO₂Et | O | 3-tetrahydrofuranyl | |
| 6.15 | SMe | Cl | O | 3-tetrahydrofuranyl | |
| 6.16 | SO₂Me | SO₂Me | O | 3-tetrahydrofuranyl | |
| 6.17 | SO₂Me | SO₂Et | O | 3-tetrahydrofuranyl | |
| 6.18 | SO₂Me | Cl | O | 3-tetrahydrofuranyl | |
| 6.19 | NO₂ | SO₂Me | O | 3-tetrahydrofuranyl | |
| 6.20 | NO₂ | SO₂Et | O | 3-tetrahydrofuranyl | |
| 6.21 | NO₂ | cl | O | 3-tetrahydrofuranyl | |
| 6.22 | Cl | SO₂Me | O | 4-tetrahydropyranyl | |
| 6.23 | Cl | SO₂Et | O | 4-tetrahydropyranyl | |
| 6.24 | Cl | Cl | O | 4-tetrahydropyranyl | |
| 6.25 | Br | SO₂Me | O | 4-tetrahydropyranyl | |
| 6.26 | Br | SO₂Et | O | 4-tetrahydropyranyl | |
| 6.27 | Br | Cl | O | 4-tetrahydropyranyl | |
| 6.28 | I | SO₂Me | O | 4-tetrahydropyranyl | |
| 6.29 | I | SO₂Et | O | 4-tetrahydropyranyl | |
| 6.30 | I | Cl | O | 4-tetrahydropyranyl | |
| 6.31 | Me | SO₂Me | O | 4-tetrahydropyranyl | |
| 6.32 | Me | SO₂Et | O | 4-tetrahydropyranyl | |
| 6.33 | Me | Cl | O | 4-tetrahydropyranyl | |

TABLE 6-continued

Compounds of the formula (I) according to the invention in which the substituents and symbols are as defined below:

R³ = H, R⁷ = Et, Q = Q2, R⁸ = H, R⁶ = H

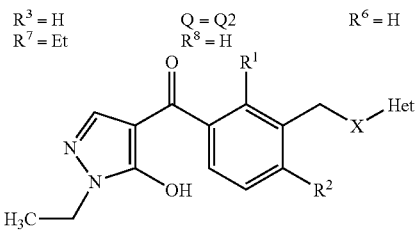

| No. | R¹ | R² | X | Het | Physical data |
|---|---|---|---|---|---|
| 6.34 | SMe | SO₂Me | O | 4-tetrahydropyranyl | |
| 6.35 | SMe | SO₂Et | O | 4-tetrahydropyranyl | |
| 6.36 | SMe | Cl | O | 4-tetrahydropyranyl | |
| 6.37 | SO₂Me | SO₂Me | O | 4-tetrahydropyranyl | |
| 6.38 | SO₂Me | SO₂Et | O | 4-tetrahydropyranyl | |
| 6.39 | SO₂Me | Cl | O | 4-tetrahydropyranyl | |
| 6.40 | NO₂ | SO₂Me | O | 4-tetrahydropyranyl | |
| 6.41 | NO₂ | SO₂Et | O | 4-tetrahydropyranyl | |
| 6.42 | NO₂ | Cl | O | 4-tetrahydropyranyl | |
| 6.43 | Cl | SO₂Me | O | 3-tetrahydropyranyl | |
| 6.44 | Cl | SO₂Et | O | 3-tetrahydropyranyl | |
| 6.45 | Cl | Cl | O | 3-tetrahydropyranyl | |
| 6.46 | Br | SO₂Me | O | 3-tetrahydropyranyl | |
| 6.47 | Br | SO₂Et | O | 3-tetrahydropyranyl | |
| 6.48 | Br | Cl | O | 3-tetrahydropyranyl | |
| 6.49 | I | SO₂Me | O | 3-tetrahydropyranyl | |
| 6.50 | I | SO₂Et | O | 3-tetrahydropyranyl | |
| 6.51 | I | Cl | O | 3-tetrahydropyranyl | |
| 6.52 | Me | SO₂Me | O | 3-tetrahydropyrfanyl | |
| 6.53 | Me | SO₂Et | O | 3-tetrahydropyranyl | |
| 6.54 | Me | Cl | O | 3-tetrahydropyranyl | |
| 6.55 | SMe | SO₂Me | O | 3-tetrahydropyranyl | |
| 6.56 | SMe | SO₂Et | O | 3-tetrahydropyranyl | |
| 6.57 | SMe | Cl | O | 3-tetrahydropyranyl | |
| 6.58 | SO₂Me | SO₂Me | O | 3-tetrahydropyranyl | |
| 6.59 | SO₂Me | SO₂Et | O | 3-tetrahydropyranyl | |
| 6.60 | SO₂Me | Cl | O | 3-tetrahydropyranyl | |
| 6.61 | NO₂ | SO₂Me | O | 3-tetrahydropyranyl | |
| 6.62 | NO₂ | SO₂Et | O | 3-tetrahydropyranyl | |
| 6.63 | NO2 | Cl | O | 3-tetrahydropyranyl | |
| 6.64 | Cl | SO₂Me | O | 1,3-dioxan-5-yl | |
| 6.65 | Cl | SO₂Et | O | 1,3-dioxan-5-yl | |
| 6.66 | Cl | Cl | O | 1,3-dioxan-5-yl | |
| 6.67 | Br | SO₂Me | O | 1,3-dioxan-5-yl | |
| 6.68 | Br | SO₂Et | O | 1,3-dioxan-5-yl | |
| 6.69 | Br | Cl | O | 1,3-dioxan-5-yl | |
| 6.70 | I | SO₂Me | O | 1,3-dioxan-5-yl | |
| 6.71 | I | SO₂Et | O | 1,3-dioxan-5-yl | |
| 6.72 | I | Cl | O | 1,3-dioxan-5-yl | |
| 6.73 | Me | SO₂Me | O | 1,3-dioxan-5-yl | |
| 6.74 | Me | SO₂Et | O | 1,3-dioxan-5-yl | |
| 6.75 | Me | Cl | O | 1,3-dioxan-5-yl | |
| 6.76 | SMe | SO₂Me | O | 1,3-dioxan-5-yl | |
| 6.77 | SMe | SO₂Et | O | 1,3-dioxan-5-yl | |
| 6.78 | SMe | Cl | O | 1,3-dioxan-5-yl | |
| 6.79 | SO₂Me | SO₂Me | O | 1,3-dioxan-5-yl | |
| 6.80 | SO₂Me | SO₂Et | O | 1,3-dioxan-5-yl | |
| 6.81 | SO₂Me | Cl | O | 1,3-dioxan-5-yl | |
| 6.82 | NO₂ | SO₂Me | O | 1,3-dioxan-5-yl | |
| 6.83 | NO₂ | SO₂Et | O | 1,3-dioxan-5-yl | |
| 6.84 | NO₂ | Cl | O | 1,3-dioxan-5-yl | |
| 6.85 | Cl | SO₂Me | O | γ-butyrolacton-2-yl | |
| 6.86 | Cl | SO₂Et | O | γ-butyrolacton-2-yl | |
| 6.87 | Cl | Cl | O | γ-butyrolacton-2-yl | |
| 6.88 | Br | SO₂Me | O | γ-butyrolacton-2-yl | |
| 6.89 | Br | SO₂Et | O | γ-butyrolacton-2-yl | |
| 6.90 | Br | Cl | O | γ-butyrolacton-2-yl | |
| 6.91 | I | SO₂Me | O | γ-butyrolacton-2-yl | |
| 6.92 | I | SO₂Et | O | γ-butyrolacton-2-yl | |
| 6.93 | I | Cl | O | γ-butyrolacton-2-yl | |
| 6.94 | Me | SO₂Me | O | γ-butyrolacton-2-yl | |
| 6.95 | Me | SO₂Et | O | γ-butyrolacton-2-y1 | |

TABLE 6-continued

Compounds of the formula (I) according to the invention in which the substituents and symbols are as defined below:

$R^3 = H$  $Q = Q2$  $R^6 = H$
$R^7 = Et$  $R^8 = H$

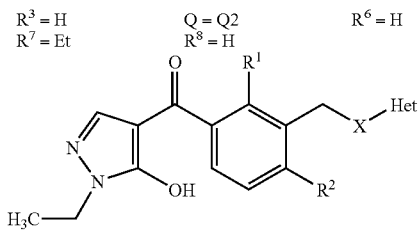

| No. | $R^1$ | $R^2$ | X | Het | Physical data |
|---|---|---|---|---|---|
| 6.96 | Me | Cl | O | γ-butyrolacton-2-yl | |
| 6.97 | SMe | SO$_2$Me | O | γ-butyrolacton-2-yl | |
| 6.98 | SMe | SO$_2$Et | O | γ-butyrolacton-2-yl | |
| 6.99 | SMe | Cl | O | γ-butyrolacton-2-yl | |
| 6.100 | SO$_2$Me | SO$_2$Me | O | γ-butyrolacton-2-yl | |
| 6.101 | SO$_2$Me | SO$_2$Et | O | γ-butyrolacton-2-yl | |
| 6.102 | SO$_2$Me | Cl | O | γ-butyrolacton-2-yl | |
| 6.103 | NO$_2$ | SO$_2$Me | O | γ-butyrolacton-2-Yl | |
| 6.104 | NO$_2$ | SO$_2$Et | O | γ-butyrolacton-2-yl | |
| 6.105 | NO$_2$ | Cl | O | γ-butyrolacton-2-yl | |
| 6.106 | Cl | SO$_2$Me | S | 3-tetrahydrofuranyl | |
| 6.107 | Cl | SO$_2$Et | S | 3-tetrahydrofuranyl | |
| 6.108 | Cl | Cl | S | 3-tetrahydrofuranyl | |
| 6.109 | Br | SO$_2$Me | S | 3-tetrahydrofuranyl | |
| 6.110 | Br | SO$_2$Et | S | 3-tetrahydrofuranyl | |
| 6.111 | Br | Cl | S | 3-tetrahydrofuranyl | |
| 6.112 | I | SO$_2$Me | S | 3-tetrahydrofuranyl | |
| 6.113 | I | SO$_2$Et | S | 3-tetrahydrofuranyl | |
| 6.114 | I | Cl | S | 3-tetrahydrofuranyl | |
| 6.115 | Me | SO$_2$Me | S | 3-tetrahydrofuranyl | |
| 6.116 | Me | SO$_2$Et | S | 3-tetrahydrofuranyl | |
| 6.117 | Me | Cl | S | 3-tetrahydrofuranyl | |
| 6.118 | SMe | SO$_2$Me | S | 3-tetrahydrofuranyl | |
| 6.119 | SMe | SO$_2$Et | S | 3-tetrahydrofuranyl | |
| 6.120 | SMe | Cl | S | 3-tetrahydrofuranyl | |
| 6.121 | SO$_2$Me | SO$_2$Me | S | 3-tetrahydrofuranyl | |
| 6.122 | SO$_2$Me | SO$_2$Et | S | 3-tetrahydrofuranyl | |
| 6.123 | SO$_2$Me | Cl | S | 3-tetrahydrofuranyl | |
| 6.124 | NO$_2$ | SO$_2$Me | S | 3-tetrahydrofuranyl | |
| 6.125 | NO$_2$ | SO$_2$Et | S | 3-tetrahydrofuranyl | |
| 6.126 | NO$_2$ | Cl | S | 3-tetrahydrofuranyl | |
| 6.127 | Cl | SO$_2$Me | S | 4-tetrahydropyfanyl | |
| 6.128 | Cl | SO$_2$Et | S | 4-tetrahydropyranyl | |
| 6.129 | Cl | Cl | S | 4-tetrahydropyranyl | |
| 6.130 | Br | SO$_2$Me | S | 4-tetrahydropyranyl | |
| 6.131 | Br | SO$_2$Et | S | 4-tetrahydropyranyl | |
| 6.132 | Br | Cl | S | 4-tetrahydropyranyl | |
| 6.133 | I | SO$_2$Me | S | 4-tetrahydropyranyl | |
| 6.134 | I | SO$_2$Et | S | 4-tetrahydropyranyl | |
| 6.135 | I | Cl | S | 4-tetrahydropyranyl | |
| 6.136 | Me | SO$_2$Me | S | 4-tetrahydropyranyl | |
| 6.137 | Me | SO$_2$Et | S | 4-tetrahydropyranyl | |
| 6.138 | Me | Cl | S | 4-tetrahydropyranyl | |
| 6.139 | SMe | SO$_2$Me | S | 4-tetrahydropyranyl | |
| 6.140 | SMe | SO$_2$Et | S | 4-tetrahydropyranyl | |
| 6.141 | SMe | Cl | S | 4-tetrahydropyranyl | |
| 6.142 | SO$_2$Me | SO$_2$Me | S | 4-tetrahydropyranyl | |
| 6.143 | SO$_2$Me | SO$_2$Et | S | 4-tetrahydropyranyl | |
| 6.144 | SO$_2$Me | Cl | S | 4-tetrahydropyranyl | |
| 6.145 | NO$_2$ | SO$_2$Me | S | 4-tetrahydropyranyl | |
| 6.146 | NO$_2$ | SO$_2$Et | S | 4-tetrahydropyranyl | |
| 6.147 | NO$_2$ | Cl | S | 4-tetrahydropyranyl | |
| 6.148 | Cl | SO$_2$Me | S | 3-tetrahydropyranyl | |
| 6.149 | Cl | SO$_2$Et | S | 3-tetrahydropyranyl | |
| 6.150 | Cl | Cl | S | 3-tetrahydropyranyl | |
| 6.151 | Br | SO$_2$Me | S | 3-tetrahydropyranyl | |
| 6.152 | Br | SO$_2$Et | S | 3-tetrahydropyranyl | |
| 6.153 | Br | Cl | S | 3-tetrahydropyranyl | |
| 6.154 | I | SO$_2$Me | S | 3-tetrahydropyranyl | |
| 6.155 | I | SO$_2$Et | S | 3-tetrahydropyranyl | |
| 6.156 | I | Cl | S | 3-tetrahydropyranyl | |
| 6.157 | Me | SO$_2$Me | S | 3-tetrahydropyranyl | |
| 6.158 | Me | SO$_2$Et | S | 3-tetrahydropyranyl | |
| 6.159 | Me | Cl | S | 3-tetrahydropyranyl | |
| 6.160 | SMe | SO$_2$Me | S | 3-tetrahydropyranyl | |
| 6.161 | SMe | SO$_2$Et | S | 3-tetrahydropyranyl | |
| 6.162 | SMe | Cl | S | 3-tetrahydropyranyl | |
| 6.163 | SO$_2$Me | SO$_2$Me | S | 3-tetrahydropyranyl | |
| 6.164 | SO$_2$Me | SO$_2$Et | S | 3-tetrahydropyranyl | |
| 6.165 | SO$_2$Me | Cl | S | 3-tetrahydropyranyl | |
| 6.166 | NO$_2$ | SO$_2$Me | S | 3-tetrahydropyranyl | |
| 6.167 | NO$_2$ | SO$_2$Et | S | 3-tetrahydropyranyl | |
| 6.168 | NO$_2$ | Cl | S | 3-tetrahydropyranyl | |
| 6.169 | Cl | SO$_2$Me | S | t3-dioxan-5-yl | |
| 6.170 | Cl | SO$_2$Et | S | 1,3-dioxan-5-yl | |
| 6.171 | Cl | Cl | S | 1,3-dioxan-5-yl | |
| 6.172 | Br | SO$_2$Me | S | 1,3-dioxan-5-yl | |
| 6.173 | Br | SO$_2$Et | S | 1,3-dioxan-5-yl | |
| 6.174 | Br | Cl | S | 1,3-dioxan-5-yl | |
| 6.175 | I | SO$_2$Me | S | 1,3-dioxan-5-yl | |
| 6.176 | I | SO$_2$Et | S | 1,3-dioxan-5-yl | |
| 6.177 | I | Cl | S | 1,3-dioxan-5-yl | |
| 6.178 | Me | SO$_2$Me | S | 1,3-dioxan-5-yl | |
| 6.179 | Me | SO$_2$Et | S | 1,3-dioxan-5-yl | |
| 6.180 | Me | Cl | S | 1,3-dioxan-5-yl | |
| 6.181 | SMe | SO$_2$Me | S | 1,3-dioxan-5-yl | |
| 6.182 | SMe | SO$_2$Et | S | 1,3-dioxan-5-yl | |
| 6.183 | SMe | Cl | S | 1,3-dioxan-5-yl | |
| 6.184 | SO$_2$Me | SO$_2$Me | S | 1,3-dioxan-5-yl | |
| 6.185 | SO$_2$Me | SO$_2$Et | S | 1,3-dioxan-5-yl | |
| 6.186 | SO$_2$Me | Cl | S | 1,3-dioxan-5-yl | |
| 6.187 | NO$_2$ | SO$_2$Me | S | 1,3-dioxan-5-yl | |
| 6.188 | NO$_2$ | SO$_2$Et | S | 1,3-dioxan-5-yl | |
| 6.189 | NO$_2$ | Cl | S | 1,3-dioxan-5-yl | |
| 6.190 | Cl | SO$_2$Me | S | γ-butyrolacton-2-yl | |
| 6.191 | Cl | SO$_2$Et | S | γ-butyrolacton-2-yl | |
| 6.192 | Cl | Cl | S | γ-butyrolacton-2-yl | |
| 6.193 | Br | SO$_2$Me | S | γ-butyrolacton-2-yl | |
| 6.194 | Br | SO$_2$Et | S | γ-butyrolacton-2-yl | |
| 6.195 | Br | Cl | S | γ-butyrolacton-2-yl | |
| 6.196 | I | SO$_2$Me | S | γ-butyrolacton-2-yl | |
| 6.197 | I | SO$_2$Et | S | γ-butyrolacton-2-yl | |
| 6.198 | I | Cl | S | γ-butyrolacton-2-yl | |
| 6.199 | Me | SO$_2$Me | S | γ-butyrolacton-2-yl | |
| 6.200 | Me | SO$_2$Et | S | γ-butyrolacton-2-yl | |
| 6.201 | Me | Cl | S | γ-butyrolacton-2-yl | |
| 6.202 | SMe | SO$_2$Me | S | γ-butyrolacton-2-yl | |
| 6.203 | SMe | SO$_2$Et | S | γ-butyrolacton-2-yl | |
| 6.204 | SMe | Cl | S | γ-butyrolacton-2-yl | |
| 6.205 | SO$_2$Me | SO$_2$Me | S | γ-butyrolacton-2-yl | |
| 6.206 | SO$_2$Me | SO$_2$Et | S | γ-butyrolacton-2-yl | |
| 6.207 | SO$_2$Me | Cl | S | γ-butyrolacton-2-yl | |
| 6.208 | NO$_2$ | SO$_2$Me | S | γ-butyrolacton-2-yl | |
| 6.209 | NO$_2$ | SO$_2$Et | S | γ-butyrolacton-2-yl | |
| 6.210 | NO$_2$ | Cl | S | γ-butyrolacton-2-yl | |

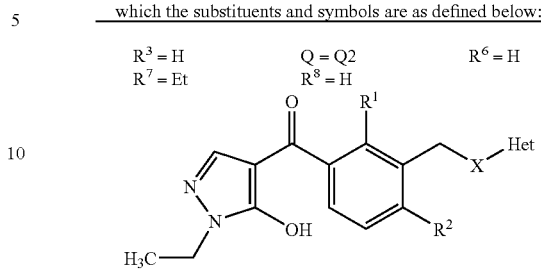

TABLE 7

Compounds of the formula (l) according to the invention in which the substituents and symbols are as defined below:

$R^3 = H$  $Q = Q2$  $R^7 = Me$
$R^8 = H$  $R^6 = $ cyclopropyl

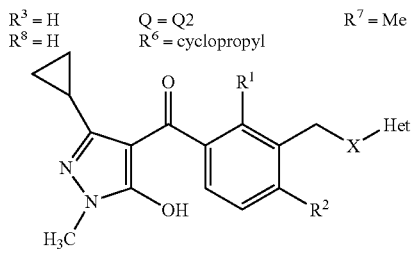

| No. | $R^1$ | $R^2$ | X | Het | Physical data |
|---|---|---|---|---|---|
| 7.1 | Cl | SO$_2$Me | O | 3-tetrahydrofuranyl | |
| 7.2 | Cl | SO$_2$Et | O | 3-tetrahydrofuranyl | |
| 7.3 | Cl | Cl | O | 3-tetrahydrofuranyl | |
| 7.4 | Br | SO$_2$Me | O | 3-tetrahydrofuranyl | |
| 7.5 | Br | SO$_2$Et | O | 3-tetrahydrofuranyl | |
| 7.6 | Br | Cl | O | 3-tetrahydrofuranyl | |
| 7.7 | I | SO$_2$Me | O | 3-tetrahydrofuranyl | |
| 7.8 | I | SO$_2$Et | O | 3-tetrahydrofuranyl | |
| 7.9 | I | Cl | O | 3-tetrahydrofuranyl | |
| 7.10 | Me | SO$_2$Me | O | 3-tetrahydrofuranyl | |
| 7.11 | Me | SO$_2$Et | O | 3-tetrahydrofuranyl | |
| 7.12 | Me | Cl | O | 3-tetrahydrofuranyl | |
| 7.13 | SMe | SO$_2$Me | O | 3-tetrahydrofuranyl | |
| 7.14 | SMe | SO$_2$Et | O | 3-tetrahydrofuranyl | |
| 7.15 | SMe | Cl | O | 3-tetrahydrofuranyl | |
| 7.16 | SO$_2$Me | SO$_2$Me | O | 3-tetrahydrofuranyl | |
| 7.17 | SO$_2$Me | SO$_2$Et | O | 3-tetrahydrofUranyl | |
| 7.18 | SO$_2$Me | Cl | O | 3-tetrahydrofuranyl | |
| 7.19 | NO$_2$ | SO$_2$Me | O | 3-tetrahydrofuranyl | |
| 7.20 | NO$_2$ | SO$_2$Et | O | 3-tetrahydrofuranyl | |
| 7.21 | NO$_2$ | Cl | O | 3-tetrahydrofuranyl | |
| 7.22 | Cl | SO$_2$Me | O | 4-tetrahydropyranyl | |
| 7.23 | Cl | SO$_2$Et | O | 4-tetrahydropyranyl | |
| 7.24 | Cl | Cl | O | 4-tetrahydropyranyl | |
| 7.25 | Br | SO$_2$Me | O | 4-tetrahydropyranyl | |
| 7.26 | Br | SO$_2$Et | O | 4-tetrahydropyranyl | |
| 7.27 | Br | Cl | O | 4-tetrahydropyranyl | |
| 7.28 | I | SO$_2$Me | O | 4-tetrahydropyranyl | |
| 7.29 | I | SO$_2$Et | O | 4-tetrahydropyranyl | |
| 7.30 | I | Cl | O | 4-tetrahydropyranyl | |
| 7.31 | Me | SO$_2$Me | O | 4-tetrahydropyranyl | |
| 7.32 | Me | SO$_2$Et | O | 4-tetrahydropyranyl | |
| 7.33 | Me | Cl | O | 4-tetrahydropyranyl | |
| 7.34 | SMe | SO$_2$Me | O | 4-tetrahydropyranyl | |
| 7.35 | SMe | SO$_2$Et | O | 4-tetrahydropyranyl | |
| 7.36 | SMe | Cl | O | 4-tetrahydropyranyl | |
| 7.37 | SO$_2$Me | SO$_2$Me | O | 4-tetrahydropyranyl | |
| 7.38 | SO$_2$Me | SO$_2$Et | O | 4-tetrahydropyranyl | |
| 7.39 | SO$_2$Me | Cl | O | 4-tetrahydropyranyl | |
| 7.40 | NO$_2$ | SO$_2$Me | O | 4-tetrahydropyranyl | |
| 7.41 | NO$_2$ | SO$_2$Et | O | 4-tetrahydropyranyl | |
| 7.42 | NO$_2$ | Cl | O | 4-tetrahydropyranyl | |
| 7.43 | Cl | SO$_2$Me | O | 3-tetrahydropyranyl | |
| 7.44 | Cl | SO$_2$Et | O | 3-tetrahydropyranyl | |
| 7.45 | Cl | Cl | O | 3-tetrahydropyranyl | |
| 7.46 | Br | SO$_2$Me | O | 3-tetrahydropyranyl | |
| 7.47 | Br | SO$_2$Et | O | 3-tetrahydropyranyl | |
| 7.48 | Br | Cl | O | 3-tetrahydropyranyl | |
| 7.49 | I | SO$_2$Me | O | 3-tetrahydropyranyl | |
| 7.50 | I | SO$_2$Et | O | 3-tetrahydropyranyl | |
| 7.51 | I | Cl | O | 3-tetrahydropyranyl | |
| 7.52 | Me | SO$_2$Me | O | 3-tetrahydropyranyl | |
| 7.53 | Me | SO$_2$Et | O | 3-tetrahydropyranyl | |
| 7.54 | Me | Cl | O | 3-tetrahydropyranyl | |
| 7.55 | SMe | SO$_2$Me | O | 3-tetrahydropyranyl | |
| 7.56 | SMe | SO$_2$Et | O | 3-tetrahydropyranyl | |
| 7.57 | SMe | Cl | O | 3-tetrahydropyranyl | |
| 7.58 | SO$_2$Me | SO$_2$Me | O | 3-tetrahydropyranyl | |
| 7.59 | SO$_2$Me | SO$_2$Et | O | 3-tetrahydropyranyl | |
| 7.60 | SO$_2$Me | Cl | O | 3-tetrahydropyranyl | |
| 7.61 | NO$_2$ | SO$_2$Me | O | 3-tetrahydropyranyl | |
| 7.62 | NO$_2$ | SO$_2$Et | O | 3-tetrahydropyranyl | |
| 7.63 | NO$_2$ | Cl | O | 3-tetrahydropyranyl | |
| 7.64 | Cl | SO$_2$Me | O | 1,3-dioxan-5-yl | |
| 7.65 | Cl | SO$_2$Et | O | 1,3-dioxan-5-yl | |
| 7.66 | Cl | Cl | O | 1,3-dioxan-5-yl | |
| 7.67 | Br | SO$_2$Me | O | 1,3-dioxan-5-yl | |
| 7.68 | Br | SO$_2$Et | O | 1,3-dioxan-5-yl | |
| 7.69 | Br | Cl | O | 1,3-dioxan-5-yl | |
| 7.70 | I | SO$_2$Me | O | 1,3-dioxan-5-yl | |
| 7.71 | I | SO$_2$Et | O | 1,3-dioxan-5-yl | |
| 7.72 | I | Cl | O | 1,3-dioxan-5-yl | |
| 7.73 | Me | SO$_2$Me | O | 1,3-dioxan-5-yl | |
| 7.74 | Me | SO$_2$Et | O | 1,3-dioxan-5-yl | |
| 7.75 | Me | Cl | O | 1,3-dioxan-5-yl | |
| 7.76 | SMe | SO$_2$Me | O | 1,3-dioxan-5-yl | |
| 7.77 | SMe | SO$_2$Et | O | 1,3-dioxan-5-yl | |
| 7.78 | SMe | Cl | O | 1,3-dioxan-5-yl | |
| 7.79 | SO$_2$Me | SO$_2$Me | O | 1,3-dioxan-5-yl | |
| 7.80 | SO$_2$Me | SO$_2$Et | O | 1,3-dioxan-5-yl | |
| 7.81 | SO$_2$Me | Cl | O | 1,3-dioxan-5-yl | |
| 7.82 | NO$_2$ | SO$_2$Me | O | 1,3-dioxan-5-yl | |
| 7.83 | NO$_2$ | SO$_2$Et | O | 1,3-dioxan-5-yl | |
| 7.84 | NO$_2$ | Cl | O | 1,3-dioxan-5-yl | |
| 7.85 | Cl | SO$_2$Me | O | γ-butyrolacton-2-yl | |
| 7.86 | Cl | SO$_2$Et | O | γ-butyrolacton-2-yl | |
| 7.87 | Cl | Cl | O | γ-butyrolacton-2-yl | |
| 7.88 | Br | SO$_2$Me | O | γ-butyrolacton-2-yl | |
| 7.89 | Br | SO$_2$Et | O | γ-butyrolacton-2-yl | |
| 7.90 | Br | Cl | O | γ-butyrolacton-2-yl | |
| 7.91 | I | SO$_2$Me | O | γ-butyrolacton-2-yl | |
| 7.92 | I | SO$_2$Et | O | γ-butyrolacton-2-yl | |
| 7.93 | I | Cl | O | γ-butyrolacton-2-yl | |
| 7.94 | Me | SO$_2$Me | O | γ-butyrolacton-2-yl | |
| 7.95 | Me | SO$_2$Et | O | γ-butyrolacton-2-yl | |
| 7.96 | Me | Cl | O | γ-butyrolacton-2-yl | |
| 7.97 | SMe | SO$_2$Me | O | γ-butyrolacton-2-yl | |
| 7.98 | SMe | SO$_2$Et | O | γ-butyrolacton-2-yl | |
| 7.99 | SMe | Cl | O | γ-butyrolacton-2-yl | |
| 7.100 | SO$_2$Me | SO$_2$Me | O | γ-butyrolacton-2-yl | |
| 7.101 | SO$_2$Me | SO$_2$Et | O | γ-butyrolacton-2-yl | |
| 7.102 | SO$_2$Me | Cl | O | γ-butyrolacton-2-Yl | |
| 7.103 | NO$_2$ | SO$_2$Me | O | γ-butyrolacton-2-yl | |
| 7.104 | NO$_2$ | SO$_2$Et | O | γ-butyrolacton-2-Yl | |
| 7.105 | NO$_2$ | Cl | O | γ-butyrolacton-2-yl | |
| 7.106 | Cl | SO$_2$Me | S | 3-tetrahydrofuranyl | |
| 7.107 | Cl | SO$_2$Et | S | 3-tetrahydrofuranyl | |
| 7.108 | Cl | Cl | S | 3-tetrahydrofuranyl | |
| 7.109 | Br | SO$_2$Me | S | 3-tetrahydrofuranyl | |
| 7.110 | Br | SO$_2$Et | S | 3-tetrahydrofuranyl | |
| 7.111 | Br | Cl | S | 3-tetrahydrofuranyl | |
| 7.112 | I | SO$_2$Me | S | 3-tetrahydrofuranyl | |
| 7.113 | I | SO$_2$Et | S | 3-tetrahydrofuranyl | |
| 7.114 | I | Cl | S | 3-tetrahydrofuranyl | |
| 7.115 | Me | SO$_2$Me | S | 3-tetrahydrofuranyl | |
| 7.116 | Me | SO$_2$Et | S | 3-tetrahydrofuranyl | |
| 7.117 | Me | Cl | S | 3-tetrahydrofuranyl | |
| 7.118 | SMe | SO$_2$Me | S | 3-tetrahydrofuranyl | |
| 7.119 | SMe | SO$_2$Et | S | 3-tetrahydrofuranyl | |
| 7.120 | SMe | Cl | S | 3-tetrahydrofuranyl | |
| 7.121 | SO$_2$Me | SO$_2$Me | S | 3-tetrahydrofuranyl | |
| 7.122 | SO$_2$Me | SO$_2$Et | S | 3-tetrahydrofuranyl | |

TABLE 7-continued

Compounds of the formula (I) according to the invention in which the substituents and symbols are as defined below:

$R^3 = H$  $Q = Q2$  $R^7 = Me$
$R^8 = H$  $R^6 = $ cyclopropyl

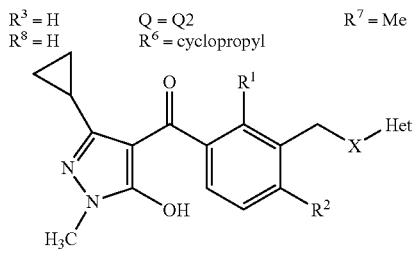

| No. | $R^1$ | $R^2$ | X | Het | Physical data |
|---|---|---|---|---|---|
| 7.123 | SO$_2$Me | Cl | S | 3-tetrahydrofuranyl | |
| 7.124 | NO$_2$ | SO$_2$Me | S | 3-tetrahydrofuranyl | |
| 7.125 | NO$_2$ | SO$_2$Et | S | 3-tetrahydrofuranyl | |
| 7.126 | NO$_2$ | Cl | S | 3-tetrahydrofuranyl | |
| 7.127 | Cl | SO$_2$Me | S | 4-tetrahydropyranyl | |
| 7.128 | Cl | SO$_2$Et | S | 4-tetrahydropyranyl | |
| 7.129 | Cl | Cl | S | 4-tetrahydropyranyl | |
| 7.130 | Br | SO$_2$Me | S | 4-tetrahydropyranyl | |
| 7.131 | Br | SO$_2$Et | S | 4-tetrahydropyranyl | |
| 7.132 | Br | Cl | S | 4-tetrahydropyranyl | |
| 7.133 | I | SO$_2$Me | S | 4-tetrahydropyranyl | |
| 7.134 | I | SO$_2$Et | S | 4-tetrahydropyranyl | |
| 7.135 | I | Cl | S | 4-tetrahydropyranyl | |
| 7.136 | Me | SO$_2$Me | S | 4-tetrahydropyranyl | |
| 7.137 | Me | SO$_2$Et | S | 4-tetrahydropyranyl | |
| 7.138 | Me | Cl | S | 4-tetrahydropyranyl | |
| 7.139 | SMe | SO$_2$Me | S | 4-tetrahydropyranyl | |
| 7.140 | SMe | SO$_2$Et | S | 4-tetrahydropyranyl | |
| 7.141 | SMe | Cl | S | 4-tetrahydropyranyl | |
| 7.142 | SO$_2$Me | SO$_2$Me | S | 4-tetrahydropyranyl | |
| 7.143 | SO$_2$Me | SO$_2$Et | S | 4-tetrahydropyranyl | |
| 7.144 | SO$_2$Me | Cl | S | 4-tetrahydropyranyl | |
| 7.145 | NO$_2$ | SO$_2$Me | S | 4-tetrahydropyranyl | |
| 7.146 | NO$_2$ | SO$_2$Et | S | 4-tetrahydropyranyl | |
| 7.147 | NO$_2$ | Cl | S | 4-tetrahydropyranyl | |
| 7.148 | Cl | SO$_2$Me | S | 3-tetrahydropyranyl | |
| 7.149 | Cl | SO$_2$Et | S | 3-tetrahydropyranyl | |
| 7.150 | Cl | Cl | S | 3-tetrahydropyranyl | |
| 7.151 | Br | SO$_2$Me | S | 3-tetrahydropyranyl | |
| 7.152 | Br | SO$_2$Et | S | 3-tetrahydropyranyl | |
| 7.153 | Br | Cl | S | 3-tetrahydropyranyl | |
| 7.154 | I | SO$_2$Me | S | 3-tetrahydropyranyl | |
| 7.155 | I | SO$_2$Et | S | 3-tetrahydropyranyl | |
| 7.156 | I | Cl | S | 3-tetrahydropyranyl | |
| 7.157 | Me | SO$_2$Me | S | 3-tetrahydropyranyl | |
| 7.158 | Me | SO$_2$Et | S | 3-tetrahydropyranyl | |
| 7.159 | Me | Cl | S | 3-tetrahydropyranyl | |
| 7.160 | SMe | SO$_2$Me | S | 3-tetrahydropyranyl | |
| 7.161 | SMe | SO$_2$Et | S | 3-tetrahydropyranyl | |
| 7.162 | SMe | Cl | S | 3-tetrahydropyranyl | |
| 7.163 | SO$_2$Me | SO$_2$Me | S | 3-tetrahydropyranyl | |
| 7.164 | SO$_2$Me | SO$_2$Et | S | 3-tetrahydropyranyl | |
| 7.165 | SO$_2$Me | Cl | S | 3-tetrahydropyranyl | |
| 7.166 | NO$_2$ | SO$_2$Me | S | 3-tetrahydropyranyl | |
| 7.167 | NO$_2$ | SO$_2$Et | S | 3-tetrahydropyranyl | |
| 7.168 | NO$_2$ | Cl | S | 3-tetrahydropyranyl | |
| 7.169 | Cl | SO$_2$Me | S | 1,3-dioxan-5-yl | |
| 7.170 | Cl | SO$_2$Et | S | 1,3-dioxan-5-yl | |
| 7.171 | Cl | Cl | S | 1,3-dioxan-5-yl | |
| 7.172 | Br | SO$_2$Me | S | 1,3-dioxan-5-yl | |
| 7.173 | Br | SO$_2$Et | S | 1,3-dioxan-5-yl | |
| 7.174 | Br | Cl | S | 1,3-dioxan-5-yl | |
| 7.175 | I | SO$_2$Me | S | 1,3-dioxan-5-yl | |
| 7.176 | I | SO$_2$Et | S | 1,3-dioxan-5-yl | |
| 7.177 | I | Cl | S | 1,3-dioxan-5-yl | |
| 7.178 | Me | SO$_2$Me | S | 1,3-dioxan-5-yl | |
| 7.179 | Me | SO$_2$Et | S | 1,3-dioxan-5-yl | |
| 7.180 | Me | Cl | S | 1,3-dioxan-5-yl | |
| 7.181 | SMe | SO$_2$Me | S | 1,3-dioxan-5-yl | |
| 7.182 | SMe | SO$_2$Et | S | 1,3-dioxan-5-yl | |
| 7.183 | SMe | Cl | S | 1,3-dioxan-5-yl | |

TABLE 7-continued

Compounds of the formula (I) according to the invention in which the substituents and symbols are as defined below:

$R^3 = H$  $Q = Q2$  $R^7 = Me$
$R^8 = H$  $R^6 = $ cyclopropyl

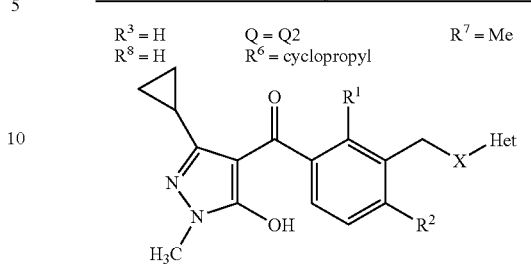

| No. | $R^1$ | $R^2$ | X | Het | Physical data |
|---|---|---|---|---|---|
| 7.184 | SO$_2$Me | SO$_2$Me | S | 1,3-dioxan-5-yl | |
| 7.185 | SO$_2$Me | SO$_2$Et | S | 1,3-dioxan-5-yl | |
| 7.186 | SO$_2$Me | Cl | S | 1,3-dioxan-5-yl | |
| 7.187 | NO$_2$ | SO$_2$Me | S | 1,3-dioxan-5-yl | |
| 7.188 | NO$_2$ | SO$_2$Et | S | 1,3-d,oxan-5-yl | |
| 7.189 | NO$_2$ | Cl | S | 1,3-dioxan-5-yl | |
| 7.190 | Cl | SO$_2$Me | S | γ-butyrolacton-2-yl | |
| 7.191 | Cl | SO$_2$Et | S | γ-butyrolacton-2-yl | |
| 7.192 | Cl | Cl | S | γ-butyrolacton-2-yl | |
| 7.193 | Br | SO$_2$Me | S | γ-butyrolacton-2-yl | |
| 7.194 | Br | SO$_2$Et | S | γ-butyrolacton-2-yl | |
| 7.195 | Br | Cl | S | γ-butyrolacton-2-yl | |
| 7.196 | I | SO$_2$Me | S | γ-butyrolacton-2-yl | |
| 7.197 | I | SO$_2$Et | S | γ-butyrolacton-2-yl | |
| 7.198 | I | Cl | S | γ-butyrolacton-2-yl | |
| 7.199 | Me | SO$_2$Me | S | γ-butyrolacton-2-yl | |
| 7.200 | Me | SO$_2$Et | S | γ-butyrolacton-2-yl | |
| 7.201 | Me | Cl | S | γ-butyrolacton-2-yl | |
| 7.202 | SMe | SO$_2$Me | S | γ-butyrolacton-2-yl | |
| 7.203 | SMe | SO$_2$Et | S | γ-butyrolacton-2-yl | |
| 7.204 | SMe | Cl | S | γ-butyrolacton-2-yl | |
| 7.205 | SO$_2$Me | SO$_2$Me | S | γ-butyrolacton-2-yl | |
| 7.206 | SO$_2$Me | SO$_2$Et | S | γ-butyrolacton-2-yl | |
| 7.207 | SO$_2$Me | Cl | S | γ-butyrolacton-2-yl | |
| 7.208 | NO$_2$ | SO$_2$Me | S | γ-butyrolacton-2-yl | |
| 7.209 | NO$_2$ | SO$_2$Et | S | γ-butyrolacton-2-yl | |
| 7.210 | NO$_2$ | Cl | S | γ-butyrolacton-2-yl | |

TABLE 8

Compounds of the formula (I) according to the invention in which the substituents and symbols are as defined below:

$R^1 = Cl$  $R_2 = SO_2Me$  $R^3 = H$
$Q = Q2$  $X = O$

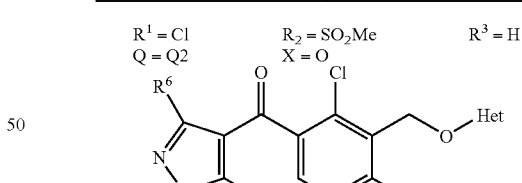

| No. | $R^6$ | $R^7$ | $R^8$ | Het | Physical data |
|---|---|---|---|---|---|
| 8.1 | H | Me | SOMe | 3-tetrahydrofuranyl | |
| 8.2 | H | Me | SOMe | 3-tetrahydrofuranyl | |
| 8.3 | H | Me | SO$_2$-nPr | 3-tetrahydrofuranyl | |
| 8.4 | H | Me | SO$_2$-nBu | 3-tetrahydrofuranyl | |
| 8.5 | H | Me | SO$_2$Ph | 3-tetrahydrofuranyl | |
| 8.6 | H | Me | CO$_2$Me | 3-tetrahydrofuranyl | |
| 8.7 | H | Me | CO$_2$Et | 3-tetrahydrofuranyl | |
| 8.8 | H | Me | CO$_2$-nPr | 3-tetrahydrofuranyl | |
| 8.9 | H | Me | CO$_2$nBu | 3-tetrahydrofuranyl | |
| 8.10 | H | Me | CO$_2$Ph | 3-tetrahydrofuranyl | |
| 8.11 | H | Me | Me | 3-tetrahydrofuranyl | |
| 8.12 | H | Me | Et | 3-tetrahydrofuranyl | |

TABLE 8-continued

Compounds of the formula (I) according to the invention in which the substituents and symbols are as defined below:

R¹ = Cl, R₂ = SO₂Me, R³ = H, Q = Q2, X = O

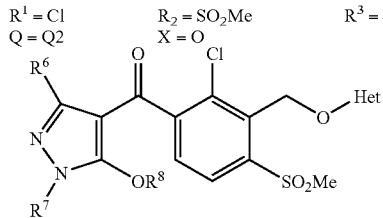

| No. | R⁶ | R⁷ | R⁸ | Het | Physical data |
|---|---|---|---|---|---|
| 8.13 | H | Me | nPr | 3-tetrahydrofuranyl | |
| 8.14 | H | Me | nBu | 3-tetrahydrofuranyl | |
| 8.15 | Me | Me | SOMe | 3-tetrahydrofuranyl | |
| 8.16 | Me | Me | SOMe | 3-tetrahydrofuranyl | |
| 8.17 | Me | Me | SO₂-nPr | 3-tetrahydrofuranyl | |
| 8.18 | Me | Me | SO₂-nBu | 3-tetrahydrofuranyl | |
| 8.19 | Me | Me | SO₂Ph | 3-tetrahydrofuranyl | |
| 8.20 | Me | Me | CO₂Me | 3-tetrahydrofuranyl | |
| 8.21 | Me | Me | CO₂Et | 3-tetrahydrofuranyl | |
| 8.22 | Me | Me | CO₂-nPr | 3-tetrahydrofuranyl | |
| 8.23 | Me | Me | CO₂-nBu | 3-tetrahydrofuranyl | |
| 8.24 | Me | Me | CO₂Ph | 3-tetrahydrofuranyl | |
| 8.25 | Me | Me | Me | 3-tetrahydrofuranyl | |
| 8.26 | Me | Me | Et | 3-tetrahydrofuranyl | |
| 8.27 | Me | Me | nPr | 3-tetrahydrofuranyl | |
| 8.28 | Me | Me | nBu | 3-tetrahydrofuranyl | |
| 8.29 | H | Et | SOMe | 3-tetrahydrofuranyl | |
| 8.30 | H | Et | SOMe | 3-tetrahydrofuranyl | |
| 8.31 | H | Et | SO₂-nPr | 3-tetrahydrofuranyl | |
| 8.32 | H | Et | SO₂-nBu | 3-tetrahydrofuranyl | |
| 8.33 | H | Et | SO₂Ph | 3-tetrahydrofuranyl | |
| 8.34 | H | Et | CO₂Me | 3-tetrahydrofuranyl | |
| 8.35 | H | Et | CO₂Et | 3-tetrahydrofuranyl | |
| 8.36 | H | Et | CO₂-nPr | 3-tetrahydrofuranyl | |
| 8.37 | H | Et | CO₂-nBu | 3-tetrahydrofuranyl | |
| 8.38 | H | Et | CO₂Ph | 3-tetrahydrofuranyl | |
| 8.39 | H | Et | Me | 3-tetrahydrofuranyl | |
| 8.40 | H | Et | Et | 3-tetrahydrofuranyl | |
| 8.41 | H | Et | nPr | 3-tetrahydrofuranyl | |
| 8.42 | H | Et | nBu | 3-tetrahydrofuranyl | |
| 8.43 | cPr | Me | SOMe | 3-tetrahydrofuranyl | |
| 8.44 | cPr | Me | SOMe | 3-tetrahydrofuranyl | |
| 8.45 | cPr | Me | SO₂-nPr | 3-tetrahydrofuranyl | |
| 8.46 | cPr | Me | SO₂-nBu | 3-tetrahydrofuranyl | |
| 8.47 | cPr | Me | SO₂Ph | 3-tetrahydrofurafyl | |
| 8.48 | cPr | Me | CO₂Me | 3-tetrahydrofuranyl | |
| 8.49 | cPr | Me | CO₂Et | 3-tetrahydrofuranyl | |
| 8.50 | cPr | Me | CO₂-nPr | 3-tetrahydrofuranyl | |
| 8.51 | cPr | Me | CO₂-nBu | 3-tetrahydrofuranyl | |
| 8.52 | cPr | Me | CO₂Ph | 3-tetrahydrofuranyl | |
| 8.53 | cPr | Me | Me | 3-tetrahydrofuranyl | |
| 8.54 | cPr | Me | Et | 3-tetrahydrofuranyl | |
| 8.55 | cPr | Me | nPr | 3-tetrahydrofuranyl | |
| 8.56 | cPr | Me | nBu | 3-tetrahydrofuranyl | |
| 8.57 | H | Me | SOMe | 3-tetrahydropyranyl | |
| 8.58 | H | Me | SOMe | 3-tetrahydropyranyl | |
| 8.59 | H | Me | SO₂-nPr | 3-tetrahydropyranyl | |
| 8.60 | H | Me | SO₂-nBu | 3-tetrahydropyranyl | |
| 8.61 | H | Me | SO₂Ph | 3-tetrahydropyranyl | |
| 8.62 | H | Me | CO₂Me | 3-tetrahydropyranyl | |
| 8.63 | H | Me | CO₂Et | 3-tetrahydropyranyl | |
| 8.64 | H | Me | CO₂-nPr | 3-tetrahydropyranyl | |
| 8.65 | H | Me | CO₂-nBu | 3-tetrahydropyranyl | |
| 8.66 | H | Me | CO₂Ph | 3-tetrahydropyranyl | |
| 8.67 | H | Me | Me | 3-tetrahydropyranyl | |
| 8.68 | H | Me | Et | 3-tetrahydropyranyl | |
| 8.69 | H | Me | nPr | 3-tetrahydropyranyl | |
| 8.70 | H | Me | nBu | 3-tetrahydropyranyl | |
| 8.71 | Me | Me | SOMe | 3-tetrahydropyranyl | |
| 8.72 | Me | Me | SOMe | 3-tetrahydropyranyl | |
| 8.73 | Me | Me | SO₂-nPr | 3-tetrahydropyranyl | |
| 8.74 | Me | Me | SO₂-nBu | 3-tetrahydropyranyl | |
| 8.75 | Me | Me | SO₂Ph | 3-tetrahydropyranyl | |
| 8.76 | Me | Me | CO₂Me | 3-tetrahydropyranyl | |
| 8.77 | Me | Me | CO₂Et | 3-tetrahydropyranyl | |
| 8.78 | Me | Me | CO₂-nPr | 3-tetrahydropyranyl | |
| 8.79 | Me | Me | CO₂-nBu | 3-tetrahydropyranyl | |
| 8.80 | Me | Me | CO₂Ph | 3-tetrahydropyranyl | |
| 8.81 | Me | Me | Me | 3-tetrahydropyranyl | |
| 8.82 | Me | Me | Et | 3-tetrahydropyranyl | |
| 8.83 | Me | Me | nPr | 3-tetrahydropyranyl | |
| 8.84 | Me | Me | nBu | 3-tetrahydropyranyl | |
| 8.85 | H | Et | SOMe | 3-tetrahydropyranyl | |
| 8.86 | H | Et | SOMe | 3-tetrahydropyranyl | |
| 8.87 | H | Et | SO₂-nPr | 3-tetrahydropyranyl | |
| 8.88 | H | Et | SO₂-nBu | 3-tetrahydropyranyl | |
| 8.89 | H | Et | SO₂Ph | 3-tetrahydropyranyl | |
| 8.90 | H | Et | CO₂Me | 3-tetrahydropyranyl | |
| 8.91 | H | Et | CO₂Et | 3-tetrahydropyranyl | |
| 8.92 | H | Et | CO₂-nPr | 3-tetrahydropyranyl | |
| 8.93 | H | Et | CO₂-nBu | 3-tetrahydropyranyl | |
| 8.94 | H | Et | CO₂Ph | 3-tetrahydropyranyl | |
| 8.95 | H | Et | Me | 3-tetrahydropyranyl | |
| 8.96 | H | Et | Et | 3-tetrahydropyranyl | |
| 8.97 | H | Et | nPr | 3-tetrahydropyranyl | |
| 8.98 | H | Et | nBu | 3-tetrahydropyranyl | |
| 8.99 | cPr | Me | SOMe | 3-tetrahydropyranyl | |
| 8.100 | cPr | Me | SOMe | 3-tetrahydropyranyl | |
| 8.101 | cPr | Me | SO₂-nPr | 3-tetrahydropyranyl | |
| 8.102 | cPr | Me | SO₂-nBu | 3-tetrahydropyranyl | |
| 8.103 | cPr | Me | SO₂Ph | 3-tetrahydropyranyl | |
| 8.104 | cPr | Me | CO₂Me | 3-tetrahydropyranyl | |
| 8.105 | cPr | Me | CO₂Et | 3-tetrahydropyranyl | |
| 8.106 | cPr | Me | CO₂-nPr | 3-tetrahydropyranyl | |
| 8.107 | cPr | Me | CO₂-nBu | 3-tetrahydropyranyl | |
| 8.108 | cPr | Me | CO₂Ph | 3-tetrahydropyranyl | |
| 8.109 | cPr | Me | Me | 3-tetrahydropyranyl | |
| 8.110 | cPr | Me | Et | 3-tetrahydropyranyl | |
| 8.111 | cPr | Me | nPr | 3-tetrahydropyranyl | |
| 8.112 | cPr | Me | nBu | 3-tetrahydropyranyl | |
| 8.113 | H | Me | SOMe | 1,3-dioxan-5-yl | |
| 8.114 | H | Me | SOMe | 1,3-dioxan-5-yl | |
| 8.115 | H | Me | SO₂-nPr | 1,3-dioxan-5-yl | |
| 8.116 | H | Me | SO₂-nBu | 1,3-dioxan-5-yl | |
| 8.117 | H | Me | SO₂Ph | 1,3-dioxan-5-yl | |
| 8.118 | H | Me | CO₂Me | 1,3-dioxan-5-yl | |
| 8.119 | H | Me | CO₂Et | 1,3-dioxan-5-yl | |
| 8.120 | H | Me | CO₂-nPr | 1,3-dioxan-5-yl | |
| 8.121 | H | Me | CO₂-nBu | 1,3-dioxan-5-yl | |
| 8.122 | H | Me | CO₂Ph | 1,3-dioxan-5-yl | |
| 8.123 | H | Me | Me | 1,3-dioxan-5-yl | |
| 8.124 | H | Me | Et | 1,3-dioxan-5-yl | |
| 8.125 | H | Me | nPr | 1,3-dioxan-5-yl | |
| 8.126 | H | Me | nBu | 1,3-dioxan-5-yl | |
| 8.127 | Me | Me | SOMe | 1,3-dioxan-5-yl | |
| 8.128 | Me | Me | SOMe | 1,3-dioxan-5-yl | |
| 8.129 | Me | Me | SO₂-nPr | 1,3-dioxan-5-yl | |
| 8.130 | Me | Me | SO₂-nBu | 1,3-dioxan-5-yl | |
| 8.131 | Me | Me | SO₂Ph | 1,3-dioxan-5-yl | |
| 8.132 | Me | Me | CO₂Me | 1,3-dioxan-5-yl | |
| 8.133 | Me | Me | CO₂Et | 1,3-dioxan-5-yl | |
| 8.134 | Me | Me | CO₂-nPr | 1,3-dioxan-5-yl | |
| 8.135 | Me | Me | CO₂-nBu | 1,3-dioxan-5-yl | |
| 8.136 | Me | Me | CO₂Ph | 1,3-dioxan-5-yl | |

TABLE 8-continued

Compounds of the formula (I) according to the invention in which the substituents and symbols are as defined below:

R¹ = Cl  R₂ = SO₂Me  R³ = H
Q = Q2  X = O

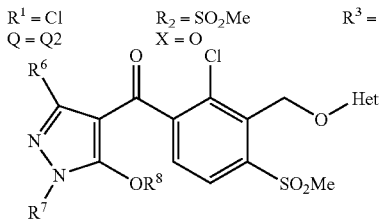

| No. | R⁶ | R⁷ | R⁸ | Het | Physical data |
|---|---|---|---|---|---|
| 8.137 | Me | Me | Me | 1,3-dioxan-5-yl | |
| 8.138 | Me | Me | Et | 1,3-dioxan-5-yl | |
| 8.139 | Me | Me | nPr | 1,3-dioxan-5-yl | |
| 8.140 | Me | Me | nBu | 1,3-dioxan-5-yl | |
| 8.141 | H | Et | SOMe | 1,3-dioxan-5-yl | |
| 8.142 | H | Et | SOMe | 1,3-dioxan-5-yl | |
| 8.143 | H | Et | SO₂-nPr | 1,3-dioxan-5-yl | |
| 8.144 | H | Et | SO₂-nBu | 1,3-dioxan-5-yl | |
| 8.145 | H | Et | SO₂Ph | 1,3-dioxan-5-yl | |
| 8.146 | H | Et | CO₂Me | 1,3-dioxan-5-yl | |
| 8.147 | H | Et | CO₂Et | 1,3-dioxan-5-yl | |
| 8.148 | H | Et | CO₂-nPr | 1,3-dioxan-5-yl | |
| 8.149 | H | Et | CO₂-nBu | 1,3-dioxan-5-yl | |
| 8.150 | H | Et | CO₂Ph | 1,3-dioxan-5-y1 | |
| 8.151 | H | Et | Me | 1,3-dioxan-5-yl | |
| 8.152 | H | Et | Et | 1,3-dioxan-5-yl | |
| 8.153 | H | Et | nPr | 1,3-dioxan-5-yl | |
| 8.154 | H | Et | nBu | 1,3-dioxan-5-yl | |
| 8.155 | cPr | Me | SOMe | 1,3-dioxan-5-yl | |
| 8.156 | cPr | Me | SOMe | 1,3-dioxan-5-yl | |
| 8.157 | cPr | Me | SO₂-nPr | 1,3-dioxan-5-yl | |
| 8.158 | cPr | Me | SO₂-nBu | 1,3-dioxan-5-yl | |
| 8.159 | cPr | Me | SO₂Ph | 1,3-dioxan-5-yl | |
| 8.160 | cPr | Me | CO₂Me | 1,3-dioxan-5-yt | |
| 8.161 | cPr | Me | CO₂Et | 1,3-dioxan-5-yl | |
| 8.162 | cPr | Me | CO₂-nPr | 1,3-dioxan-5-yl | |
| 8.163 | cPr | Me | CO₂-nBu | 1,3-dioxan-5-yl | |
| 8.164 | cPr | Me | CO₂Ph | 1,3-dioxan-5-yl | |
| 8.165 | cPr | Me | Me | 1,3-dioxan-5-yl | |
| 8.166 | cPr | Me | Et | 1,3-dioxan-5-yl | |
| 8.167 | cPr | Me | nPr | 1,3-dioxan-5-yl | |
| 8.168 | cPr | Me | nBu | 1,3-dioxan-5-yl | |
| 8.169 | H | Me | SOMe | γ-butyrolacton-2-yl | |
| 8.170 | H | Me | SOMe | γ-butyrolacton-2-yl | |
| 8.171 | H | Me | SO₂-nPr | γ-butyrolacton-2-yl | |
| 8.172 | H | Me | SO₂-nBu | γ-butyrolacton-2-yl | |
| 8.173 | H | Me | SO₂Ph | γ-butyrolacton-2-yt | |
| 8.174 | H | Me | CO₂Me | γ-butyrolacton-2-yl | |
| 8.175 | H | Me | CO₂Et | γ-butyrolacton-2-yl | |
| 8.176 | H | Me | CO₂-nPr | γ-butyrolacton-2-yl | |
| 8.177 | H | Me | CO₂-nBu | γ-butyrolacton-2-yl | |
| 8.178 | H | Me | CO₂Ph | γ-bulyrolacton-2-yl | |
| 8.179 | H | Me | Me | γ-butyrolacton-2-yl | |
| 8.180 | H | Me | ET | γ-butyrolacton-2-yl | |
| 8.181 | H | Me | nPr | γ-bulyrolacton-2-yl | |
| 8.182 | H | Me | nBu | γ-butyrolacton-2-yl | |
| 8.183 | Me | Me | SOMe | γ-butyrolacton-2-yl | |
| 8.184 | Me | Me | SOMe | γ-butyrolacton-2-yl | |
| 8.185 | Me | Me | SO₂-nPr | γ-butyrolacton-2-yl | |
| 8.186 | Me | Me | SO₂-nBu | γ-butyrolacton-2-yl | |
| 8.187 | Me | Me | SO₂Ph | γ-butyrolacton-2-yl | |
| 8.188 | Me | Me | CO₂Me | γ-butyrolacton-2-yl | |
| 8.189 | Me | Me | CO₂Et | γ-butyrolacton-2-yl | |
| 8.190 | Me | Me | CO₂-nPr | γ-butyrolacton-2-yl | |
| 8.191 | Me | Me | CO₂-nBu | γ-butyrolacton-2-yl | |
| 8.192 | Me | Me | CO₂Ph | γ-butyrolacton-2-yl | |
| 8.193 | Me | Me | Me | γ-butyrolacton-2-yl | |
| 8.194 | Me | Me | Et | γ-butyrolacton-2-yl | |
| 8.195 | Me | Me | nPr | γ-butyrolacton-2-yl | |
| 8.196 | Me | Me | nBu | γ-butyrolacton-2-yl | |
| 8.197 | H | Et | SOMe | γ-butyrolacton-2-yl | |
| 8.198 | H | Et | SOMe | γ-butyrolacton-2-yl | |

TABLE 8-continued

Compounds of the formula (I) according to the invention in which the substituents and symbols are as defined below:

R¹ = Cl  R₂ = SO₂Me  R³ = H
Q = Q2  X = O

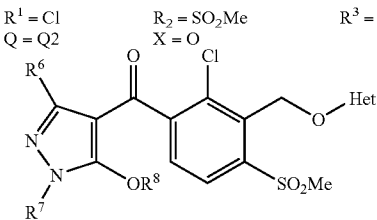

| No. | R⁶ | R⁷ | R⁸ | Het | Physical data |
|---|---|---|---|---|---|
| 8.199 | H | Et | SO₂-nPr | γ-butyrolacton-2-yl | |
| 8.200 | H | Et | SO₂-nBu | γ-butyrolacton-2-yl | |
| 8.201 | H | Et | SO₂Ph | γ-butyrolacton-2-yl | |
| 8.202 | H | Et | CO₂Me | γ-butyrolacton-2-yl | |
| 8.203 | H | Et | CO₂Et | γ-butyrolacton-2-yl | |
| 8.204 | H | Et | CO₂-nPr | γ-butyrolacton-2-yl | |
| 8.205 | H | Et | CO₂-nBu | γ-butyrolacton-2-yl | |
| 8.206 | H | Et | CO₂Ph | γ-butyrolacton-2-yl | |
| 8.207 | H | Et | Me | γ-butyrolacton-2-yl | |
| 8.208 | H | Et | Et | γ-butyrolacton-2-yl | |
| 8.209 | H | Et | nPr | γ-butyrolacton-2-yl | |
| 8.210 | H | Et | nBu | γ-butyrolacton-2-yl | |
| 8.211 | cPr | Me | SOMe | γ-butyrolacton-2-yl | |
| 8.212 | cPr | Me | SOMe | γ-butyrolacton-2-yl | |
| 8.213 | cPr | Me | SO₂-nPr | γ-butyrolacton-2-yl | |
| 8.214 | cPr | Me | SO₂-nBu | γ-butyrolacton-2-yl | |
| 8.215 | cPr | Me | SO₂Ph | γ-butyrolacton-2-yl | |
| 8.216 | cPr | Me | CO₂Me | γ-butyrolacton-2-yl | |
| 8.217 | cPr | Me | CO₂Et | γ-butyrolacton-2-yl | |
| 8.218 | cPr | Me | CO₂-nPr | γ-butyrolacton-2-yl | |
| 8.219 | cPr | Me | CO₂-nBu | γ-butyrolacton-2-yl | |
| 8.220 | cPr | Me | CO₂Ph | γ-butyrolacton-2-yl | |
| 8.221 | cPr | Me | Me | γ-butyrolacton 2-yl | |
| 8.222 | cPr | Me | Et | γ-butyrolacton 2-yl | |
| 8.223 | cPr | Me | nPr | γ-butyrolacton 2-yl | |
| 8.224 | cPr | Me | nBu | γ-butyrolacton 2-yl | |

B. FORMULATION EXAMPLES

1. Dusts

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing parts by weight of a compound of the formula (I), 64 parts by weight of kaolin-containing quartz as inert substance, 10 parts by weight of potassium lignosulfonate and 1 part by weight of sodium oleoylmethyltaurate as wetter and dispersant and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range, for example, approx. 255 to over 277° C.) and grinding the mixture in a friction ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-dispersible Granules

Water-dispersible granules are obtained by mixing 75 parts by weight of a compound of the formula (I),
10 " of calcium lignosulfonate,
5 " of sodium lauryl sulfate,
3 " of polyvinyl alcohol and
7 " of kaolin, grinding the mixture in a pinned-disk mill and granulating the powder in a fluidized bed by spraying on water as granulating fluid.

Water-dispersible granules are also obtained by homogenizing and precomminuting 25 parts by weight of a compound of the formula (I),
5 " of sodium 2,2'-dinaphthylmethane-6,6'-disulfonate,
2 " of sodium oleoylmethyltaurate,
1 " of polyvinyl alcohol,
17 " of calcium carbonate and
50 " of water in a colloid mill, subsequently grinding the mixture in a bead mill and atomizing and drying the suspension obtained in a spray tower by means of a single-substance nozzle.

C. BIOLOGICAL EXAMPLES

1. Herbicidal Action Pre-Emergence

Seeds of mono- and dicotyledonous harmful plants are put into sandy loam in cardboard pots and covered with soil. The compounds according to the invention, which are formulated in the form of wettable powders or emulsion concentrates, are then applied to the surface of the soil cover as an aqueous suspension or emulsion at an application rate of 600 to 800 l/ha (converted) in various dosages. After the treatment, the pots are placed in a greenhouse and kept under good growth conditions for the weeds. Visual scoring of the plant damage or emergence damage is carried out after the test plants have emerged after a test period of 3 to 4 weeks in comparison with untreated controls. After the test plants have stood in the greenhouse under optimum growth conditions for 3 to 4 weeks, the effect of the compounds is scored. Here, the compounds according to the invention have excellent activity against a broad spectrum of economically important mono- and dicotyledonous harmful plants.

Thus, for example, the compound according to the invention of No. 1.1 shows, at a dosage of 320 g/ha, at least 90% action against the harmful plants *Galium aparine, Matricaria inodora, Stellaria media, Chenopodium album, Veronica persica* and *Abutilon theophrasti*.

2. Herbicidal Action Post-Emergence

Seeds of mono- and dicotyledonous weeds are put into sandy loam in cardboard pots, covered with soil and grown in the greenhouse under good growth conditions. Two to three weeks after sowing, the test plants are treated in the three-leaf stage. The compounds according to the invention, which are formulated as wettable powders or as emulsion concentrates, are sprayed onto the surface of the green plant parts in various dosages at a water application rate of 600 to 800 l/ha (converted). After the test plants have been left to stand in the greenhouse for 3 to 4 weeks under optimal growth conditions, the action of the compounds is scored. The compositions according to the invention here show excellent activity against a broad spectrum of economically important mono- and dicotyledonous harmful plants. Thus, for example, the compound according to the invention of No. 3.1 shows, at a dosage of 320 g/ha, an action of at least 80% against the harmful plants *Sinapis arvensis, Avena fatua, Amaranthus retroflexus* and *Setaria viridis*.

3. Crop Plant Tolerance

In further experiments in the greenhouse, seeds of barley and mono- and dicotyledonous weeds are put in sandy loam and covered with soil and placed in the greenhouse until the plants have developed two to three true leaves. Treatment with the compounds of the formula (I) according to the invention is then carried out as described under item 2. Four to five weeks after application and after the plants have remained in the greenhouse, it is found by means of visual scoring that the compounds according to the invention are tolerated extremely well by important crop plants, in particular wheat, corn and rice.

Thus, for example, the compound according to the invention of No. 1.1 shows, at a dosage of 50 g/ha, at least 95% action against the harmful plants *Echinochloa crusgalli, Sagittaria pygmaea, Cyperus serotinus* and *Scirpus juncoides*, while at the same time, the crop plant rice is not damaged. At a dosage of 320 g/ha, the compound according to the invention of No. 1.85 shows at least 90% action against the harmful plants *Stellaria media, Veronica persica, Chenopodium album* and *Abutilon theophrasti*, while at the same time no damage is caused to the crop plants rice, wheat and corn.

The invention claimed is:

1. A compound of the formula (I) or a salt thereof

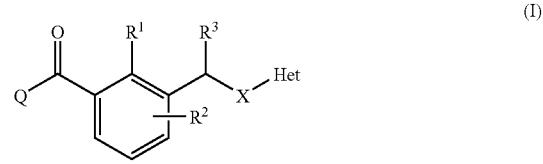

in which the radicals and indices are as defined below:

$R^1$, $R^2$ independently of one another are hydrogen, mercapto, nitro, halogen, cyano, thiocyanato, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, —$OR^4$, $OCOR^4$, $OSO_2R^4$, $S(O)_nR^4$, $SO_2OR^4$, $SO_2N(R^4)_2$, $NR^4SO_2R^4$, $NR^4COR^4$, $C_1$-$C_6$-alkyl-$S(O)_nR^4$, $C_1$-$C_6$-alkyl-$OR^4$, $C_1$-$C_6$-alkyl-$OCOR^4$, $C_1$-$C_6$-alkyl-$OSO_2R^4$, $C_1$-$C_6$-alkyl-$SO_2OR^4$, $C_1$-$C_6$-alkyl-$SO_2N(R^4)_2$ or $C_1$-$C_6$-alkyl-$NR^4COR^4$;

$R^3$ is hydrogen, $C_1$-$C_6$-alkyl, $C_2$-$C_6$-alkenyl or $C_2$-$C_6$-alkynyl;

$R^4$ is hydrogen, $C_1$-$C_6$-alkyl, $C_2$-$C_6$-alkenyl, $C_2$-$C_6$-alkynyl, $C_3$-$C_6$-cycloalkyl, phenyl or phenyl-$C_1$-$C_6$-alkyl, where the six last-mentioned radicals are substituted by s radicals selected from the group consisting of hydroxy, mercapto, amino, cyano, nitro, thiocyanato, $OR^3$, $SR^3$, $N(R^3)_2$, =$NOR^3$, $OCOR^3$, $SCOR^3$, $NR^3COR^3$, $CO_2R^3$, $COSR^3$, $CON(R^3)_2$, $C_1$-$C_4$-alkyliminooxy, $C_1$-$C_4$-alkoxyamino, $C_1$-$C_4$-alkylcarbonyl, $C_1$-$C_4$-alkoxy-$C_2$-$C_6$-alkoxycarbonyl and $C_1$-$C_4$-alkylsulfonyl;

Het is 3-tetrahydrofuranyl, 3-tetrahydropyranyl, 4-tetrahydropyranyl, 1,3-dioxan-5-yl or γ-butyrolacton-2-yl, which may be substituted by n radicals $R^5$;

n is 0, 1 or 2;
s is 0, 1, 2 or 3;
X is O or $S(O)_n$;
$R^5$ is hydroxy, mercapto, amino, cyano, nitro, halogen, formyl, $C_1$-$C_6$-alkylamino, $C_1$-$C_6$-dialkylamino, $C_1$-$C_6$-alkoxycarbonyl, $C_1$-$C_6$-alkylcarbonyl, $C_1$-$C_4$-alkylcarbonyloxy, $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy, or $C_1$-$C_6$-haloalkoxy or $R^5$ together with the carbon atom to which it is attached forms a carbonyl group;
Q is a radical of group Q1 or Q2;

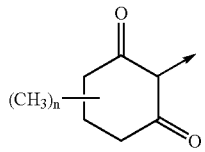

Q1

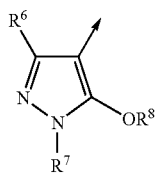

Q2

$R^6$, $R^7$ independently of one another are hydrogen, $C_1$-$C_6$-alkyl, $C_1$-$C_6$-haloalkyl or $C_3$-$C_6$-cyclopropyl;
$R^8$ is hydrogen, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, phenylcarbonyl, phenylcarbonylmethyl, phenyloxycarbonyl or phenylsulfonyl, where the phenyl ring of the four last-mentioned radicals is substituted by s radicals selected from the group consisting of halogen, nitro, cyano, $C_1$-$C_6$-alkyl, $C_1$-$C_6$-haloalkyl, $C_1$-$C_6$-alkoxy and $C_1$-$C_6$-haloalkoxy.

2. A compound as claimed in claim 1, in which
$R^1$, $R^2$ independently of one another are hydrogen, nitro, halogen, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, —$OR^4$, $S(O)_nR^4$, $SO_2OR^4$, $SO_2N(R^4)_2$, $NR^4SO_2R^4$ or $C_1$-$C_6$-alkyl-$S(O)_nR^4$;
$R^4$ is hydrogen, $C_1$-$C_4$-alkyl, $C_2$-$C_4$-alkenyl, $C_2$-$C_4$-alkynyl, $C_3$-$C_6$-cycloalkyl, phenyl or phenyl-$C_1$-$C_4$-alkyl, where the six last-mentioned radicals are substituted by s radicals selected from the group consisting of cyano, nitro, $R^3$, $OR^3$, $SR^3$ and $N(R^3)_2$.

3. A compound as claimed in claim 1, in which
$R^3$ is hydrogen;
$R^5$ is cyano, nitro, halogen, $C_1$-$C_4$-alkoxycarbonyl, $C_1$-$C_4$-alkylcarbonyl, $C_1$-$C_4$-alkylcarbonyloxy, $C_1$-$C_4$-alkyl, $C_1$-$C_4$-haloalkyl, $C_1$-$C_4$-alkylthio, $C_1$-$C_4$-haloalkylthio, $C_1$-$C_6$-alkoxy, or $C_1$-$C_6$-haloalkoxy, or $R^5$ together with the carbon atom to which it is attached forms a carbonyl group.

4. A compound as claimed in claim 1, in which
$R^6$, $R^7$ independently of one another are hydrogen or $C_1$-$C_4$-alkyl;
$R^8$ is hydrogen, $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxycarbonyl, $C_1$-$C_4$-alkylsulfonyl, $C_1$-$C_4$-haloalkylsulfonyl, phenylcarbonyl, phenylcarbonylmethyl, phenyloxycarbonyl or phenylsulfonyl, where the phenyl ring of the four last-mentioned radicals is substituted by s radicals selected from the group consisting of halogen, nitro, cyano, $C_1$-$C_4$-alkyl, $C_1$-$C_4$-haloalkyl, $C_1$-$C_4$-alkoxy and $C_1$-$C_4$-haloalkoxy.

5. A compound as claimed in claim 1, in which
$R^1$ is chlorine, bromine, iodine, nitro, methyl, thiomethyl, thioethyl, methylsulfonyl, ethylsulfonyl or methoxy;
$R^2$ is bromine, chlorine, methylsulfonyl or ethylsulfonyl;
$R^2$ is located in the 4-position of the phenyl ring; and
$R^8$ is hydrogen.

6. A herbicidal composition which comprises a herbicidally effective amount of at least one compound of the formula (I) as claimed in claim 1.

7. A herbicidal composition as claimed in claim 6 in a mixture with at least one formulation auxiliary selected from the group consisting of stickers, wetters, dispersants, emulsifiers, penetrants, preservatives, antifreeze agents, solvents, fillers, carriers, colorants, antifoams, evaporation inhibitors, pH regulators and viscosity regulators.

8. A compound of the formula (I) or a salt thereof

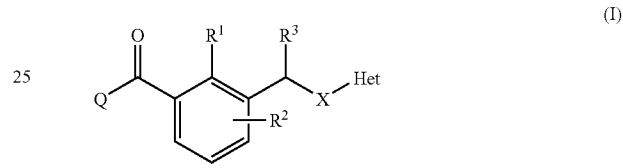

(I)

in which the radicals and indices are as defined below:
$R^1$, $R^2$ independently of one another are hydrogen, mercapto, nitro, halogen, cyano, thiocyanato, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, —$OR^4$, $OCOR^4$, $OSO_2R^4$, $S(O)_nR^4$, $SO_2OR^4$, $SO_2N(R^4)_2$, $NR^4SO_2R^4$, $NR^4COR^4$, $C_1$-$C_6$-alkyl-$S(O)_nR^4$, $C_1$-$C_6$-alkyl-$OR^4$, $C_1$-$C_6$-alkyl-$OCOR^4$, $C_1$-$C_6$-alkyl-$OSO_2R^4$, $C_1$-$C_6$-alkyl-$SO_2OR^4$, $C_1$-$C_6$-alkyl-$SO_2N(R^4)_2$ or $C_1$-$C_6$-alkyl-$NR^4COR^4$;
$R^3$ is hydrogen, $C_1$-$C_6$-alkyl, $C_2$-$C_6$-alkenyl or $C_2$-$C_6$-alkynyl;
$R^4$ is hydrogen, $C_1$-$C_6$-alkyl, $C_2$-$C_6$-alkenyl, $C_2$-$C_6$-alkynyl, $C_3$-$C_6$-cycloalkyl, phenyl or phenyl-$C_1$-$C_6$-alkyl, where the six last-mentioned radicals are substituted by s radicals selected from the group consisting of hydroxy, mercapto, amino, cyano, nitro, thiocyanato, $OR^3$, $SR^3$, $N(R^3)_2$, =$NOR^3$, $OCOR^3$, $SCOR^3$, $NR^3COR^3$, $CO_2R^3$, $COSR^3$, $CON(R^3)_2$, $C_1$-$C_4$-alkyliminooxy, $C_1$-$C_4$-alkoxyamino, $C_1$-$C_4$-alkylcarbonyl, $C_1$-$C_4$-alkoxy-$C_2$-$C_6$-alkoxycarbonyl and $C_1$-$C_4$-alkylsulfonyl;
Het is 3-tetrahydrofuranyl, 3-tetrahydropyranyl, 4-tetrahydropyranyl, 1,3-dioxan-5-yl or γ-butyrolacton-2-yl;
n is 0, 1 or 2;
s is 0, 1, 2 or 3;
X is O or $S(O)_n$;
Q is a radical of group Q1 or Q2;

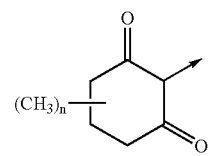

Q1

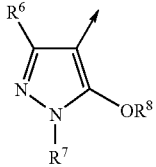

Q2

$R^6$, $R^7$ independently of one another are hydrogen, $C_1$-$C_6$-alkyl, $C_1$-$C_6$-haloalkyl or $C_3$-$C_6$-cyclopropyl;

$R^8$ is hydrogen, $C_1$-$C_6$-alkyl, $C_1$-$C_6$-haloalkyl, $C_1$-$C_6$-alkylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkyl-sulfonyl, phenylcarbonyl, phenylcarbonylmethyl, phenyloxycarbonyl or phenylsulfonyl, where the phenyl ring of the four last-mentioned radicals is substituted by s radicals selected from the group consisting of halogen, nitro, cyano, $C_1$-$C_6$-alkyl, $C_1$-$C_6$-haloalkyl, $C_1$-$C_6$-alkoxy and $C_1$-$C_6$-haloalkoxy.

9. A compound as claimed in claim 1, in which:

Q is Q1;
n is 0;
$R^1$ is Cl;
$R^2$ is $SO_2Me$;
$R^3$ is H;
X is O; and
Het is 3-tetrahydrofuranyl.

* * * * *